(12) United States Patent
Tompkins et al.

(10) Patent No.: US 6,331,616 B1
(45) Date of Patent: Dec. 18, 2001

(54) NUCLEIC ACIDS OBTAINED FROM THE ENVELOPE CODING REGION OF FELINE IMMUNODEFICIENCY VIRUS MOLECULAR CLONE DESIGNATED JSY3

(75) Inventors: Wayne Tompkins; Mary Tompkins; Joo-Sung Yang, all of Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 08/811,682

(22) Filed: Mar. 5, 1997

(51) Int. Cl.$^7$ .................................................. C07H 21/04
(52) U.S. Cl. ................................. 536/23.72; 424/188.1; 424/208.1
(58) Field of Search ................. 435/235.1; 424/188.1, 424/208.1; 536/23.1, 23.72

(56) References Cited

U.S. PATENT DOCUMENTS

| | | | |
|---|---|---|---|
| 5,413,927 | 5/1995 | Tompkins et al. | 435/239 |
| 5,736,378 | * 4/1998 | Elder et al. | 435/235.1 |

OTHER PUBLICATIONS

Yamamoto, J.K., et al., 1995, Genbank Acc. Nos. L00608 and L00609.*

J. Yang et al., *Molecularly Cloned Feline Immunodeficiency Virus NCSU$_1$ JSY3 Induces Immunodeficiency in Specific–Pathogen–Free Cats*, Jour. of Virology 70(5):3011–3017 (1996).

J. Yang et al., Third Int'l Feline Retrovirus Research Symposium, Mar. 6–9, 1996 (Abstract).

* cited by examiner

Primary Examiner—Laurie Scheiner
Assistant Examiner—Jeffrey S. Parkin

(74) Attorney, Agent, or Firm—Myers Bigel Sibley & Sajovec

(57) ABSTRACT

A full-length feline immunodeficiency virus NCSU$_1$ (FIV-NCSU$_1$) genome (JSY3) was cloned directly from FIV-NCSU$_1$-infected feline CD4$^+$ lymphocyte (FCD4E) genomic DNA and identified by PCR amplification with 5' long terminal repeat (LTR), gag, env, and 3' LTR primer sets. Cell-free JSY3 virus was cytopathogenic for FCD4E lymphocytes but did not infect CrFK cells in vitro. To determine in vivo infectivity and pathogenesis, six young adult specific-pathogen-free cats were inoculated with cell-free JSY3 virus. Provirus was detected at 2 weeks postinfection (p.i.) and was still detectable at 25 weeks p.i. as determined by gag region PCR-Southern blot analysis of peripheral blood mononuclear cell lysates. Infectious virus was recovered from peripheral blood mononuclear cells at 6 and 25 weeks p.i., and an antibody response to FIV was detected by 4 weeks. In the acute phase of infection, JSY3 provirus was found only in the CD4$^+$ lymphocyte subset; however, by 14 weeks p.i., the greatest provirus burden was detected in B lymphocytes. All six cats were panlymphopenic at 2 weeks p.i., CD4+/CD8+ ratios were inverted by 6 weeks p.i., and five of the six cats developed lymphadenopathy by 10 weeks p.i. The claimed invention is directed toward isolated nucleic acids corresponding to the full-length JSY3 env coding region (nt. 6269–8824) and an env fragment comprising the transmembrane spanning domain (nt. 8339–8374). These nucleic acids will prove useful, inter alia, as molecular probes for FIV-specific sequences and in the generation of FIV-specific antigens and immunological reagents.

7 Claims, 39 Drawing Sheets

FIG. 1

DNA SEQUENCE OF JYS3

FIG. 1A

```
              430        440        450        460        470        480
               *    *     *    *     *    *     *    *     *    *     *    *
         TTCTGGGATG AGTATTGGGA CCCTGAAGAA ATAGAAAGAA TGCTTATGGA CTAGTGACTG
         AAGACCCTAC TCATAACCCT GGGACTTCTT TATCTTTCTT ACGAATACCT GATCACTGAC
          → JSY3

490        500        510        520        530        540
               *    *     *    *     *    *     *    *     *    *     *    *
         TTTACGAACA AATGATAAAT GATGGAAACA GCTGAGCATG ACTCATAGTT AAAGCGCTAG
         AAATGCTTGT TTACTATTTA CTACCTTTGT CGACTCGTAC TGAGTATCAA TTTCGCGATC 550        560        570        580        590        600
               *    *     *    *     *    *     *    *     *    *     *    *
         CAGCTGCTTA ACCGCAAAAC CACATCCTAT GTAAAGCTTG CTGATGACGT ATAATTTGCT
         GTCGACGAAT TGGCGTTTTG GTGTAGGATA CATTTCGAAC GACTACTGCA TATTAAACGA 610        620        630        640        650        660
               *    *     *    *     *    *     *    *     *    *     *    *
         CCACTGTAAA AGTATATAAC CAGTGCTTTG TGAGACTTCG GGGAGTCTCT CCGTTGAGGA
         GGTGACATTT TCATATATTG GTCACGAAAC ACTCTGAAGC CCCTCAGAGA GGCAACTCCT 670        680        690        700        710        720
               *    *     *    *     *    *     *    *     *    *     *    *
         CTTTCGAGTT CTCCCTTGAG GCTCCCACAG ATACAATAAA TATTTGAGAT TGAACCCTGT
         GAAAGCTCAA GAGGGAACTC CGAGGGTGTC TATGTTATTT ATAAACTCTA ACTTGGGACA
```

```
           730         740         750         760         770         780
       *     *     *     *     *     *     *     *     *     *     *     *
   CAAGTATCTG  TGTAATCTTT  TTTACCTGTG  AGGTCTCGGA  ATCCGGGCCG  AGAACTTCGC
   GTTCATAGAC  ACATTAGAAA  AAATGGACAC  TCCAGAGCCT  TAGGCCCGGC  TCTTGAAGCG 790         800         810         820         830         840
       *     *     *     *     *     *     *     *     *     *     *     *
   AGTTGGCGCC  CGAACAGGGA  CTTGATTGAG  AGTGATTGAG  GAAGTGAAGC  TAGAGCAATA
   TCAACCGCGG  GCTTGTCCCT  GAACTAACTC  TCACTAACTC  CTTCACTTCG  ATCTCGTTAT 850         860         870         880         890         900
       *     *     *     *     *     *     *     *     *     *     *     *
   GAAAGCTGTT  AAGCAGAACT  CCTGCTGACC  TAAATAGGGA  AGCAGTAGCA  GACGCTGCTA
   CTTTCGACAA  TTCGTCTTGA  GGACGACTGG  ATTTATCCCT  TCGTCATCGT  CTGCGACGAT 910         920         930         940         950         960
       *     *     *     *     *     *     *     *     *     *     *     *
   ACAGTGAGTA  TCTCTAGTGA  AGCAGACTCG  AGCTCATAAT  CAAGTCACTG  TTTAAAGGCC
   TGTCACTCAT  AGAGATCACT  TCGTCTGAGC  TCGAGTATTA  GTTCAGTGAC  AAATTTCCGG 970         980         990        1000        1010        1020
       *     *     *     *     *     *     *     *     *     *     *     *
   CAGATAAATT  ACATCTGGTG  ACTCTTCGCG  GACCTTCAAG  CCAGGAGATT  CGCCGAGGGA
   GTCTATTTAA  TGTAGACCAC  TGAGAAGCGC  CTGGAAGTTC  GGTCCTCTAA  GCGGCTCCCT 1030        1040        1050        1060        1070        1080
       *     *     *     *     *     *     *     *     *     *     *     *
   CAGTCAACAA  GGTAGGAGAG  ATTCTGCAGC  AACATGGGGA  ACGGACAGGG  GCGAGATTGG
   GTCAGTTGTT  CCATCCTCTC  TAAGACGTCG  TTGTACCCCT  TGCCTGTCCC  CGCTCTAACC
                                                M   G    N  G  Q  G   R  D  W>
                                            GAG →
          1090        1100        1110        1120        1130        1140
       *     *     *     *     *     *     *     *     *     *     *     *
   AAAATGGCCA  TTAAGAGATG  TAGTAATGTT  GCTGTAGGAG  TAGGGGGGAA  GAGTAAAAAA
   TTTTACCGGT  AATTCTCTAC  ATCATTACAA  CGACATCCTC  ATCCCCCTT   CTCATTTTTT
   K   M  A    I  K  R  C   S  N  V    A  V  G    V  G  G  K    S  K  K>

1150        1160        1170        1180        1190        1200
       *     *     *     *     *     *     *     *     *     *     *     *
   TTTGGAGAAG  GGAATTTCAG  ATGGGCCATT  AGAATGGCTA  ATGTATCTAC  AGGACGAGAA
   AAACCTCTTC  CCTTAAAGTC  TACCCGGTAA  TCTTACCGAT  TACATAGATG  TCCTGCTCTT
   F   G  E    G  N  F  R   W  A  I    R  M  A    N  V  S  T     G  R  E>

1210        1220        1230        1240        1250        1260
       *     *     *     *     *     *     *     *     *     *     *     *
   CCTGGTGATA  TACCAGAGAC  TTTAGATCAA  CTAAGGTTGG  TTATTTGCGA  TTTACAAGAA
   GGACCACTAT  ATGGTCTCTG  AAATCTAGTT  GATTCCAACC  AATAAACGCT  AAATGTTCTT
   P   G  D    I  P  E  T   L  D  Q    L  R  L    V  I  C  D    L  Q  E>

1270        1280        1290        1300        1310        1320
       *     *     *     *     *     *     *     *     *     *     *     *
   AGAAGAGAAA  AATTTGGGTC  GAGCAAAGAA  ATTGACATGG  CAATTGTTAC  ATTAAAAGTC
   TCTTCTCTTT  TTAAACCCAG  CTCGTTTCTT  TAACTGTACC  GTTAACAATG  TAATTTTCAG
   R   R  E    K  F  G  S   S  K  E    I  D  M    A  I  V  T    L  K  V>

1330        1340        1350        1360        1370        1380
       *     *     *     *     *     *     *     *     *     *     *     *
   TTTGCGGTAG  TAGGACTTTT  AAATATGACA  GTGTCTACTG  CTGCTGCAGC  TGAAAATATG
   AAACGCCATC  ATCCTGAAAA  TTTATACTGT  CACAGATGAC  GACGACGTCG  ACTTTTATAC
   F   A  V    V  G  L  L   N  M  T    V  S  T    A  A  A  A     E  N  M>
```

FIG. 1B

```
          1390       1400       1410       1420       1430       1440
           *    *     *    *     *    *     *    *     *    *     *    *
      TACACTCAGA TGGGATTAGA CACTAGACCA TCTATGAGAG AAGCAGGAGG AAAAGAGGAA
      ATGTGAGTCT ACCCTAATCT GTGATCTGGT AGATACTCTC TTCGTCCTCC TTTTCTCCTT
       Y  T  Q   M  G  L  D   T  R  P   S  M  R   E  A  G  G   K  E  E>

1450       1460       1470       1480       1490       1500
           *    *     *    *     *    *     *    *     *    *     *    *
      AGCCCTCCAC AGGCATCTCC TATTCAAACA GCAAATGGAG CACCACAATA TGTAGCACTT
      TCGGGAGGTG TCCGTAGAGG ATAAGTTTGT CGTTTACCTC GTGGTGTTAT ACATCGTGAA
       S  P  P   Q  A  S  P   I  Q  T   A  N  G   A  P  Q  Y   V  A  L>
                        p15 ←→ p25

1510       1520       1530       1540       1550       1560
           *    *     *    *     *    *     *    *     *    *     *    *
      GACCCAAAAA TGGTGTCCAT TTTTATGGAA AAGGCAAGAG AAGGATTAGG AGGTGAGGAA
      CTGGGTTTTT ACCACAGGTA AAAATACCTT TTCCGTTCTC TTCCTAATCC TCCACTCCTT
       D  P  K   M  V  S  I   F  M  E   K  A  R   E  G  L  G   G  E  E>

1570       1580       1590       1600       1610       1620
           *    *     *    *     *    *     *    *     *    *     *    *
      GTTCAGCTAT GGTTTACTGC CTTCTCTGCA AATTTAACAC CTACTGACAT GGCCACATTA
      CAAGTCGATA CCAAATGACG GAAGAGACGT TTAAATTGTG GATGACTGTA CCGGTGTAAT
       V  Q  L   W  F  T  A   F  S  A   N  L  T   P  T  D  M   A  T  L>

1630       1640       1650       1660       1670       1680
           *    *     *    *     *    *     *    *     *    *     *    *
      ATAATGGCCG CACCAGGGTG CGCTGCAGAT AAAGAAATAT TGGATGAAAG CTTAAAGCAA
      TATTACCGGC GTGGTCCCAC GCGACGTCTA TTTCTTTATA ACCTACTTTC GAATTTCGTT
       I  M  A   A  P  G  C   A  A  D   K  E  I   L  D  E  S   L  K  Q>

1690       1700       1710       1720       1730       1740
           *    *     *    *     *    *     *    *     *    *     *    *
      TTGACGGCAG AGTATGATCG TACCCATCCT CCTGATGGAC CTAGACCATT ACCCTATTTT
      AACTGCCGTC TCATACTAGC ATGGGTAGGA GGACTACCTG GATCTGGTAA TGGGATAAAA
       L  T  A   E  Y  D  R   T  H  P   P  D  G   P  R  P  L   P  Y  F>
                 ──────────────────────────────────────────────
                                       P24A 1750       1760       1770       1780       1790       1800
           *    *     *    *     *    *     *    *     *    *     *    *
      ACTGCAGCAG AAATTATGGG TATAGGATTA ACTCAAGAAC AACAAGCAGA AGCAAGATTT
      TGACGTCGTC TTTAATACCC ATATCCTAAT TGAGTTCTTG TTGTTCGTCT TCGTTCTAAA
       T  A  A   E  I  M  G   I  G  L   T  Q  E   Q  Q  A  E   A  R  F>

1810       1820       1830       1840       1850       1860
           *    *     *    *     *    *     *    *     *    *     *    *
      GCACCAGCTA GGATGCAGTG TAGAGCATGG TATCTCGAGG CACTAGGAAA ATTGGCCGCC
      CGTGGTCGAT CCTACGTCAC ATCTCGTACC ATAGAGCTCC GTGATCCTTT TAACCGGCGG
       A  P  A   R  M  Q  C   R  A  W   Y  L  E   A  L  G  K   L  A  A>

1870       1880       1890       1900       1910       1920
           *    *     *    *     *    *     *    *     *    *     *    *
      ATAAAAGCTA AGTCTCCTCG AGCTGTGCAG TTAAGACAAG GAGCTAAGGA AGATTATTCA
      TATTTTCGAT TCAGAGGAGC TCGACACGTC AATTCTGTTC CTCGATTCCT TCTAATAAGT
       I  K  A   K  S  P  R   A  V  Q   L  R  Q   G  A  K  E   D  Y  S>

1930       1940       1950       1960       1970       1980
           *    *     *    *     *    *     *    *     *    *     *    *
      TCCTTTATAG ACAGATTGTT TGCCCAAATA GATCAAGAAC AAAATACAGC TGAAGTTAAG
      AGGAAATATC TGTCTAACAA ACGGGTTTAT CTAGTTCTTG TTTTATGTCG ACTTCAATTC
       S  F  I   D  R  L  F   A  Q  I   D  Q  E   Q  N  T  A   E  V  K>
```

FIG. 1C

```
          1990        2000        2010        2020        2030        2040
            *   *       *   *       *   *       *   *       *   *       *   *
     TTATATTTAA  AACAGTCATT  AAGCATGGCT  AATGCTAATG  CAGAATGTAA  AAAGGCAATG
     AATATAAATT  TTGTCAGTAA  TTCGTACCGA  TTACGATTAC  GTCTTACATT  TTTCCGTTAC
      L Y L       K Q S L     S M A       N A N       A E C K     K A M>

2050        2060        2070        2080        2090        2100
            *   *       *   *       *   *       *   *       *   *       *   *
     AGCCACCTTA  AGCCAGAAAG  TACCCTAGAA  GAAAAGCTGA  GAGCTTGTCA  AGAAGTAGGC
     TCGGTGGAAT  TCGGTCTTTC  ATGGGATCTT  CTTTTCGACT  CTCGAACAGT  TCTTCATCCG
      S H L       K P E S     T L E       E K L       R A C Q     E V G>

2110        2120        2130        2140        2150        2160
            *   *       *   *       *   *       *   *       *   *       *   *
     TCACCAGGAT  ATAAAATGCA  ACTCTTGGCA  GAAGCTCTTA  CAAAAGTTCA  AGTAGTGCAA
     AGTGGTCCTA  TATTTTACGT  TGAGAACCGT  CTTCGAGAAT  GTTTTCAAGT  TCATCACGTT
      S P G       Y K M Q     L L A       E A L       T K V Q     V V Q>
                                   p25 ←      → p10

2170        2180        2190        2200        2210        2220
            *   *       *   *       *   *       *   *       *   *       *   *
     TCAAAAGGAT  CAGGACCAGT  GTGTTTCAAC  TGTAAAAAAC  CAGGACATCT  AGCAAAACAG
     AGTTTTCCTA  GTCCTGGTCA  CACAAAGTTG  ACATTTTTTG  GTCCTGTAGA  TCGTTTTGTC
      S K G       S G P V     C F N       C K K       P G H L     A K Q>

2230        2240        2250        2260        2270        2280
            *   *       *   *       *   *       *   *       *   *       *   *
     TGTAGAGATG  TGAAAAAATG  TAATAAATGT  GGAAAGCCTG  GTCATTTAGC  TGCCAAATGC
     ACATCTCTAC  ACTTTTTTAC  ATTATTTACA  CCTTTCGGAC  CAGTAAATCG  ACGGTTTACG
      C R D       V K K C     N K C       G K P       G H L A     A K C>

2290        2300        2310        2320        2330        2340
            *   *       *   *       *   *       *   *       *   *       *   *
     TGGCAAGGTG  GTAAAAGAA   TTCGGGAAAC  TGGAAGGCGG  GGCGAGCTGC  AGCCCCAGTG
     ACCGTTCCAC  CATTTTTCTT  AAGCCCTTTG  ACCTTCCGCC  CCGCTCGACG  TCGGGGTCAC
      W Q G       G K K N     S G N       W K A       G R A A     A P V>

2350        2360        2370        2380        2390        2400
            *   *       *   *       *   *       *   *       *   *       *   *
     AATCAAGTGC  AGCAAGCAGT  AATGCCATCT  GCACCTCCAA  TGGAGGAGAG  ACTATTGGAT
     TTAGTTCACG  TCGTTCGTCA  TTACGGTAGA  CGTGGAGGTT  ACCTCCTCTC  TGATAACCTA
      N Q V       Q Q A V     M P S       A P P       M E E R     L L D>

2410        2420        2430        2440        2450        2460
            *   *       *   *       *   *       *   *       *   *       *   *
     TTATAAATTA  TAATAAAGTA  GGTACTACTA  CAACATTAGA  AAAGAGGCCA  GAAATACTTA
     AATATTTAAT  ATTATTTCAT  CCATGATGAT  GTTGTAATCT  TTTCTCCGGT  CTTTATGAAT
      L>
     ← p10

2470        2480        2490        2500        2510        2520
            *   *       *   *       *   *       *   *       *   *       *   *
     TATTTGTAAA  TGGGTACCCT  ATAAAATTTT  TATTAGATAC  AGGAGCAGAT  ATAACAATTT
     ATAAACATTT  ACCCATGGGA  TATTTAAAA   ATAATCTATG  TCCTCGTCTA  TATTGTTAAA 2530        2540        2550        2560        2570        2580
            *   *       *   *       *   *       *   *       *   *       *   *
     TAAATAGGAG  AGATTTTCAA  GTAAAAAATT  CTATAGAAAA  TGGAAGGCAA  AATATGATTG
     ATTTATCCTC  TCTAAAAGTT  CATTTTTAA   GATATCTTTT  ACCTTCCGTT  TTATACTAAC
                                                                 M I >
                                                                → pol
                                                                  ORF1
```

FIG. 1D

```
            2590        2600        2610        2620        2630        2640
              *           *           *           *           *           *
         GAGTAGGAGG  AGGAAAGAGA  GGAACAAATT  ATATCAATGT  GCATTTAGAG  ATTAGAGATG
         CTCATCCTCC  TCCTTTCTCT  CCTTGTTTAA  TATAGTTACA  CGTAAATCTC  TAATCTCTAC
          G  V  G  G   G  K  R    G  T  N    Y  I  N  V  H  L  E    I  R  D >

2650        2660        2670        2680        2690        2700
              *           *           *           *           *           *
         AAAATTATAA  GACACAATGT  ATATTTGGCA  ATGTTTGTGT  CTTAGAAGAT  AACTCATTAA
         TTTTAATATT  CTGTGTTACA  TATAAACCGT  TACAAACACA  GAATCTTCTA  TTGAGTAATT
          E  N  Y  K   T  Q  C    I  F  G    N  V  C  V  L  E  D    N  S  L >

2710        2720        2730        2740        2750        2760
              *           *           *           *           *           *
         TACAACCATT  ATTAGGGAGA  GATAATATGA  TTAGATTCAA  TATTAGGTTA  GTAATGGCTC
         ATGTTGGTAA  TAATCCCTCT  CTATTATACT  AATCTAAGTT  ATAATCCAAT  CATTACCGAG
          I  Q  P  L   L  G  R    D  N  M    I  R  F  N  I  R  L    V  M  A >

2770        2780        2790        2800        2810        2820
              *           *           *           *           *           *
         AAATTTCTGA  CAAGATTCCA  ATAGTAAAAG  TAAAAATGAA  GGATCCAAAT  AAAGGACCTC
         TTTAAAGACT  GTTCTAAGGT  TATCATTTTC  ATTTTTACTT  CCTAGGTTTA  TTTCCTGGAG
          Q  I  S  D   K  I  P    I  V  K    V  K  M  K  D  P  N    K  G  P >

2830        2840        2850        2860        2870        2880
              *           *           *           *           *           *
         AAATAAAACA  ATGGCCATTA  ACAAATGAAA  AAATTGAAGC  TTTAACAGAA  ATAGTAGAAA
         TTTATTTTGT  TACCGGTAAT  TGTTTACTTT  TTTAACTTCG  AAATTGTCTT  TATCATCTTT
          Q  I  K  Q   W  P  L    T  N  E    K  I  E  A  L  T  E    I  V  E >

2890        2900        2910        2920        2930        2940
              *           *           *           *           *           *
         GACTAGAAAG  AGAAGGGAAA  GTAAAAAGAG  CAGATCCAAA  TAACCCATGG  AATACACCAG
         CTGATCTTTC  TCTTCCCTTT  CATTTTTCTC  GTCTAGGTTT  ATTGGGTACC  TTATGTGGTC
          R  L  E  R   E  G  K    V  K  R    A  D  P  N  N  P  W    N  T  P >

2950        2960        2970        2980        2990        3000
              *           *           *           *           *           *
         TATTTGCAAT  AAAAAAGAAA  AGTGGAAAAT  GGAGAATGCT  CATAGATTTT  AGAGAATTGA
         ATAAACGTTA  TTTTTTCTTT  TCACCTTTTA  CCTCTTACGA  GTATCTAAAA  TCTCTTAACT
          V  F  A  I   K  K  K    S  G  K    W  R  M  L  I  D  F    R  E  L >

3010        3020        3030        3040        3050        3060
              *           *           *           *           *           *
         ACAAATTAAC  TGAGAAAGGG  GCAGAAGTCC  AGTTAGGACT  CCCTCATCCT  GCTGGATTAA
         TGTTTAATTG  ACTCTTTCCC  CGTCTTCAGG  TCAATCCTGA  GGGAGTAGGA  CGACCTAATT
          N  K  L  T   E  K  G    A  E  V    Q  L  G  L  P  H  P    A  G  L >

3070        3080        3090        3100        3110        3120
              *           *           *           *           *           *
         AAATGAAAAA  ACAAGTTACT  GTGCTAGATA  TAGGAGATGC  ATACTTCACT  ATTCCCTTGG
         TTTACTTTTT  TGTTCAATGA  CACGATCTAT  ATCCTCTACG  TATGAAGTGA  TAAGGGAACC
          K  M  K  K   Q  V  T    V  L  D    I  G  D  A  Y  F  T    I  P  L >

3130        3140        3150        3160        3170        3180
              *           *           *           *           *           *
         ATCCAGACTA  TGCTCCCTAT  ACTGCATTCA  CATTACCTAG  AAAGAATAAT  GCAGGACCAG
         TAGGTCTGAT  ACGAGGGATA  TGACGTAAGT  GTAATGGATC  TTTCTTATTA  CGTCCTGGTC
          D  P  D  Y   A  P  Y    T  A  F    T  L  P  R  K  N  N    A  G  P >

3190        3200        3210        3220        3230        3240
              *           *           *           *           *           *
         GGAGGAGATA  TGTATGGTGC  AGTTTACCAC  AGGGGTGGGT  TCTAAGCCCA  TTGATATATC
         CCTCCTCTAT  ACATACCACG  TCAAATGGTG  TCCCCACCCA  AGATTCGGGT  AACTATATAG
          G  R  R  Y   V  W  C    S  L  P    Q  G  W  V  L  S  P    L  I  Y >
```

FIG. 1E

```
        3250        3260        3270        3280        3290        3300
          *           *           *           *           *           *
AAAGTACTTT  AGATAATATA  ATACAACCTT  TTATTAGACA  AAATCCTGAG  TTAGATATTT
TTTCATGAAA  TCTATTATAT  TATGTTGGAA  AATAATCTGT  TTTAGGACTC  AATCTATAAA
 Q  S  T  L    D  N  I    I  Q  P    F  I  R  Q    N  P  E    L  D  I  >

3310        3320        3330        3340        3350        3360
          *           *           *           *           *           *
ATCAATATAT  GGATGACATT  TATATAGGAT  CAAACTTAAG  TAAAAAGGAG  CATAAAGAAA
TAGTTATATA  CCTACTGTAA  ATATATCCTA  GTTTGAATTC  ATTTTTCCTC  GTATTTCTTT
 Y  Q  Y  M    D  D  I    Y  I  G    S  N  L    S  K  K  E    H  K  E  >

3370        3380        3390        3400        3410        3420
          *           *           *           *           *           *
AAGTAGAAGA  ATTAAGAAAA  TTGTTATTAT  GGTGGGGATT  TGAAACCCCG  GAAGACAAAT
TTCATCTTCT  TAATTCTTTT  AACAATAATA  CCACCCCTAA  ACTTTGGGGC  CTTCTGTTTA
 K  V  E  E    L  R  K    L  L  L    W  W  G  F    E  T  P    E  D  K  >

3430        3440        3450        3460        3470        3480
          *           *           *           *           *           *
TACAAGAAGA  GCCCCCATAT  AAGTGGATGG  GCTATGAATT  ACATCCATTA  ACATGGTCAA
ATGTTCTTCT  CGGGGGTATA  TTCACCTACC  CGATACTTAA  TGTAGGTAAT  TGTACCAGTT
 L  Q  E  E    P  P  Y    K  W  M    G  Y  E  L    H  P  L    T  W  S  >

3490        3500        3510        3520        3530        3540
          *           *           *           *           *           *
TACAGCAAAA  ACAATTAGAA  ATTCCAGAAA  GACCCACATT  AAATGAACTG  CAGAAATTAG
ATGTCGTTTT  TGTTAATCTT  TAAGGTCTTT  CTGGGTGTAA  TTTACTTGAC  GTCTTTAATC
 I  Q  Q  K    Q  L  E    I  P  E    R  P  T  L    N  E  L    Q  K  L  >

3550        3560        3570        3580        3590        3600
          *           *           *           *           *           *
CAGGTAAGAT  AAACTGGGCC  AGTCAAACTA  TCCCAGACTT  AAGTATAAAA  GAACTAACTA
GTCCATTCTA  TTTGACCCGG  TCAGTTTGAT  AGGGTCTGAA  TTCATATTTT  CTTGATTGAT
 A  G  K  I    N  W  A    S  Q  T    I  P  D  L    S  I  K    E  L  T  >

3610        3620        3630        3640        3650        3660
          *           *           *           *           *           *
ACATGATGAG  AGGAGATCAG  AAGTTAGACT  CAATAAGAGA  ATGGACTGTG  GAAGCCAAGA
TGTACTACTC  TCCTCTAGTC  TTCAATCTGA  GTTATTCTCT  TACCTGACAC  CTTCGGTTCT
 N  M  M  R    G  D  Q    K  L  D    S  I  R  E    W  T  V    E  A  K  >

3670        3680        3690        3700        3710        3720
          *           *           *           *           *           *
GAGAAGTACA  AAAAGCTAAG  GAAGCTATTG  AGATGCAAGC  ACAGCTAAAT  TATTATGATC
CTCTTCATGT  TTTTCGATTC  CTTCGATAAC  TCTACGTTCG  TGTCGATTTA  ATAATACTAG
 R  E  V  Q    K  A  K    E  A  I    E  M  Q  A    Q  L  N    Y  Y  D  >

3730        3740        3750        3760        3770        3780
          *           *           *           *           *           *
CCCACCGAGA  ATTATATGCA  AAATTAAGTT  TAGTGGGACC  ACATCAAATA  TGTTATCAAG
GGGTGGCTCT  TAATATACGT  TTTAATTCAA  ATCACCCTGG  TGTAGTTTAT  ACAATAGTTC
 P  H  R  E    L  Y  A    K  L  S    L  V  G  P    H  Q  I    C  Y  Q  >

3790        3800        3810        3820        3830        3840
          *           *           *           *           *           *
TGTATCATAA  GAACCCAGAA  TGTATTTTAT  GGTATGGTAA  GATGAATAGA  CAAAAGAAAA
ACATAGTATT  CTTGGGTCTT  ACATAAAATA  CCATACCATT  CTACTTATCT  GTTTTCTTTT
 V  Y  H  K    N  P  E    C  I  L    W  Y  G  K    M  N  R    Q  K  K  >

3850        3860        3870        3880        3890        3900
          *           *           *           *           *           *
AGGCAGAAAA  TACCTGTGAT  ATAGCTCTAA  GGGCATGTTA  TAAAATAAGA  GAAGAATCTA
TCCGTCTTTT  ATGGACACTA  TATCGAGATT  CCCGTACAAT  ATTTTATTCT  CTTCTTAGAT
 K  A  E  N    T  C  D    I  A  L    R  A  C  Y    K  I  R    E  E  S  >
```

FIG. 1F

```
            3910        3920        3930        3940        3950        3960
              *  *        *  *        *  *        *  *        *  *        *  *
        TTATAAGAAT  AGGAAAAGAA  CCAATATATG  AAATACCTAC  TTCTAGAGAA  GCCTGGGAGT
        AATATTCTTA  TCCTTTTCTT  GGTTATATAC  TTTATGGATG  AAGATCTCTT  CGGACCCTCA
         I  I  R  I   G  K  E    P  I  Y    E  I  P  T   S  R  E    A  W  E >

3970        3980        3990        4000        4010        4020
              *  *        *  *        *  *        *  *        *  *        *  *
        CAAATTTAAT  TAATTCACCA  TATCTTAAGG  CCCCACCTCC  TGAGGTAGAA  TATATCCATG
        GTTTAAATTA  ATTAAGTGGT  ATAGAATTCC  GGGGTGGAGG  ACTCCATCTT  ATATAGGTAC
         S  N  L  I   N  S  P    Y  L  K    A  P  P    P  E  V  E   Y  I  H >

4030        4040        4050        4060        4070        4080
              *  *        *  *        *  *        *  *        *  *        *  *
        CTGCTGTGAA  TATAAAAGA   GCATTAAGTA  TGATAAAAGA  TGTTCCAATA  CCAGAAGCAG
        GACGACACTT  ATATTTTTCT  CGTAATTCAT  ACTATTTTCT  ACAAGGTTAT  GGTCTTCGTC
         A  A  V  N   I  K  R    A  L  S    M  I  K  D   V  P  I    P  E  A >

4090        4100        4110        4120        4130        4140
              *  *        *  *        *  *        *  *        *  *        *  *
        AAACGTGGTA  TATAGATGGA  GGCAGAAAGC  TAGGAAAAGC  AGCAAAAGCA  GCCTATTGGA
        TTTGCACCAT  ATATCTACCT  CCGTCTTTCG  ATCCTTTTCG  TCGTTTTCGT  CGGATAACCT
         E  T  W  Y   I  D  G    G  R  K    L  G  K  A   A  K  A    A  Y  W >

4150        4160        4170        4180        4190        4200
              *  *        *  *        *  *        *  *        *  *        *  *
        CAGATACAGG  GAAGTGGCAA  GTAATGGAGT  TAGAAGGCAG  TAATCAGAAG  GCAGAAGTAC
        GTCTATGTCC  CTTCACCGTT  CATTACCTCA  ATCTTCCGTC  ATTAGTCTTC  CGTCTTCATG
         T  D  T  G   K  W  Q    V  M  E    L  E  G  S   N  Q  K    A  E  V >

4210        4220        4230        4240        4250        4260
              *  *        *  *        *  *        *  *        *  *        *  *
        AAGCATTATT  ATTGGCATTA  AAAGCAGGAT  CAGAGGAAAT  GAATATTATA  ACAGATTCAC
        TTCGTAATAA  TAACCGTAAT  TTTCGTCCTA  GTCTCCTTTA  CTTATAATAT  TGTCTAAGTG
         Q  A  L  L   L  A  L    K  A  G    S  E  E  M   N  I  I    T  D  S >

4270        4280        4290        4300        4310        4320
              *  *        *  *        *  *        *  *        *  *        *  *
        AATATGTTAT  AAATATTATT  CTTCAACAAC  CAGATATGAT  GGAGGGAATC  TGGCAAGAAG
        TTATACAATA  TTTATAATAA  GAAGTTGTTG  GTCTATACTA  CCTCCCTTAG  ACCGTTCTTC
         Q  Y  V  I   N  I  I    L  Q  Q    P  D  M  M   E  G  I    W  Q  E >

4330        4340        4350        4360        4370        4380
              *  *        *  *        *  *        *  *        *  *        *  *
        TTTTAGAAGA  ATTGGAGAAA  AAAACAGCAA  TATTTATAGA  TTGGGTCCCA  GGACATAAAG
        AAAATCTTCT  TAACCTCTTT  TTTTGTCGTT  ATAAATATCT  AACCCAGGGT  CCTGTATTTC
         V  L  E  E   L  E  K    K  T  A    I  F  I  D   W  V  P    G  H  K >

4390        4400        4410        4420        4430        4440
              *  *        *  *        *  *        *  *        *  *        *  *
        GTATTCCAGG  AAATGAGGAA  GTAGATAAGC  TTTGTCAAAC  AATGATGATA  ATAGAAGGGG
        CATAAGGTCC  TTTACTCCTT  CATCTATTCG  AAACAGTTTG  TTACTACTAT  TATCTTCCCC
         G  I  P  G   N  E  E    V  D  K    L  C  Q  T   M  M  I    E  G >

4450        4460        4470        4480        4490        4500
              *  *        *  *        *  *        *  *        *  *        *  *
        ATGGGATATT  AGATAAAAGG  TCAGAAGATG  CGGGATATGA  TTTATTGGCT  GCAAAAGAAA
        TACCCTATAA  TCTATTTTCC  AGTCTTCTAC  GCCCTATACT  AAATAACCGA  CGTTTTCTTT
         D  G  I  L   D  K  R    S  E  D    A  G  Y  D   L  L  A    A  K  E >

4510        4520        4530        4540        4550        4560
              *  *        *  *        *  *        *  *        *  *        *  *
        TACATTTATT  GCCAGGAGAG  GTAAAAGTAA  TACCAACAGG  GGTAAAGCTA  ATGCTGCCTA
        ATGTAAATAA  CGGTCCTCTC  CATTTTCATT  ATGGTTGTCC  CCATTTCGAT  TACGACGGAT
         I  H  L  L   P  G  E    V  K  V    I  P  T  G   V  K  L    M  L  P >
```

FIG. 1G

```
        4570        4580        4590        4600        4610        4620
          *           *           *           *           *           *
AAGGACATTG  GGGACTAATA  ATGGGAAGAA  GCTCGATAGG  GAGTAAAGGA  TTGGATGTAT
TTCCTGTAAC  CCCTGATTAT  TACCCTTCTT  CGAGCTATCC  CTCATTTCCT  AACCTACATA
 K  G  H  W   G  L  I    M  G  R    S  S  I     G  S  K  G   L  D  V >

4630        4640        4650        4660        4670        4680
          *           *           *           *           *           *
TAGGAGGGGT  AATAGATGAA  GGATATCGAG  GTGAAATTGG  AGTAATAATG  ATTAATGTAT
ATCCTCCCCA  TTATCTACTT  CCTATAGCTC  CACTTTAACC  TCATTATTAC  TAATTACATA
 L  G  G  V   I  D  E    G  Y  R    G  E  I  G   V  I  M    I  N  V >

4690        4700        4710        4720        4730        4740
          *           *           *           *           *           *
CAAGAAAATC  AATCACCTTA  ATGGAACAAC  AAAAGATAGC  ACAATTAATA  ATATTGCCTT
GTTCTTTTAG  TTAGTGGAAT  TACCTTGTTG  TTTTCTATCG  TGTTAATTAT  TATAACGGAA
 S  R  K  S   I  T  L    M  E  Q    Q  K  I  A   Q  L  I    I  L  P >

4750        4760        4770        4780        4790        4800
          *           *           *           *           *           *
GTAAACATGA  AGTATTAGAA  CAAGGAAAAG  TTGTAATGGA  TTCAGAGAGA  GGAGACAAAG
CATTTGTACT  TCATAATCTT  GTTCCTTTTC  AACATTACCT  AAGTCTCTCT  CCTCTGTTTC
 C  K  H  E   V  L  E    Q  G  K    V  V  M  D   S  E  R    G  D  K >

4810        4820        4830        4840        4850        4860
          *           *           *           *           *           *
GTTATGGGTC  AACAGGAGTA  TTCTCCTCTT  GGGTTGACAG  GATTGAGGAA  GCAGAAATAA
CAATACCCAG  TTGTCCTCAT  AAGAGGAGAA  CCCAACTGTC  CTAACTCCTT  CGTCTTTATT
 G  Y  G  S   T  G  V    F  S  S    W  V  D  R   I  E  E    A  E  I >

4870        4880        4890        4900        4910        4920
          *           *           *           *           *           *
ATCATGAAAA  ATTTCACTCA  GATCCACAAT  ACTTAAGGAC  TGAATTTAAT  TTACCCAAGA
TAGTACTTTT  TAAAGTGAGT  CTAGGTGTTA  TGAATTCCTG  ACTTAAATTA  AATGGGTTCT
 N  H  E  K   F  H  S    D  P  Q    Y  L  R  T   E  F  N    L  P  K >

4930        4940        4950        4960        4970        4980
          *           *           *           *           *           *
TGGTTGCAGA  AGAGATAAGA  CGAAAGTGCC  CTGTATGTAG  AATCAGAGGA  GAACAAGTGG
ACCAACGTCT  TCTCTATTCT  GCTTTCACGG  GACATACATC  TTAGTCTCCT  CTTGTTCACC
 M  V  A  E   E  I  R    R  K  C    P  V  C  R   I  R  G    E  Q  V >

4990        5000        5010        5020        5030        5040
          *           *           *           *           *           *
GAGGACAATT  GAAAATAGGG  CCTGGAATAT  GGCAAGTGGA  TTGCACACAC  TTTAATAGTA
CTCCTGTTAA  CTTTTATCCC  GGACCTTATA  CCGTTCACCT  AACGTGTGTG  AAATTATCAT
 G  G  Q  L   K  I  G    P  G  I    W  Q  V  D   C  T  H    F  N  S >

5050        5060        5070        5080        5090        5100
          *           *           *           *           *           *
AGATAATCAT  TGTAGCAGTA  CATGTGGAAT  CAGGATTTTT  ATGGGCACAG  ATAATTCCAC
TCTATTAGTA  ACATCGTCAT  GTACACCTTA  GTCCTAAAAA  TACCCGTGTC  TATTAAGGTG
 K  I  I  I   V  A  V    H  V  E    S  G  F  L   W  A  Q    I  I  P >

5110        5120        5130        5140        5150        5160
          *           *           *           *           *           *
AGGAGACTGC  AGATTGTACA  GTCAAGGCTC  TTCTGCAACT  TATATGTGCT  CATAATGTTA
TCCTCTGACG  TCTAACATGT  CAGTTCCGAG  AAGACGTTGA  ATATACACGA  GTATTACAAT
 Q  E  T  A   D  C  T    V  K  A    L  L  Q  L   I  C  A    H  N  V >

5170        5180        5190        5200        5210        5220
          *           *           *           *           *           *
CAGAATTACA  AACAGACAAT  GGACCAAATT  TTAAAAATCA  GAAAATGGAA  GGTTTATTAA
GTCTTAATGT  TTGTCTGTTA  CCTGGTTTAA  AATTTTTAGT  CTTTTACCTT  CCAAATAATT
 T  E  L  Q   T  D  N    G  P  N    F  K  N  Q   K  M  E    G  L  L >
```

FIG. 1H

```
          5230         5240         5250         5260         5270         5280
            *            *            *            *            *            *
    ATTTTATGGG   AATAAAACAT   AAATTAGGGA   TACCAGGTAA   CCCACAATCA   CAGGCATTAG
    TAAAATACCC   TTATTTTGTA   TTTAATCCCT   ATGGTCCATT   GGGTGTTAGT   GTCCGTAATC
    N  F  M  G   I  K  H      K  L  G      I  P  G  N   P  Q  S      Q  A  L >

5290         5300         5310         5320         5330         5340
            *            *            *            *            *            *
    TGGAAAATGC   TAATAACACA   TTAAAAGCTT   GGATTCAAAA   ATTCCTACCA   GAGACTACCT
    ACCTTTTACG   ATTATTGTGT   AATTTTCGAA   CCTAAGTTTT   TAAGGATGGT   CTCTGATGGA
    V  E  N  A   N  N  T      L  K  A      W  I  Q  K   F  L  P      E  T  T >

5350         5360         5370         5380         5390         5400
            *            *            *            *            *            *
    CTCTGGATAA   TGCTCTGGCC   CTAGCCCTGT   ATAGTCTCAA   CTTTAAACAA   AGGGGTAGAC
    GAGACCTATT   ACGAGACCGG   GATCGGGACA   TATCAGAGTT   GAAATTTGTT   TCCCCATCTG
    S  L  D  N   A  L  A      L  A  L      Y  S  L  N   F  K  Q      R  G  R >

5410         5420         5430         5440         5450         5460
            *            *            *            *            *            *
    TAGGAAGGAT   GGCCCCTTAT   GAATTATACA   TACAACAAGA   ATCATTAAGA   ATACAAGACT
    ATCCTTCCTA   CCGGGGAATA   CTTAATATGT   ATGTTGTTCT   TAGTAATTCT   TATGTTCTGA
    L  G  R  M   A  P  Y      E  L  Y      I  Q  Q  E   S  L  R      I  Q  D >

5470         5480         5490         5500         5510         5520
            *            *            *            *            *            *
    ATTTTTCGCA   GATTCCACAA   AAGTTAATGA   TGCAGTGGGT   GTATTACAAA   GATCAAAAAG
    TAAAAAGCGT   CTAAGGTGTT   TTCAATTACT   ACGTCACCCA   CATAATGTTT   CTAGTTTTTC
    Y  F  S  Q   I  P  Q      K  L  M      M  Q  W  V   Y  Y  K      D  Q  K >

5530         5540         5550         5560         5570         5580
            *            *            *            *            *            *
    ACAAAAAATG   GAAGGGACCA   ATGAGAGTGG   AATATTGGGG   ACAAGGATCA   GTATTATTAA
    TGTTTTTTAC   CTTCCCTGGT   TACTCTCACC   TTATAACCCC   TGTTCCTAGT   CATAATAATT
    D  K  K  W   K  G  P      M  R  V      E  Y  W  G   Q  G  S      V  L  L >

5590         5600         5610         5620         5630         5640
            *            *            *            *            *            *
    AGGATGAAGA   GAAGGGATAT   TTTCTTGTAC   CTAGGAGACA   CATAAGAAGA   GTCCCAGAAC
    TCCTACTTCT   CTTCCCTATA   AAAGAACATG   GATCCTCTGT   GTATTCTTCT   CAGGGTCTTG
    K  D  E  E   K  G  Y      F  L  V      P  R  R  H   I  R  R      V  P  E >

5650         5660         5670         5680         5690         5700
            *            *            *            *            *            *
    CCTGCACTCT   TCCTGAAGGG   GATGAGTGAC   GAAGATTGGC   AGGTAAGTAG   AAGACTCTTT
    GGACGTGAGA   AGGACTTCCC   CTACTCACTG   CTTCTAACCG   TCCATTCATC   TTCTGAGAAA
                        ORF2 →  M  S  D   E  D  W      Q  V  S      R  L  F>
    P  C  T  L   P  E  G      D  E >     ← ORF1

5710         5720         5730         5740         5750         5760
            *            *            *            *            *            *
    GCAGTGCTCC   AAGGAGGAGT   ACGTAGTGCT   ATGCTATACA   TATCTAGACT   ACCTCCGGAC
    CGTCACGAGG   TTCCTCCTCA   TGCATCACGA   TACGATATGT   ATAGATCTGA   TGGAGGCCTG
    A  V  L      Q  G  G  V   R  S  A      M  L  Y      I  S  R  L   P  P  D>

5770         5780         5790         5800         5810         5820
            *            *            *            *            *            *
    GAAAGAGAAA   GGTATAAAAA   AGACTTTAAG   AAAAGGCTTT   TGGAAAAGGA   AACAGGATTC
    CTTTCTCTTT   CCATATTTTT   TCTGAAATTC   TTTTCCGAAA   ACCTTTTCCT   TTGTCCTAAG
    E  R  E      R  Y  K  K   D  F  K      K  R  L      L  E  K  E   T  G  F>
```

FIG. 1I

```
          5830         5840         5850         5860         5870         5880
            *    *       *    *       *    *       *    *       *    *       *    *
       ATACAGAGAT   TAAGAAAAGC   GGAAGGAATA   AGGTGGAGCT   TCCATACTAG   AGATTATTAT
       TATGTCTCTA   ATTCTTTTCG   CCTTCCTTAT   TCCACCTCGA   AGGTATGATC   TCTAATAATA
        I  Q  R     L  K  A      E  G  I      R  W  S      F  H  T  R   D  Y  Y>

5890         5900         5910         5920         5930         5940
            *    *       *    *       *    *       *    *       *    *       *    *
       ATAGGATATG   TAAGAGAGAT   GGTGGCCGGA   TCTAGTCTAC   CAGATAGTTT   AAGACTGTAT
       TATCCTATAC   ATTCTCTCTA   CCACCGGCCT   AGATCAGATG   GTCTATCAAA   TTCTGACATA
        I  G  Y     V  R  E  M   V  A  G      S  S  L      P  D  S  L   R  L  Y>

5950         5960         5970         5980         5990         6000
            *    *       *    *       *    *       *    *       *    *       *    *
       ATTTATATAA   GCAATCCATT   GTGGCACTGG   TCATACCGTC   CTGGCCTGAC   AAATTTTAAT
       TAAATATATT   CGTTAGGTAA   CACCGTGACC   AGTATGGCAG   GACCGGACTG   TTTAAAATTA
        I  Y  I     S  N  P  L   W  H  W      S  Y  R      P  G  L  T   N  F  N>

6010         6020         6030         6040         6050         6060
            *    *       *    *       *    *       *    *       *    *       *    *
       ACAGAATGGC   CTTTTGTGAA   TATGTGGATA   AAGACAGGAT   TCATGTGGGA   TGATATTGAA
       TGTCTTACCG   GAAAACACTT   ATACACCTAT   TTCTGTCCTA   AGTACACCCT   ACTATAACTT
        T  E  W     P  F  V  N   M  W  I      K  T  G      F  M  W  D   D  I  E>

6070         6080         6090         6100         6110         6120
            *    *       *    *       *    *       *    *       *    *       *    *
       AGCCAGAATA   TTTGCAAAGG   AGGAGAGATT   TCACATGGAT   GGGGACCTGG   AATGGTGGGA
       TCGGTCTTAT   AAACGTTTCC   TCCTCTCTAA   AGTGTACCTA   CCCCTGGACC   TTACCACCCT
        S  Q  N     I  C  K  G   G  E  I      S  H  G      W  G  P  G   M  V  G>

6130         6140         6150         6160         6170         6180
            *    *       *    *       *    *       *    *       *    *       *    *
       ATTGTGATAA   AAGCTTTTAG   TTGTGGAGAA   AGAAAGATTG   AGGCTACTCC   TGTAATGATT
       TAACACTATT   TTCGAAAATC   AACACCTCTT   TCTTTCTAAC   TCCGATGAGG   ACATTACTAA
        I  V  I     K  A  F  S   C  G  E      R  K  I      E  A  T  P   V  M  I>

6190         6200         6210         6220         6230         6240
            *    *       *    *       *    *       *    *       *    *       *    *
       ATAAGAGGAG   AAATAGATCC   AAAAAAATGG   TGTGGAGATT   GTTGGAATTT   GATGTGTCTT
       TATTCTCCTC   TTTATCTAGG   TTTTTTTACC   ACACCTCTAA   CAACCTTAAA   CTACACAGAA
        I  R  G     E  I  D  P   K  K  W      C  G  D      C  W  N  L   M  C  L>

6250         6260         6270         6280         6290         6300
            *    *       *    *       *    *       *    *       *    *       *    *
       AGGAACTCAC   CTCCACAGAC   TTTACAAAGA   CTTGCTATGT   TGGCATGTGG   CGTGCCGGCT
       TCCTTGAGTG   GAGGTGTCTG   AAATGTTTCT   GAACGATACA   ACCGTACACC   GCACGGCCGA
        R  N  S     P  P  Q  T   L  Q  R      L  A  M      L  A  C  G   V  P  A>

6310         6320         6330         6340         6350         6360
            *    *       *    *       *    *       *    *       *    *       *    *
       AAGGAGTGGC   GAGGATGCTG   TAATCAACGC   TTTGTTTCTC   CTTACAGAAC   GCCTGCTGAT
       TTCCTCACCG   CTCCTACGAC   ATTAGTTGCG   AAACAAAGAG   GAATGTCTTG   CGGACGACTA
        K  E  W     R  G  C  C   N  Q  R      F  V  S      P  Y  R  T   P  A  D>

6370         6380         6390         6400         6410         6420
            *    *       *    *       *    *       *    *       *    *       *    *
       TTGGAGGTCA   TTCAATCCAA   GCCCAGCTGG   AGTCTATTAT   GGTCAGGGAG   CCTATGAATG
       AACCTCCAGT   AAGTTAGGTT   CGGGTCGACC   TCAGATAATA   CCAGTCCCTC   GGATACTTAC
        L  E  V     I  Q  S  K   P  S  W      S  L  L      W  S  G  S   L>  ← ORF2

6430         6440         6450         6460         6470         6480
            *    *       *    *       *    *       *    *       *    *       *    *
       GAAGACATAC   TAACATTATT   TAATAAGGTC   ACTAAGAAAC   TAGAAAGGA    AAAAGCTATC
       CTTCTGTATG   ATTGTAATAA   ATTATTCCAG   TGATTCTTTG   ATCTTTTCCT   TTTTCGATAG
```

FIG. 1J

```
              6490       6500       6510       6520       6530       6540
                *          *          *          *          *          *
           AGAATATTTG TATTAGCACA TCAATTAGAA AGGGACAAAG TTATTAGATT ACTACAAGGA
           TCTTATAAAC ATAATCGTGT AGTTAATCTT TCCCTGTTTC AATAATCTAA TGATGTTCCT 6550       6560       6570       6580       6590       6600
                *          *          *          *          *          *
           TTAGTTTGGA GACATAGATT TAAGAAACCC CAAACAAAAT ACTGTTTATG TTGGTTCTGT
           AATCAAACCT CTGTATCTAA ATTCTTTGGG GTTTGTTTTA TGACAAATAC AACCAAGACA 6610       6620       6630       6640       6650       6660
                *          *          *          *          *          *
           TGCAAATTCT ACTATTGGCA GTTGCAATCT ACATTATCAA TAACTACTGC TTAGAAATAC
           ACGTTTAAGA TGATAACCGT CAACGTTAGA TGTAATAGTT ATTGATGACG AATCTTTATG 6670       6680       6690       6700       6710       6720
                *          *          *          *          *          *
           TTATAATAAT ATTTCATTTG CAACAATAAT TATGGCAGAA GGATTTGCAG CCAATAGACA
           AATATTATTA TAAAGTAAAC GTTGTTATTA ATACCGTCTT CCTAAACGTC GGTTATCTGT
                                   ENV →     M   A   E   G   F   A   A   N   R   Q>

6730       6740       6750       6760       6770       6780
                *          *          *          *          *          *
           ATGGATAGGA CCAGAAGAAG CTGAAGAGTT ATTAGATTTT GATATAGCAA CACAAATGAA
           TACCTATCCT GGTCTTCTTC GACTTCTCAA TAATCTAAAA CTATATCGTT GTGTTTACTT
            W   I   G   P   E   E   A   E   E   L   L   D   F   D   I   A   T   Q   M   N>

6790       6800       6810       6820       6830       6840
                *          *          *          *          *          *
           TGAAGAAGGG CCACTAAATC CAGGGATGAA CCCATTTAGG GTACCTGGAA TAACAGATAA
           ACTTCTTCCC GGTGATTTAG GTCCCTACTT GGGTAAATCC CATGGACCTT ATTGTCTATT
            E   E   E   P   L   N   P   G   M   N   P   F   R   V   P   G   I   T   D   K>

6850       6860       6870       6880       6890       6900
                *          *          *          *          *          *
           AGAAAAGCAA GACTATTGTA ACATATTACA ACCTAAGTTA CAAGATTTAC GGAATGAACT
           TCTTTTCGTT CTGATAACAT TGTATAATGT TGGATTCAAT GTTCTAAATG CCTTACTTGA
            E   K   Q   D   Y   C   N   I   L   Q   P   K   L   Q   D   L   R   N   E   L>

6910       6920       6930       6940       6950       6960
                *          *          *          *          *          *
           TCAAGAGGTA AAACTAGAAG AAGGAAATGC AGGTAAGTTT AGAAGGGCAA GATATTTAAG
           AGTTCTCCAT TTTGATCTTC TTCCTTTACG TCCATTCAAA TCTTCCCGTT CTATAAATTC
            Q   E   V   K   L   E   E   G   N   A   G   K   F   R   R   A   R   Y   L   R>

6970       6980       6990       7000       7010       7020
                *          *          *          *          *          *
           ATATTCTGAT GAAAATGTGC TATCTATAGT CTATTTGCTA ATAGGATATC TAAGATATTT
           TATAAGACTA CTTTTACACG ATAGATATCA GATAAACGAT TATCCTATAG ATTCTATAAA
            Y   S   D   E   N   V   L   S   I   V   Y   L   L   I   G   Y   L   R   Y   L>

7030       7040       7050       7060       7070       7080
                *          *          *          *          *          *
           AATAAATCGT AGGAGTTTAG GATCTTTAAG ACATGATATA GACATAGAAA CACCTCAAGA
           TTATTTAGCA TCCTCAAATC CTAGAAATTC TGTACTATAT CTGTATCTTT GTGGAGTTCT
            I   N   R   R   S   L   G   S   L   R   H   D   I   D   I   E   T   P   Q   E>

7090       7100       7110       7120       7130       7140
                *          *          *          *          *          *
           GGAATATTAT AGTAATAGTG AAAGGGGTAC CACATTAAAT CAAAAATATG CGAGAAGATG
           CCTTATAATA TCATTATCAC TTTCCCCATG GTGTAATTTA GTTTTTATAC GCTCTTCTAC
            E   Y   Y   S   N   S   E   R   G   T   T   L   N   Q   K   Y   A   R   R   C>
```

FIG. 1K

```
           7150        7160        7170        7180        7190        7200
          *   *       *   *       *   *       *   *       *   *       *   *
      TTGTGTTAGC  ACACTTATTA  TGTATTTAAT  TCTTTTTGCA  GTAGGCATCT  GGTGGGGAGC
      AACACAATCG  TGTGAATAAT  ACATAAATTA  AGAAAAACGT  CATCCGTAGA  CCACCCCTCG
        C  V  S     T  L  I     M  Y  L     I  F  A     V  G  I     W  W  G  A>

7210        7220        7230        7240        7250        7260
          *   *       *   *       *   *       *   *       *   *       *   *
      TAGAGCACAA  GTAGTGTGGA  GACTTCCCCC  TTTAGTAGTT  CCAGTAGAAG  AATCAGAAAT
      ATCTCGTGTT  CATCACACCT  CTGAAGGGGG  AAATCATCAA  GGTCATCTTC  TTAGTCTTTA
        R  A  Q     V  V  W     R  L  P  P     L  V  V     P  V  E     E  S  E  I>

7270        7280        7290        7300        7310        7320
          *   *       *   *       *   *       *   *       *   *       *   *
      AATTTTTTGG  GATTGTTGGG  CACCAGAAGA  ACCCGCCTGT  CAAGACTTTC  TTGGGGCAAT
      TTAAAAAACC  CTAACAACCC  GTGGTCTTCT  TGGGCGGACA  GTTCTGAAAG  AACCCCGTTA
        I  F  W     D  C  W     A  P  E  E     P  A  C     Q  D  F     L  G  A  M>

7330        7340        7350        7360        7370        7380
          *   *       *   *       *   *       *   *       *   *       *   *
      GATACATCTA  AAAGCTAGTA  CGAATATAAG  TATACAAGAG  GGACCTACCT  TGGGGAATTG
      CTATGTAGAT  TTTCGATCAT  GCTTATATTC  ATATGTTCTC  CCTGGATGGA  ACCCCTTAAC
        I  H  L     K  A  S     T  N  I  S     I  Q  E     G  P  T     L  G  N  W>

7390        7400        7410        7420        7430        7440
          *   *       *   *       *   *       *   *       *   *       *   *
      GGCTAGAGAA  ATATGGGGAA  CATTATTCAA  AAAGGCTACC  AGACAATGTA  GAAGAGGTAG
      CCGATCTCTT  TATACCCCTT  GTAATAAGTT  TTTCCGATGG  TCTGTTACAT  CTTCTCCATC
        A  R  E     I  W  G     T  L  F  K     K  A  T     R  Q  C     R  R  G  R>

7450        7460        7470        7480        7490        7500
          *   *       *   *       *   *       *   *       *   *       *   *
      AATATGGAAA  AGATGGAATG  AAACTATAAC  AGGACCATTA  GGATGTGCTA  ATAACACATG
      TTATACCTTT  TCTACCTTAC  TTTGATATTG  TCCTGGTAAT  CCTACACGAT  TATTGTGTAC
        I  W  K     R  W  N     E  T  I  T     G  P  L     G  C  A     N  N  T  C>

7510        7520        7530        7540        7550        7560
          *   *       *   *       *   *       *   *       *   *       *   *
      TTATAATATT  TCAGTAATAG  TACCTGATTA  TCAATGTTAT  CTAGACCGAG  TAGATACTTG
      AATATTATAA  AGTCATTATC  ATGGACTAAT  AGTTACAATA  GATCTGGCTC  ATCTATGAAC
        Y  N  I     S  V  I     V  P  D  Y     Q  C  Y     L  D  R     V  D  T  W>

7570        7580        7590        7600        7610        7620
          *   *       *   *       *   *       *   *       *   *       *   *
      GTTACAAGGG  AAAGTAAATA  TATCATTATG  TCTAACAGGA  GGAAAAATGT  TGTACAATAA
      CAATGTTCCC  TTTCATTTAT  ATAGTAATAC  AGATTGTCCT  CCTTTTTACA  ACATGTTATT
        L  Q  G     K  V  N     I  S  L  C     L  T  G     K  M  L     Y  N  K>

7630        7640        7650        7660        7670        7680
          *   *       *   *       *   *       *   *       *   *       *   *
      ATATACAAAA  CAATTAAGCT  ATTGTACAGA  CCCATTACAA  ATCCCACTGA  TCAATTATAC
      TATATGTTTT  GTTAATTCGA  TAACATGTCT  GGGTAATGTT  TAGGGTGACT  AGTTAATATG
        Y  T  K     Q  L  S     Y  C  T  D     P  L  Q     I  P  L     I  N  Y  T>

7690        7700        7710        7720        7730        7740
          *   *       *   *       *   *       *   *       *   *       *   *
      ATTTGGACCT  AATCAAACAT  GTATGTGGAA  CACTTCACAA  ATTCAGGACC  CTGAGATACC
      TAAACCTGGA  TTAGTTTGTA  CATACACCTT  GTGAAGTGTT  TAAGTCCTGG  GACTCTATGG
        F  G  P     N  Q  T     C  M  W  N     T  S  Q     I  Q  D     P  E  I  P>

7750        7760        7770        7780        7790        7800
          *   *       *   *       *   *       *   *       *   *       *   *
      AAAATGTGGA  TGGTGGAATC  AAAGAGCCTA  TTATAAAAAT  TGTAAATGGG  AAAAAACAGA
      TTTTACACCT  ACCACCTTAG  TTTCTCGGAT  AATATTTTTA  ACATTTACCC  TTTTTTGTCT
        K  C  G     W  W  N     Q  R  A  Y     Y  K  N     C  K  W     E  K  T  D>
```

FIG. 1L

```
         7810       7820       7830       7840       7850       7860
           *  *       *  *       *  *       *  *       *  *       *  *
       TGTAAAGTTT CATTGTCAAA GAACACAGAG TCAGCCTGGA ACATGGCTTA GAGCAATCTC
       ACATTTCAAA GTAACAGTTT CTTGTGTCTC AGTCGGACCT TGTACCGAAT CTCGTTAGAG
        V  K  F   H  C  Q    R  T  Q  S  Q  P  G   T  W  L    R  A  I  S>

7870       7880       7890       7900       7910       7920
           *  *       *  *       *  *       *  *       *  *       *  *
       GTCATGGAGA CAAAGGAATA GATGGGAATG GAGACCAGAT TTTGAAAGTG AAAAGGTGAA
       CAGTACCTCT GTTTCCTTAT CTACCCTTAC CTCTGGTCTA AAACTTTCAC TTTTCCACTT
        S  W  R   Q  R  N    R  W  E    R  P  D    F  E  S    E  K  V  K>

7930       7940       7950       7960       7970       7980
           *  *       *  *       *  *       *  *       *  *       *  *
       AATATCTCTA AAGTGTAATA GCACAAAAAA CCTAACCTTT GCAATGAGAA GTTCAGGAGA
       TTATAGAGAT TTCACATTAT CGTGTTTTTT GGATTGGAAA CGTTACTCTT CAAGTCCTCT
        I  S  L   K  C  N    S  T  K  N  L  T  F   A  M  R    S  S  G  D>

7990       8000       8010       8020       8030       8040
           *  *       *  *       *  *       *  *       *  *       *  *
       TTATGGAGAA GTAACGGGAG CTTGGATAGA GTTTGGATGT CATAGAAATA AATCAAAACT
       AATACCTCTT CATTGCCCTC GAACCTATCT CAAACCTACA GTATCTTTAT TTAGTTTTGA
        Y  G  E   V  T  G    A  W  I  E  F  G  C   H  R  N    K  S  K  L>

8050       8060       8070       8080       8090       8100
           *  *       *  *       *  *       *  *       *  *       *  *
       TCATGATGAA GCAAGGTTTA GAATTAGATG TAGATGGAAT ATAGGGGAGA ATACCTCACT
       AGTACTACTT CGTTCCAAAT CTTAATCTAC ATCTACCTTA TATCCCCTCT TATGGAGTGA
        H  D  E   A  R  F    R  I  R  C  R  W  N   I  G  E    N  T  S  L>

8110       8120       8130       8140       8150       8160
           *  *       *  *       *  *       *  *       *  *       *  *
       CATTGATACA TGTGGAAACA CTCAAAATGT TTCAGGGGCA AATCCTGTAG ATTGTACCAT
       GTAACTATGT ACACCTTTGT GAGTTTTACA AAGTCCCCGT TTAGGACATC TAACATGGTA
        I  D  T   C  G  N    T  Q  N  V  S  G  A   N  P  V    D  C  T  M>

8170       8180       8190       8200       8210       8220
           *  *       *  *       *  *       *  *       *  *       *  *
       GTATGCAAAT AAAATGTACA ATTGTTCTTT ACAAAACGGG TTTACTATGA AGGTAGATGA
       CATACGTTTA TTTTACATGT TAACAAGAAA TGTTTTGCCC AAATGATACT TCCATCTACT
        Y  A  N   K  M  Y    N  C  S  L  Q  N  G   F  T  M    K  V  D  D>

8230       8240       8250       8260       8270       8280
           *  *       *  *       *  *       *  *       *  *       *  *
       CCTTATTATG CATTTCAATA TGACAAAAGC TGTAGAAATG TATAATATTG CTGGAAATTG
       GGAATAATAC GTAAAGTTAT ACTGTTTTCG ACATCTTTAC ATATTATAAC GACCTTTAAC
        L  I  M   H  F  N    M  T  K  A  V  E  M   Y  N  I    A  G  N  W>

8290       8300       8310       8320       8330       8340
           *  *       *  *       *  *       *  *       *  *       *  *
       GTCTTGTACA TCTGACTTGC CACCAACATG GGGGTATATG AATTGTAACT GTACAAATAA
       CAGAACATGT AGACTGAACG GTGGTTGTAC CCCCATATAC TTAACATTGA CATGTTTATT
        S  C  T   S  D  L    P  P  T  W  G  Y  M   N  C  N    C  T  N  N>

8350       8360       8370       8380       8390       8400
           *  *       *  *       *  *       *  *       *  *       *  *
       TAGTAATGAT AATACTAGAA TGGCATGTCC TAACAATCAA GGCATCTTAA GGAATTGGTA
       ATCATTACTA TTATGATCTT ACCGTACAGG ATTGTTAGTT CCGTAGAATT CCTTAACCAT
        S  N  D   N  T  R    M  A  C  P  N  N  Q   G  I  L    R  N  W  Y>

8410       8420       8430       8440       8450       8460
           *  *       *  *       *  *       *  *       *  *       *  *
       TAACCCAGTA GCAGGATTAC GACAATCCTT GGAAAAGTAT CAAGTTGTAA AACAACCAGA
       ATTGGGTCAT CGTCCTAATG CTGTTAGGAA CCTTTTCATA GTTCAACATT TTGTTGGTCT
        N  P  V   A  G  L    R  Q  S  L  E  K  Y   Q  V  V    K  Q  P  D>
```

FIG. 1M

```
              8470         8480         8490         8500         8510         8520
               *    *       *    *       *    *       *    *       *    *       *    *
          TTACTTAGTG   GTCCCAGGGG   AAGTCATGGA   ATATAAAACT   AGAAGGAAAA   GGGCAGCTAT
          AATGAATCAC   CAGGGTCCCC   TTCAGTACCT   TATATTTTGA   TCTTCCTTTT   CCCGTCGATA
            Y  L  V      V  P  G      E  V  M  E    Y  K  T      R  R  K      R  A  A  I>

8530         8540         8550         8560         8570         8580
               *    *       *    *       *    *       *    *       *    *       *    *
          TCATGTTATG   TTAGCTCTTG   CAACAGTATT   ATCTATGGCC   GGAGCAGGGA   CGGGGGCTAC
          AGTACAATAC   AATCGAGAAC   GTTGTCATAA   TAGATACCGG   CCTCGTCCCT   GCCCCCGATG
            H  V  M      L  A  L      A  T  V  L    S  M  A      G  A  G      T  G  A  T>

8590         8600         8610         8620         8630         8640
               *    *       *    *       *    *       *    *       *    *       *    *
          TGCTATAGGG   ATGGTAACAC   AATATCACCA   AGTTCTAGCA   ACCCATCAAG   AAGCTATTGA
          ACGATATCCC   TACCATTGTG   TTATAGTGGT   TCAAGATCGT   TGGGTAGTTC   TTCGATAACT
            A  I  G      M  V  T      Q  Y  H  Q    V  L  A      T  H  Q      E  A  I  E>

8650         8660         8670         8680         8690         8700
               *    *       *    *       *    *       *    *       *    *       *    *
          AAAGGTGACT   GAAGCCTTAA   AGATAAACAA   CTTGAGATTA   GTTACATTAG   AGCATCAAGT
          TTTCCACTGA   CTTCGGAATT   TCTATTTGTT   GAACTCTAAT   CAATGTAATC   TCGTAGTTCA
            K  V  T      E  A  L      K  I  N  N    L  R  L      V  T  L      E  H  Q  V>

8710         8720         8730         8740         8750         8760
               *    *       *    *       *    *       *    *       *    *       *    *
          ACTAGTAATA   GGATTAAAAG   TAGAAGCTAT   GGAAAAATTT   TTATATACAG   CTTTCGCTAT
          TGATCATTAT   CCTAATTTTC   ATCTTCGATA   CCTTTTTAAA   AATATATGTC   GAAAGCGATA
            L  V  I      G  L  K      V  E  A  M    E  K  F      L  Y  T      A  F  A  M>

8770         8780         8790         8800         8810         8820
               *    *       *    *       *    *       *    *       *    *       *    *
          GCAAGAATTA   GGATGTAATC   AAAATCAATT   CTTCTGCAAA   GTCCCTCCTG   AATTGTGGAT
          CGTTCTTAAT   CCTACATTAG   TTTTAGTTAA   GAAGACGTTT   CAGGGAGGAC   TTAACACCTA
            Q  E  L      G  C  N      Q  N  Q  F    F  C  K      V  P  P      E  L  W  M>
                       TM PEPTIDE 8830         8840         8850         8860         8870         8880
               *    *       *    *       *    *       *    *       *    *       *    *
          GAGGTATAAT   ATGTCTATAA   ATCAAACAAT   ATGGAATCAT   GGAAATATAA   CTTTGGGGGA
          CTCCATATTA   TACAGATATT   TAGTTTGTTA   TACCTTAGTA   CCTTTATATT   GAAACCCCCT
            R  Y  N      M  S  I      N  Q  T  I    W  N  H      G  N  I      T  L  G  E>

8890         8900         8910         8920         8930         8940
               *    *       *    *       *    *       *    *       *    *       *    *
          ATGGTATAAC   CAAACAAAAG   ATTTACAACA   AAAGTTTTAT   GAAATAATAA   TGGACATAGA
          TACCATATTG   GTTTGTTTTC   TAAATGTTGT   TTTCAAAATA   CTTTATTATT   ACCTGTATCT
            W  Y  N      Q  T  K      D  L  Q  Q    K  F  Y      E  I  I      M  D  I  E>

8950         8960         8970         8980         8990         9000
               *    *       *    *       *    *       *    *       *    *       *    *
          ACAAAATAAT   GTACAAGGGA   AAAAAGGGAT   ACAACAATTA   CAAAAGTGGG   AAGATTGGGT
          TGTTTTATTA   CATGTTCCCT   TTTTTCCCTA   TGTTGTTAAT   GTTTTCACCC   TTCTAACCCA
            Q  N  N      V  Q  G      K  K  G  I    Q  Q  L      Q  K  W      E  D  W  V>

9010         9020         9030         9040         9050         9060
               *    *       *    *       *    *       *    *       *    *       *    *
          AGGATGGATA   GGAAATATTC   CACAATACTT   AAAGGGACTA   TTGGGAGGTA   TCTTGGGAAT
          TCCTACCTAT   CCTTTATAAG   GTGTTATGAA   TTTCCCTGAT   AACCCTCCAT   AGAACCCTTA
            G  W  I      G  N  I      P  Q  Y  L    K  G  L      L  G  G      I  L  G  I>

9070         9080         9090         9100         9110         9120
               *    *       *    *       *    *       *    *       *    *       *    *
          AGGATTAGGA   GTGTTATTAT   TAATTTTATG   TTTACCCACA   TTGGTTGATT   GTATAAGAAA
          TCCTAATCCT   CACAATAATA   ATTAAAATAC   AAATGGGTGT   AACCAACTAA   CATATTCTTT
            G  L  G      V  L  L      L  I  L  C    L  P  T      V  L  D      C  I  R  N>
```

FIG. 1N

```
            9130       9140       9150       9160       9170       9180
              *  *       *  *       *  *       *  *       *  *       *  *
         TTGTATCCAC AAGATACTAG GATACACAGT AATTGCAATG CCTGAAGTAG AAGGAGAAGA
         AACATAGGTG TTCTATGATC CTATGTGTCA TTAACGTTAC GGACTTCATC TTCCTCTTCT
           C  I  H    K  I  L    G  Y  T    V  I  A  M  P  E  V    E  G  E  E>

9190       9200       9210       9220       9230       9240
              *  *       *  *       *  *       *  *       *  *       *  *
         AATACAACCA CAAATGGAAT TGAGGAGAAA TGGTAGGCAA TGTGGCATAT CTGAAAAAGA
         TTATGTTGGT GTTTACCTTA ACTCCTCTTT ACCATCCGTT ACACCGTATA GACTTTTTCT
           I  Q  P    Q  M  E    L  R  R  N  G  R  Q    C  G  I    S  E  K  E>

9250       9260       9270       9280       9290       9300
              *  *       *  *       *  *       *  *       *  *       *  *
         GGAGGAATGA TGAAGTATCT CAGACTTATT TTATAAGGGA GATGCTGTGC TGAGTTCTTC
         CCTCCTTACT ACTTCATAGA GTCTGAATAA AATATTCCCT CTACGACACG ACTCAAGAAG
           E  E>  ← ENV 9310       9320       9330       9340       9350       9360
              *  *       *  *       *  *       *  *       *  *       *  *
         CCTTTGAGGA AGGTATGTCA TATGAATCCA TTTCAAATCA AATTAAACTA ATAAAGTATG
         GGAAACTCCT TCCATACAGT ATACTTAGGT AAAGTTTAGT TTAATTTGAT TATTTCATAC 9370       9380       9390       9400       9410       9420
              *  *       *  *       *  *       *  *       *  *       *  *
         TATTATAAGG TAAAAAGAAA AAAAGACAAA GAAGAAGAAG AAGGAAGAAA GCCTTCAAGA
         ATAATATTCC ATTTTTCTTT TTTTCTGTTT CTTCTTCTTC TTCCTTCTTT CGGAAGTTCT 9430       9440       9450       9460       9470       9480
              *  *       *  *       *  *       *  *       *  *       *  *
         ATATGATGAC AGCTTTAGAA GATCGCTTTA GAAAGCTATT TGGCACAAAT TCTACAACGG
         TATACTACTG TCGAAATCTT CTAGCGAAAT CTTTCGATAA ACCGTGTTTA AGATGTTGCC 9490       9500       9510       9520       9530       9540
              *  *       *  *       *  *       *  *       *  *       *  *
         GAGACAGTAC AGTGGAATCT GACGATGAAC CTCCTAAAAA AGAAAAAAGG GTGGACTGGG
         CTCTGTCATG TCACCTTAGA CTGCTACTTG GAGGATTTTT TCTTTTTTCC CACCTGACCC 9550       9560       9570       9580       9590       9600
              *  *       *  *       *  *       *  *       *  *       *  *
         ATGAGTATTG GGACCCTGAA GAAATAGAAA GAATGCTTAT GGACTAGTGA CTGTTTACGA
         TACTCATAAC CCTGGGACTT CTTTATCTTT CTTACGAATA CCTGATCACT GACAAATGCT 9610       9620       9630       9640       9650       9660
              *  *       *  *       *  *       *  *       *  *       *  *
         ACAAATGATA AATGATGGAA ACAGCTGAGC ATGACTCATA GTTAAAGCGC TAGCAGCTGC
         TGTTTACTAT TTACTACCTT TGTCGACTCG TACTGAGTAT CAATTTCGCG ATCGTCGACG 9670       9680       9690       9700       9710       9720
              *  *       *  *       *  *       *  *       *  *       *  *
         TTAACCGCAA AACCACATCC TATGTAAAGC TTGCTGATGA CGTATAATTT GCTCCACTGT
         AATTGGCGTT TTGGTGTAGG ATACATTTCG AACGACTACT GCATATTAAA CGAGGTGACA 9730       9740       9750       9760       9770       9780
              *  *       *  *       *  *       *  *       *  *       *  *
         AAAAGTATAT AACCAGTGCT TTGTGAGACT TCGGGGAGTC TCTCCGTTGA GGACTTTCGA
         TTTTCATATA TTGGTCACGA AACACTCTGA AGCCCCTCAG AGAGGCAACT CCTGAAAGCT 9790       9800       9810       9820       9830       9840
              *  *       *  *       *  *       *  *       *  *       *  *
         GTTCTCCCTT GAGGCTCCCA CAGATACAAT AAATATTTGA GATTGAACCC TGTCAAGTAT
         CAAGAGGGAA CTCCGAGGGT GTCTATGTTA TTTATAAACT CTAACTTGGG ACAGTTCATA 9850       9860       9870       9880       9890
              *  *       *  *       *  *       *  *       *  *
         CTGTGTAATC TTTTTTACCT GTGAGGTCTC GGAATCCGGG CCGAGAACTT CGCA
         GACACATTAG AAAAAATGGA CACTCCAGAG CCTTAGGCCC GGCTCTTGAA GCGT
```

FIG. 10

Alignment of Gag Open Reading Frames of FIV Strains

FIG. 2B

```
FIV-NCSU g         70         80         90        100        110        120
                    *          *          *          *          *          *
              RLVICDLQER REKFGSSKEI DMAIVTLKVF AVVGLLNMTV STAAAENMY TQMGLDTRPS

1. FIV PPR    ---------- ---------- ---------- ---------- --------- ---------- 120
   [2141]

2. FIV Z1     ---------- ---------- ....T..... ---------- --------- ---------- 120 >
   [2138]

3. FIV CG     ---------- ---------- ---------- .....A.... .......S. ---------- 120 >
   [2136]

4. FIV 14     ---------- ---------- ---------- .....A.... .......S. ---------- 120 >
   [2132]

5. FIV TM1    .S.I...... ...D..HY.. ....T..... .....A.I.. ...T...S. ---------- 120 >
   [2012]

6. FIV TM2    .S.I...... ...D..HY.. ....T..... .....A.I.. ...T...A. ---------- 120 >
   [2012]
```

FIG. 2C

```
FIV-NCSU g    130       140       150       160       170       180
              *         *         *         *         *         *
              MREAGGKEES PPQASPIQTA NGAPQYVALD PKMVSIFMEK AREGLGGEEV QLWFTAFSAN
1. FIV PPR    ------G--- ----Y----- ---------- ---------- ---------- ---------- 180
   [2141]     TK........ .......... .......... .......... .......... .......... >
2. FIV Z1     ------G--- ----Y---V- ---V------ ---------- ---------- ---------- 180
   [2138]     .K........ .......... .......... .......... .......... .......... >
3. FIV CG     ------G--- ----Y---V- ---V------ ---------- ---------- ---------- 180
   [2136]     .K........ .......... .......... .......... .......... .......... >
4. FIV 14     ------G--- ----Y---V- ---V------ ---------- ---------- ---------- 180
   [2132]     .K........ .......... .......... .......... .......... .......... >
5. FIV TM1    ------G--- ----Y---V- ---V------ ---------- ---------- ---------- 180
   [2012]     VK.S...... .......... .......... .......... .......... .......... >
6. FIV TM2    ------G--- ----Y---V- ---V------ ---------- ---------- ---------- 180
   [2012]     VK.S...... .......... .......... .......... .......... .......... >
```

FIG. 2D

| FIV-NCSU g | 190<br>* | | 200<br>* | | 210<br>* | | 220<br>* | | 230<br>* | | 240<br>* | |
|---|---|---|---|---|---|---|---|---|---|---|---|---|
| | LTPTDMATLI | MAAPGCAADK | EILDESLKQL | TAEYDRTHPP | DGPRPLPYFT | AAEIMGIGLT | |
| 1. FIV PPR [2141] | — | — | — | — | — | — | 240 |
| 2. FIV Z1 [2138] | . . . . . . . . . . | . . . . . . . . . . | . . . . . . . . . . | . . . . . . . . N . | . . . . . . . . . . | . . . . . . . . . . | 240 > |
| 3. FIV CG [2136] | . . . . . . . . . . | . . . . . . . . . . | . . . . . . . . . . | . . . . . . . . . A | . . . . . . . . . . | . . . . . . . . . . | 240 > |
| 4. FIV 14 [2132] | . . . . . . . . . . | . . . . . . . . . . | . . . . . . . . . . | . . . . . . . . . A | . . . . . . . . . . | . . . . . . . . . . | 240 > |
| 5. FIV TM1 [2012] | . . S . . . . . . . | . . . . . . . . . S | . . . . . . . . T . | . . . . . . . . . A | . . . . . . . . . . | . . . . . . . . . . | 240 > |
| 6. FIV TM2 [2012] | . . S . . . . . . . | . . . . . . . . . S | . . . . . . . . T M | . . . . . . . . . . | . . . . . . . . . . | . . . . . . . . . . | 240 > |

FIG. 2E

| FIV-NCSU g | 250<br>* QEQQAEARFA | PARMQCRAWY | 260<br>* | LEALGKLAAI | 270<br>* | KAKSPRAVQL | 280<br>* | RQGAKEDYSS | 290<br>* | FIDRLFAQID | 300<br>* |
|---|---|---|---|---|---|---|---|---|---|---|---|
| 1. FIV PPR [2141] | — | — | — | — | — | — | — | — | — | — | — 300 > |
| 2. FIV Z1 [2138] | — | — | — | — | — | — | — | — | — | — | — 300 > |
| 3. FIV CG [2136] | — | — | — | — | — | — | — | — | — | — | — 300 > |
| 4. FIV 14 [2132] | — | — | — | — | — | — | — | — | — | — | — 300 > |
| 5. FIV TM1 [2012] | ....P.... | — | — | — | — | — | ......K.. | — | — | — | — 300 > |
| 6. FIV TM2 [2012] | ....P.... | — | — | — | — | — | ......K.. | — | — | — | — 300 > |

FIG. 2F

```
FIV-NCSU g    310        320        330        340        350        360
              *          *          *          *          *          *
              QEQNTAEVKL YLKQSLSMAN ANAECKKAMS HLKPESTLEE KLRACQEVGS PGYKMQLLAE

1. FIV PPR    ---------- ---------- ---------- ---------- ---------- ---------- 360
   [2141]     .......... .......... .......... .......... .......... ..........

2. FIV Z1     ---------- -----I---- -----D---- ---------- ------I--- ---------- 360 >
   [2138]     .......... .......... .......... .......... .......... ..........

3. FIV CG     ---------- -----I---- -----D---- ---------- ------I--- ---------- 360
   [2136]     .......... .......... .......... .......... .......... ..........

4. FIV 14     ---------- -----I---- -----D---- ---------- ------I--- ---------- 360 >
   [2132]     .......... .......... .......... .......... .......... ..........

5. FIV TM1    ---------- -----I---- ..PD..R--- ---------- ------I--- ---------- 360
   [2012]     .......... .......... .......... .......... .......... ..........

6. FIV TM2    ---------- -----I---- ..PD..R--- ---------- ------I--- ---------- 360 >
   [2012]     .......... .......... .......... .......... .......... ..........
```

FIG. 2G

```
              370        380        390        400        410        420
               *          *          *          *          *          *
FIV-NCSU g   ALTKVQVVQS KGSGPVCFNC KKPGHLAKQC RDVKKCNKCG KPGHLAAKCW QGGKKNSGNW
1. FIV PPR   ---------- ---------- ------R--- ---------- ---------- ------R---
   [2141]                                                                    420>
2. FIV Z1    ------T--- ---------- ------R--- ------E--- --------N- -----NR---
   [2138]                                                                    420>
3. FIV CG    ---------- ---------- ------R--- ------E--- --------N- -----NR---
   [2136]                                                                    420>
4. FIV 14    ------T--- ---------- ------R--- ------E--- ------V-N- -----NR---
   [2132]                                                                    420>
5. FIV TM1   ..R...T... ...PRL.... ...R..KEA. R......N.. .........N .....R.T..
   [2012]                                                                    420 E>
6. FIV TM2   ..R...T... ...PRL.... ...R..KEA. R......N.. .........N .....R.T..
   [2012]                                                                    420 E>
```

FIG. 2H

```
FIV-NCSU g      430              440              450
                 *                *                *
             KAGRAAAPVN       QVQQAVMPSA      PPMEERLLDL
 1. FIV PPR     |                |                |
    [2141]      |                |                |
             . . . . . . . . . T . . . . . . . . . K . . . . >
 2. FIV Z1      |                |                |
    [2138]      |                |                |
             . . . . . . . . . . . . . . . . . . . K . . . . >
 3. FIV CG      |                |                |
    [2136]      |                |                |
             . . . . . . . . . . M . . . . . . . . K . . . . >
 4. FIV 14      |                |                |
    [2132]      |                |                |
             . . . . . . . . . . M . . . . . . . . K . . . . >
 5. FIV TM1     |                |                |
    [2012]      |                |                |
             . V . . . . . . . . . . . - I V . . . . . . . K . . . . >
 6. FIV TM2     |                |                |
    [2012]      |                |                |
             . V . . . . . . . . . . . - I V . . . . . . . K . . . . >
```

FIG. 3A

Alignment of Whole Envelope Protein Sequence

```
                     10         20         30         40         50         60
env-NCSU    *    *    *    *    *    *    *    *    *    *    *    *
            MAEGFAANRQ WIGPEEAEEL LDFDIATQMN EEGPLNPGMN PFRVPGITDK EKQDYCNILQ 1. FIV 14   ---------- ---------- ---------- ---------- ---------- ---------->
   [4221]                    L              S                                    60

2. FIV Z1   ---------- ---------- ---------- ---------- ---------- ---------->
   [4202]                                   S          V          E          N   60

3. FIV CG   ---------- ---------- ---------- ---------- ---------- ---------->
   [4187]                                   S          V          E          N   60

4. fiv19k   ---------- ---------- ---------- ---------- ---------- ---------->
   [4168]        V..G                        L          V          E          N   60

5. FIV PPR  ---------- ---------- ---------- ---------- ---------- ---------->
   [4102]                    K                         V    AV.EA D..Q     E..T  E..K  60
```

FIG. 3C

```
env-NCSU 2
         *    130     *           *    140     *           *    150     *           *    160     *           *    170     *           *    180
         HDIDIETPQE   EYYSNSERGT   TLNQKYARRC   CVSTLIMYLI   LFAVGIWWGA   RAQVWRLPP
1. FIV 14
   [4221]  ....A.....  ....C.N.R.K  ...D.I...G.  .LG.VTL....  I...........  ..........>
                                                             --  Q  --
2. FIV Z1
   [4202]  ....A.....  ....N.R.K..  ...D.I...G.  .LG.VTL....  I...G.IVYST.  G.........>
                                                             --  Q  --
3. FIV CG
   [4187]  ....A.....  ....C.N.R.K  ...D.I...G.  .LG.VTL....  T...G.IVYST.  G.........>
                                                             --  Q  --
4. fiv19k
   [4168]  ....A.....  ....N.K.K.M.D.V..GK.  .L.G.AAF....  AI..G.II.IRTVD  ..........>
                                                             --  T  --
5. FIV PPR
   [4102]  ...N.A....  ...Q..SR.Q.  ...E.I...G.  .LIG.ASL.L..  I...G.A.YL.TN  ..I.......>
```

FIG. 3D

```
env-NCSU2        190        200        210        220        230        240
                  *          *          *          *          *          *
              LVVPVEESEI IFWDCWAPEE PACQDFLGAM IHLKASTNIS IQEGPTLGNW AREIWGTLFK 1. FIV 14     ..........  ..........  ..........  ..........  ..........  .........>
   [4221]
2. FIV Z1     ..........  ........D.  ..........  ....K.....  .........R  ......A..>
   [4202]
3. FIV CG     ..........  ..........  ..........  ....K.....  .........R  ......A..>
   [4187]
4. fiv19k     ..........  ..........  ..........  ....K.....  .........R  ......A..>
   [4168]
5. FIV PPR    ..........  ..........  ..........  ..........  ..........  ......A..>
   [4102]
```

FIG. 3G

```
env-NCSU 2        YKNCKWEKTD VKFHCQRTQS QPGTWLRAIS SWRQRNRWEW RPDFESEKVK ISLKCNSTKN
                      370        380        390        400        410        420
                       *          *          *          *          *          *
1. FIV 14         ------|---EAK ---------- ........S.F ----K----- ---------- ---------->
   [4221]         .NS...
2. FIV Z1         ------|---EAK .........Q ........S.R ----K----- .......K.. .......Q..>
   [4202]         .NR...                                                              K
3. FIV CG         ------|---EAK ---------- ........S.F ----K----- .......L.. .......Q..>
   [4187]         .NS...
4. fiv19k         ------|....Q. .........Q ........S.I ----K----- ......K.K. .......P..>
   [4168]         .NQ.S.
5. FIV PPR        ------|...SN. ........Y. ........I.T ----K----- .......R.V .Q.....Q..>
   [4102]         .NS.R.                                                              H
```

FIG. 3H

```
env-NCSU2        430        440        450        460        470        480
                  *          *          *          *          *          *
              LTFAMRSSGD YGEVTGAWIE FGCHRNKSKL HDEARFRIRC RWNIGENTSL IDTCGNTQNV
1. FIV 14     ---------- ---------- ---------- ---------- ---------- ----------  480 >
   [4221]     .......... .......... .......... .......... .......... ..........
2. FIV Z1     ---------- ---------- ---------- ----A..... ...V..S... ....K.....  480 >
   [4202]     .......... .......... .......... .......... .......... ..........
3. FIV CG     ---------- ---------- .....H.... ...H.S.... ...V..S... .......D..  480 >
   [4187]     .......... .......... .......... .......... .......... ..........
4. fiv19k     ---------- ....I..... ....N..... ....T..... ...V..SD.. .....P....  480 >
   [4168]     .......... .......... .......... .......... .......... ..........
5. FIV PPR    ---------- ....M..... ..RF.T.... .......... ...E.N.N.. ....K.....  480 >
   [4102]     .......... .......... .......... .......... ...V..D... KNL.......
```

FIG. 31

```
env-NCSU 2   490       500        510        520        530        540
              *    *    *    *    *    *    *    *    *    *    *    *
           SGANPVDCTM YANKMYNCSL QNGFTMKVDD LIMHFNMTKA VEMYNIAGNW SCTSDLPPTW
1. FIV 14  ---------- .....S.... .......... .......... .......... ----------
   [4221]                                                                    540 —>
2. FIV Z1  ---------- .....S.... .......... ...V.S.... .......... ----------..SS—>
   [4202]                                                                    540
3. FIV CG  ---------- .....S.... .......... .......V.. .......K.. ----------..SS—>
   [4187]                                                                    540
4. fiv19k  ---------- ......R... ........D. .......... .......... ------M...SS—>
   [4168]                                                                    540
5. FIV PPR ---------- .......... .......... .......... .......... ------K...TN—>
   [4102]                                                                    540 QN—>
```

FIG. 3K

```
env-NCSU2   YKTRRKRAAI  HVMLALATVL  SMAGAGTGAT  AIGMVTQYHQ  VLATHQEAIE  KVTEALKINN
                 610         620         630         640         650         660
                  *           *           *           *           *           *
1. FIV 14    ---------- ---------- ---------- ---------- ---------- ----------
   [4221]    ..P.......  ..........  ..........  ..........  ..........  ..........
2. FIV Z1    ---------- ---------- ---------- ---------- -----V---- ----------  660 >
   [4202]    ..P.......  ....A..... ........I. ..........  ..........  ..........
3. FIV CG    ---------- ---------- ---------- ---------- ---------- ----------  660 >
   [4187]    ..P.......  ..........  ........I. ..........  ..........  ....G.....
4. fiv19k    ---------- ---------- ---------- ---------- ---------- ----------  660 >
   [4168]    ..P.......  ..........  ........I. ..........  ..........  ..........
5. FIV PPR   ---------- ---------- ---------- ---------- --LD--I--- ----------  660 >
   [4102]    ..YKQ.....  ......I... ........I. .......Q.. ..........  ..........
```

FIG. 3L

```
                    670        680        690        700        710        720
env-NCSU 2       *    *     *    *     *    *     *    *     *    *     *    *
             LRLVTLEHQV LVIGLKVEAM EKFLYTAFAM QELGCNQNQF FCKVPPELWM RYNMSINQTI
1. FIV 14                                                                 720
[ 4221 ]     ...........................................I.....T....T.....>
2. FIV Z1                                                                 720
[ 4202 ]     ...........................................I..G..T....T.....>
3. FIV CG                                                                 720
[ 4187 ]     ...........................................I.L...T....T.....>
4. fiv19k                                                                 720
[ 4168 ]     ...................I.........................L...R....T.....>
5. FIV PPR                                                                720
[ 4102 ]     .........M.........I......................EI.K...L....TL....>
```

FIG. 3M

```
env-NCSU 2    730        740        750        760        770        780
              *     *    *     *    *     *    *     *    *     *    *     *
              WNHGNITLGE WYNQTKDLQQ KFYEIIMDIE QNNVQGKKGI QQLQKWEDWV GWIGNIPQYL 1. FIV 14     ---------- ---------- ---------- ---------- ---------- ----------  >
   [4221]

2. FIV Z1     ---------- ....K..... ---------- ....T..... ---------- ....780...  >
   [4202]

3. FIV CG     ---------- ---------- ---------- ....T..... ---------- ....780...  >
   [4187]

4. fiv19k     ---------- .....H.... ---------- .....L.... .........R ....780...  >
   [4168]

5. FIV PPR    ....Y..... ---------- ---------- Q.L.K.N.Q. ........M. K...780...  >
   [4102]
```

FIG. 3N

| env-NCSU 2 | 790<br>*<br>KGLLGGILGI | 800<br>*<br>GLGVLLLILC | 810<br>*<br>LPTLVDCIRN | 820<br>*<br>CIHKILGYTV | 830<br>*<br>IAMPEVEGEE | 840<br>*<br>IQPQMELRRN |
|---|---|---|---|---|---|---|
| 1. FIV 14 [4221] | .......... | .......... | .......... | .......... | .......... | ........-> |
| 2. FIV Z1 [4202] | .......... | .......... | .......... | .......... | .......... | ........-> |
| 3. FIV CG [4187] | .......... | ....I..... | .......... | .......... | .......... | ........-> |
| 4. fiv19k [4168] | .......... | ....I..... | .......... | .......... | ....D.DE.. | ........-> |
| 5. FIV PPR [4102] | .......... | .......... | .......... | ..S.V..... | .IDD.ETV.. | ......K..> |

FIG. 3O

```
env-NCSU 2            850
                 *     *
              GRQCGISEKE EE 1. FIV 14            |
  [ 4221 ]           |
            . . . . . M . . . . . . >

2. FIV Z1            |
  [ 4202 ]           |
            . . . . . M . . . . . . >

3. FIV CG            |
  [ 4187 ]           |
            . . . . . M . . . . . . >

4. fiv19k            |
  [ 4168 ]           |
            . . . . . M . . . . . . >

5. FIV PPR           |
  [ 4102 ]           |
            . . . . . M . . . . . . >
```

NUCLEIC ACIDS OBTAINED FROM THE ENVELOPE CODING REGION OF FELINE IMMUNODEFICIENCY VIRUS MOLECULAR CLONE DESIGNATED JSY3

This invention was made with government support under Public Health Service grant NO1 AI 35515 from the NIAIDS-DAIDS. The government may have certain rights to this invention.

FIELD OF THE INVENTION

This invention concerns a Feline Immunodeficiency Virus molecular clone which is highly infectious in vivo and which produces immunodeficiency in infected subjects.

BACKGROUND OF THE INVENTION

Feline immunodeficiency virus (FIV), a lentivirus of cats, is associated with feline acquired immunodeficiency syndrome (AIDS). See N. Pedersen et al., *Science* 235: 790 (1987). Disorders associated with FIV infection include chronic gingivitis/stomatitis, chronic upper respiratory infections, chronic enteritis, and recurrent ocular disease. See R. English et al., *J. Am. Vet. Med. Assoc.* 196:1116 (1990); N. Pedersen et al., *Vet. Immunol. Immunopathol.* 21:111 (1989); J. Yamamoto et al., *J. Am. Vet. Med. Assoc.* 194: 213 (1989). What is known to date of the pathogenesis of FIV infection suggests that it is a valuable animal model for other retroviral diseases, such as human immunodeficiency virus-1 (HIV-1) infection. HIV-1 and FIV belong to the lentivirus subfamily of retroviruses, have similar morphology, protein composition, and $Mg^{2+}$-dependency of their reverse transcriptases (RT). See N. Pedersen et al., *Science* 235:790 (1987); N. Pedersen et al., *Vet. Immunol. Immunopathol.* 21:111 (1989). They both display tropism for T lymphocytes and monocytes and are capable of inducing these cells to form syncytia. See D. Brunner and N. Pedersen, *J. Virol.* 63: 5483 (1989); M. Gardner and P. Luciw, *FASEB Journal* 3: 2593 (1989). HIV-1 displays a particular tropism for $CD4^+$ lymphocytes, which leads to their gradual depletion and an inversion of the $CD4^+:CD8^+$ ratio. See A. Dalgleish et al., *Nature* 312: 763 (1984). The pathogenesis of HIV-1 infection has been attributed to virus-induced reduction of $CD4^+$ lymphocyte numbers and functions, resulting in decreased immune responsiveness and subsequent severe secondary infections. See M. McChesney and M. Oldstone, *Ad. Immunol.* 45: 335 (1989).

Yamamoto et al. studied the early events in the pathogenesis of FIV in kittens. See J. Yamamoto et al., *Am. J. Vet. Res.* 49: 1246 (1988). These kittens developed an acute infection syndrome similar to that seen in HIV-1, including low grade fever and transient generalized lymphadenopathy. More recent studies by Ackley et al., *J. Virol.* 64: 5652 (1990), utilized monoclonal antibodies directed against feline $CD4^+$ and $CD8^+$ homologues and Pan T cells to analyze lymphocyte profiles in SPF cats experimentally infected with FIV. These authors reported that a significant inversion of the $CD4^+:CD8^+$ ratios occurred only in cats infected for 18 months or more. The inversion was associated with a decrease in absolute number of $CD4^+$ cells and an increase in $CD8^+$ cells.

A panel of monoclonal antibodies specific for feline T cell subsets (M. Tompkins et al., *Vet. Immunol. Immunopathol.* 26: 305 (1990)) has been used to analyze T cell numbers and profiles in cats naturally infected with FIV. See C. Novotney et al., *AIDS* 4: 1213 (1990). Similar to the observation of Ackley et al. supra, cats naturally infected with FIV have an inverted $CD4^+:CD8^+$ ratio characterized by a selective reduction in $CD4^+$ cells.

SUMMARY OF THE INVENTION

A first aspect of the present invention is an isolated feline immunodeficiency virus (FIV) having all of the identifying characteristics of FIV clone JSY3.

A further aspect of the present invention is an isolated feline immunodeficiency virus (FIV) whose proviral DNA comprises a DNA sequence selected from SEQ ID NO:1 and sequences which vary from SEQ ID NO:1 due to the degeneracy of the genetic code.

A further aspect of the present invention is a biologically pure culture of host cells containing feline immunodeficiency virus as described above.

A further aspect of the present invention is isolated DNA comprising a DNA sequence selected from SEQ ID NO:1 and sequences which vary from SEQ ID NO:1 due to the degeneracy of the genetic code; vectors containing such DNA; and host cells containing and capable of expressing such vectors.

A further aspect of the present invention is isolated DNA comprising a DNA sequence selected from (a) SEQ ID NO:4, SEQ ID NO:5, SEQ ID NO:7, SEQ ID NO:9, SEQ ID NO:11, SEQ ID NO:13, SEQ ID NO:14, SEQ ID NO:16, SEQ ID NO:18, SEQ ID NO:19, and (b) sequences which vary from those of (a) above due to the degeneracy of the genetic code; vectors containing such DNA; and host cells containing and capable of expressing such vectors.

A further aspect of the present invention is a polypeptide having a sequence selected from SEQ ID NO:2, SEQ ID NO:3, SEQ ID NO:6, SEQ ID NO:8, SEQ ID NO:10, SEQ ID NO:12, SEQ ID NO:15, SEQ ID NO:17, and SEQ ID NO:20.

A further aspect of the present invention is a specific pathogen free (SPF) cat infected with feline immunodeficiency virus clone JSY3.

BRIEF DESCRIPTION OF THE DRAWINGS

FIGS. 1A–1O provide the DNA sequence of the FIV-$NCSU_1$ insert of the lambda clone. The first three nucleotides are part of the lambda vector DNA sequence; the FIV proviral DNA sequence begins with the fourth nucleotide of FIG. 1A. The gag region (and the p15, p25, p24a and p10 regions therein), the pol region (and two open reading frames (orf) therein, and the env region (and the transmembrane (TM) protein therein) are indicated.

FIGS. 2A–2H aligns the group specific antigen (gag) open reading frame of the FIV $NCSU_1$ JSY3 molecular clone with those of six known FIV strains: FIV PPR, FIV Z1, FIV CG, FIV 14, FIV TM1 and FIV TM2.

DETAILED DESCRIPTION OF THE INVENTION

Figures 2, 2A:
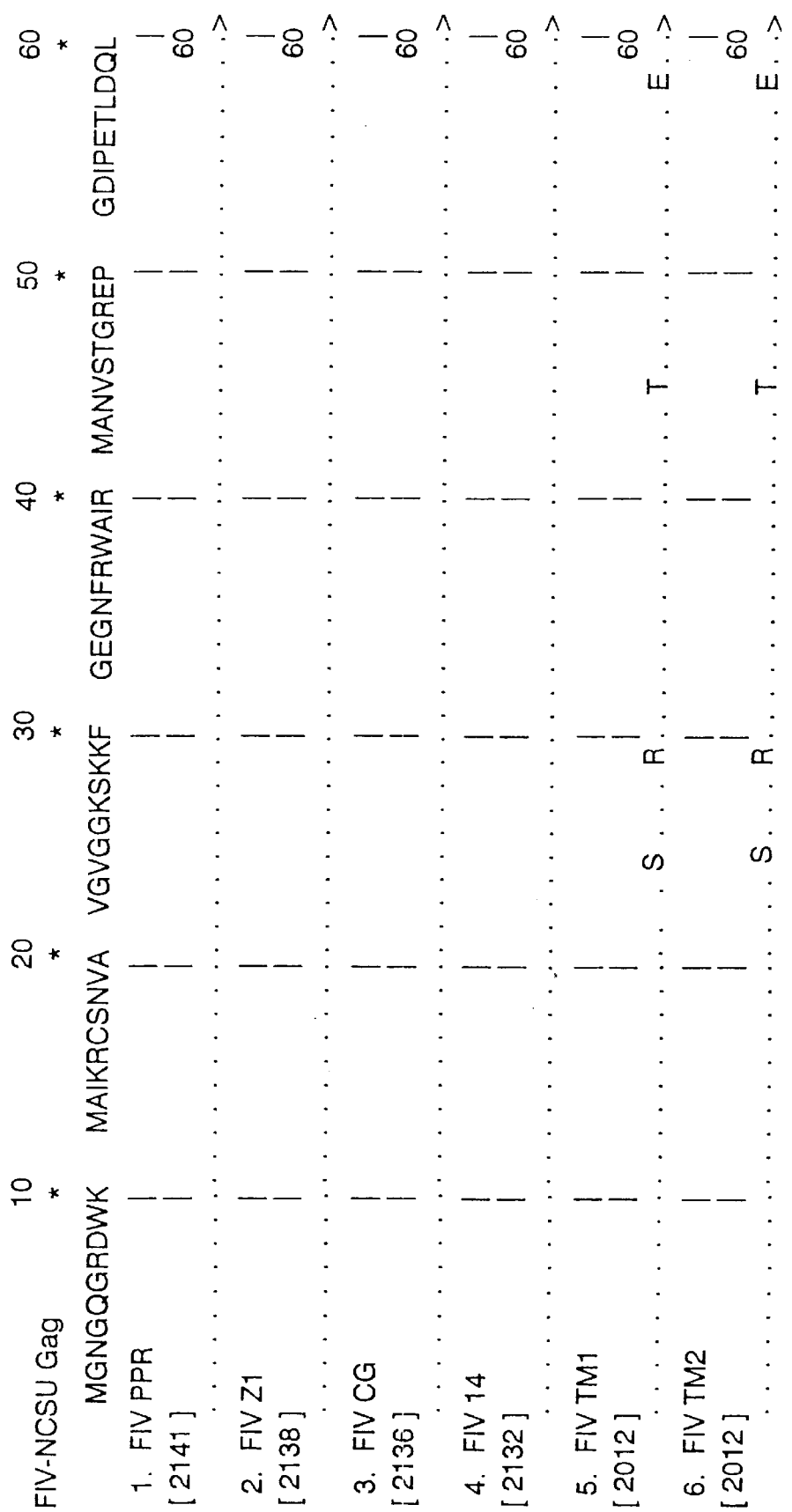
Figure 3B:
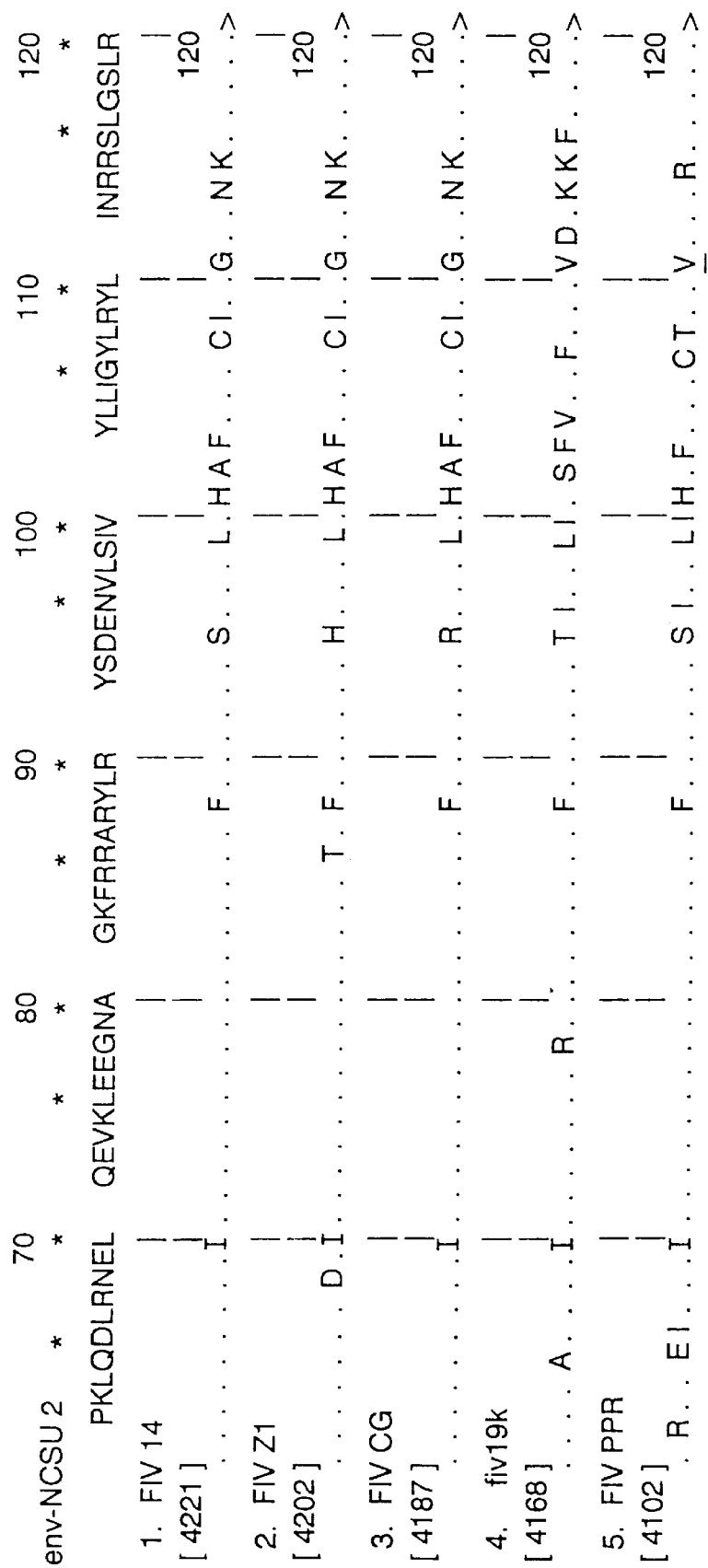
FIGS. 3A–3O aligns the envelope protein sequence of FIV $NCSU_1$ JSY3 molecular clone with those of five known FIV strains: FIV 14, FIV Z1, FIV CG, FIV 19k, and FIV PPR.
Figure 3E:
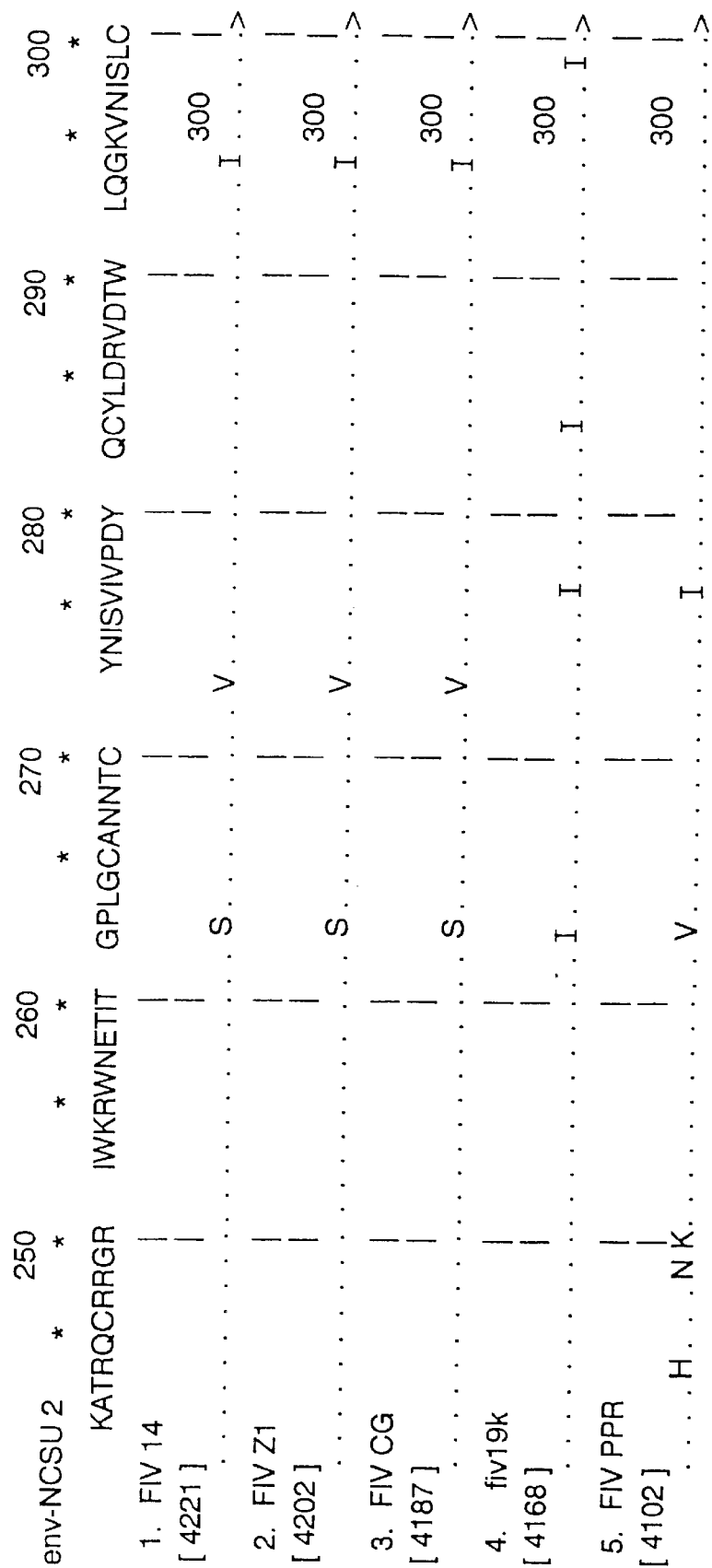
Figure 3F:
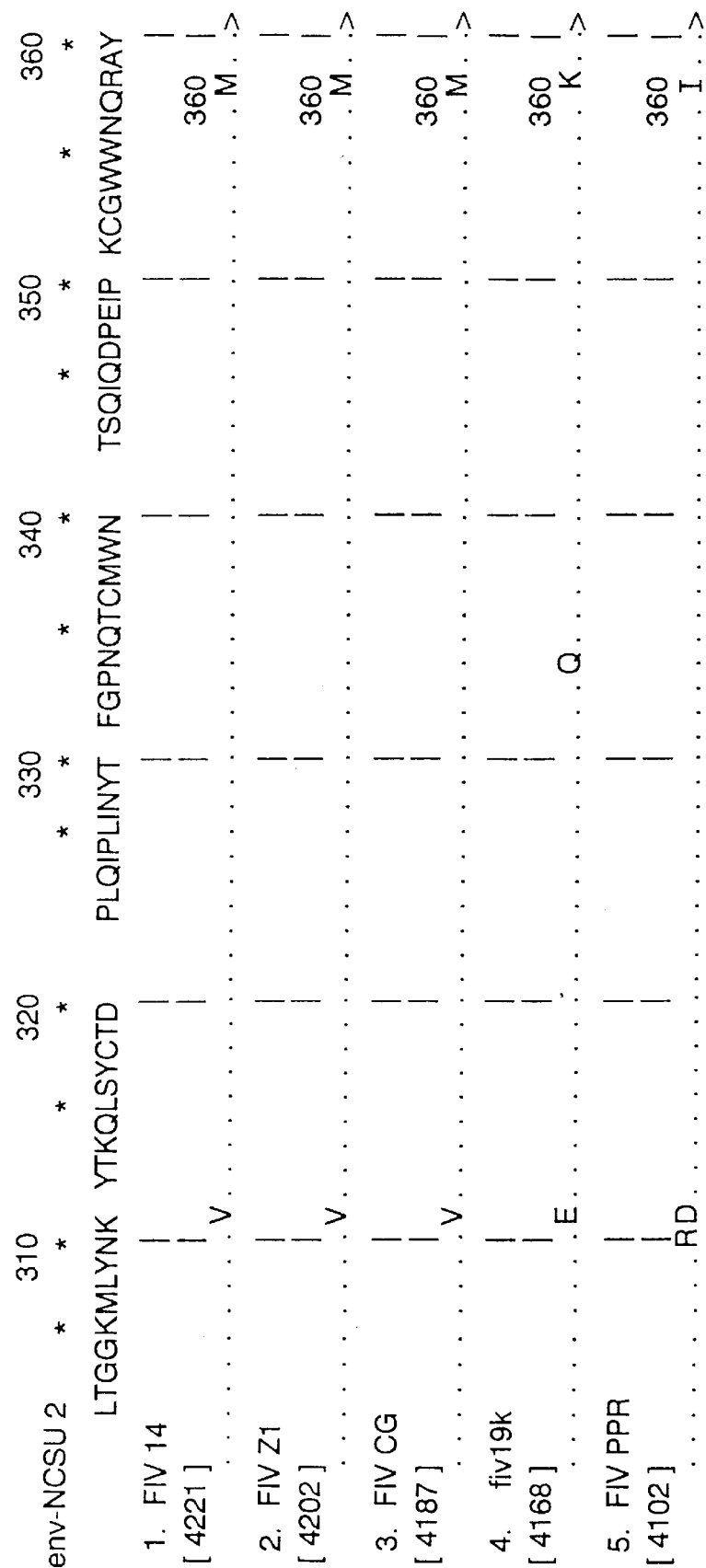
Figure 3J:
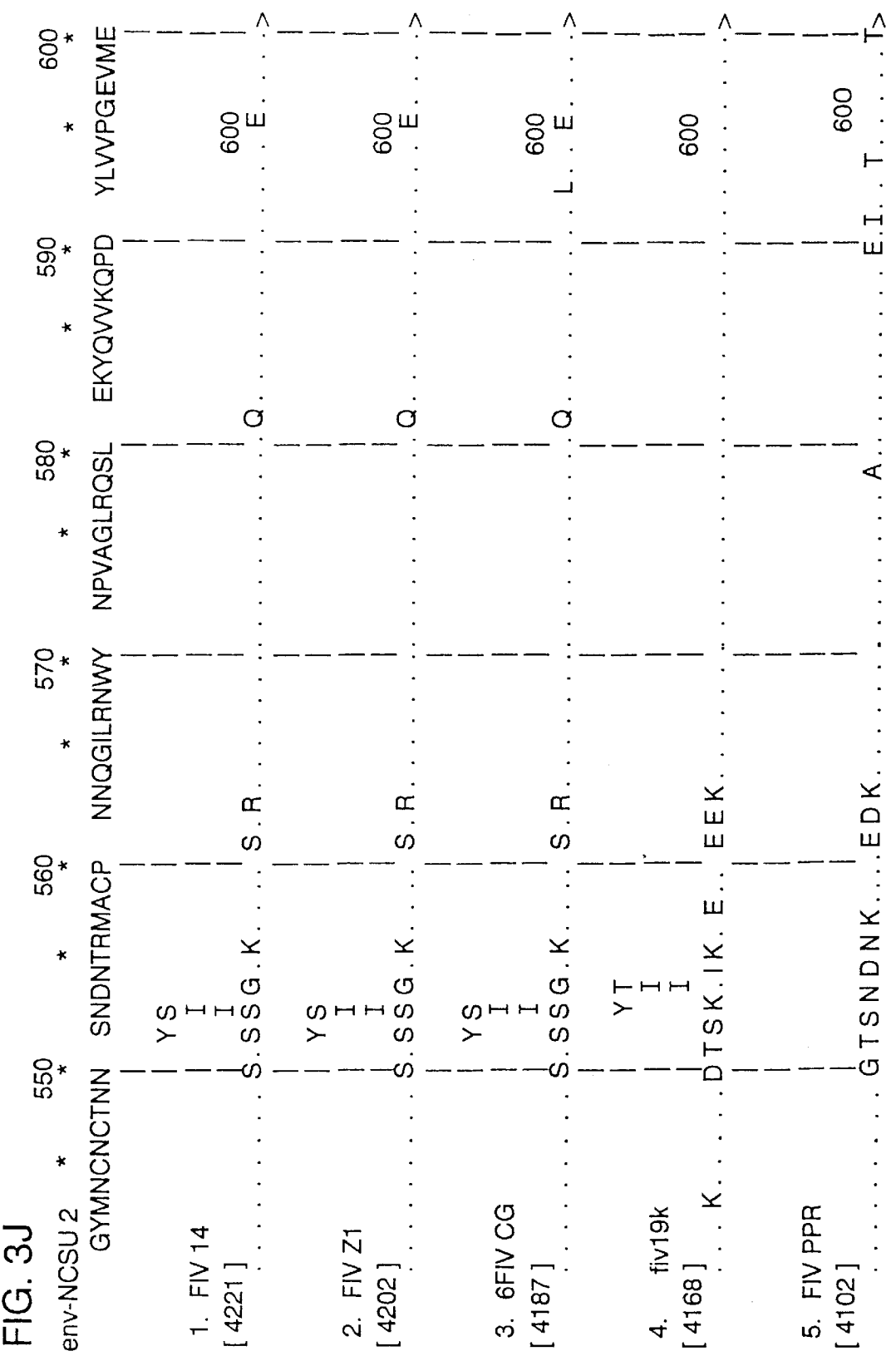

A major limitation of the FIV model for the study of retroviral infection is the unavailability of molecular clones that retain the pathogenic characteristics of the wild-type viruses. Genetically homogeneous molecular clones of FIV that retain the biological and disease-causing properties of the pathogenic wild-type populations are useful for understanding the molecular basis for determinants of FIV pathogenesis, treatment of FIV, and the relevance of FIV to other retroviral infections.

The FIV molecular clones FIV-14 (Olmsted et al., PNAS USA 86:2448 (1989)), FIV-pF34 of FIV-Petaluma (Sparger et al., *Virology* 205:546 (1994)), FIV-pPPR of FIV-PPR (Sparger et al., *Virology* 205:546 (1994)), pFTM191CG of FIV-TM1 (Miyazawa et al., *J. Virol.* 65:1572 (1991)), and 19K1 of FIV Amsterdam-19 (Siebelink et al., *J. Virol.* 66:1091 (1992)), have been reported to be infectious in vivo as determined by seroconversion, cell-associated virus, and the presence of FIV provirus. No clone has been reported as pathogenic to the extent that it causes immunodeficiency and increased susceptibility to secondary opportunistic infections.

An isolate of FIV (FIV-NCSU$_1$) that is pathogenic in vivo, as measured by a severe loss of CD4+ cells and development of secondary infections, severe wasting, neurological disease, and B-cell lymphomas, has been described recently (English et al., *J. Infect. Dis.* 170:543 (1994)). Davidson et al. (*Am. J. Pathol.* 143:1486 (1993)) were able to demonstrate that FIV-NCSU$_1$ causes a relatively early and profound state of immunodeficiency, as measured by loss of resistance to challenge with a *Toxoplasma gondii* strain with a low level of virulence. This dual FIV-*T. gondii* infection provides a model with which to determine the ability of FIV isolates as well as molecular clones of FIV to cause immunodeficiency.

A full length FIV-NCSU$_1$ genome (JSY3) was cloned directly from FIV-NCSU$_1$ infected feline CD4+ lymphocyte (FCD4E) genomic DNA and identified by polymerase chain reaction (PCR) amplification with 5'-LTR, gag, env, 3'-LTR primer sets. Supernatant collected from FCD4E cells cocultured with JSY3-transfected Crandell feline kidney (CrFK) cells was used as inoculum. Cell-free JSY3 virus was cytopathogenic for FCD4E lymphocytes, but did not infect CrFK cells in vitro. To determine in vivo infectivity and pathogenesis, 6 young adult SPF cats were inoculated with cell-free JSY3 virus. Provirus was detected at 2 wk post-infection, and was still detectable at 25 weeks post infection as determined by gag region PCR/Southern blot analysis of peripheral blood mononuclear cell (PBMC) lysates. Infectious virus was recovered from PBMC at six weeks and 25 weeks post infection, and antibody response to FIV was detected by four weeks post infection. In the acute phase of infection, JSY3 provirus was found only in the CD4+ lymphocyte subset; however, by 14 weeks post invention the greatest provirus burden was detected in B lymphocytes. All six cats were panleukopenic at two weeks post infection, CD4+:CD8+ ratios were inverted by six weeks post-infection, and 5/6 cats developed lymphadenopathy by ten weeks post infection. To determine if the JSY3 molecular clone caused immunodeficiency similar to the parent wild-type FIV-NCSU$_1$, the cats were challenged with the low virulence ME49 strain of *Toxoplasma gondii* (*T. gondii*) at 29 weeks post infection. Five of six cats developed acute respiratory distress and required euthanasia. Histopathologic examination of the severely affected cats revealed generalized inflammatory reactions and the presence of *T. gondii* tachyzoites in multiple tissues. None of the six age- and sex-matched SPF cats inoculated with only *T. gondii* developed clinical disease. These results indicate that the pathogenesis of the molecularly cloned NCSU$_1$ JSY3 isolate is similar to the wild-type FIV-NCSU$_1$ and induces immunodeficiency in cats.

The JSY3 molecular clone retains the essential in vitro and in vivo biological characteristics of the parent virus. This clone was obtained from an EMBL3 lambda phage library made from FCD4E cells, and the intact genomic structure was confirmed by PCR comparison with the FIV-pPPR molecular clone. The JSY3 molecular clone recovered was highly infectious for PBMCs and FCD4E cells but failed to infect CrFK cells, thus retaining the tropism of the parent FIV-NCSU$_1$ virus. Miyazawa et al. (Miyazawa et al., *J. Virol.* 65:1572 (1991)) and Siebelink et al. (Siebelink et al., *J. Virol.* 66:1091 (1992)) reported that CD4+ lymphoblastoid cell line MYA-1 cell-derived or bone marrow-derived molecular clones of FIV recovered from transfected CrFK cells failed to reinfect CrFK but retained their tropism for PBMC and CD4+ cell cultures. Similarly, the PBMC-derived molecular clone FIV-pPPR replicated efficiently in PBMCs but did not infect adherent cells such as CrFK or G355-5 cells (Phillips et al., *J. Virol.* 64:4605 (1990)), whereas the FIV-p34 clone, derived from the CrFK-adapted Petaluma isolate, replicated efficiently in feline adherent cells, including CrFK cells, but inefficiently in PBMCs (Sparger et al., *Virology* 205:546 (1994)).

The JSY3 clone retains the in vivo biological characteristics of the parent NCSU$_1$ virus. Both viruses caused a significant inversion of the CD4+/CD8+ ratio by six weeks post infection. As reported previously for a number of biological isolates of FIV (Ackley et al., *J. Virol.* 64:5652 (1990); Torten et al., *J. Virol.* 65:2225 (1991); Willett et al., *Immunology*, 78:1 (1993)), including the NCSU$_1$ isolate (English et al., *J. Infect. Dis.* 170:543 (1994); Tompkins et al., *J. Am. Vet. Med. Assoc.* 199:1311 (1991)), the inverted CD4+/CD8+ ratio caused by the JSY3 clone was the result of a loss of CD4+ lymphocytes and an increase in CD8+ lymphocytes. Consistent with the NCSU$_1$ biological isolate, the JSY3 molecular clone caused a strong antibody response to gag and env antigens, and PBMCs had a high burden of FIV provirus during the acute-stage infection.

The JSY3 clone exhibited a pattern similar to the parent FIV-NCSU$_1$ (English et al., *J. Virol.* 67:5175 (1993)) of high provirus burden in CD4+ cells during acute-stage infection, followed by a gradual shift to a panlymphotropic pattern during the transition from the acute to the asymptomatic stage of infection.

Derivation of molecular clones of viruses from in vitro culture systems poses the risk of selection of some viral genotypes over others (see Dahl et al., *J. Virol.* 61:1602 (1987; Evans et al., *J. Immunol.* 138:3415 (1987); Meyerhans et al., *Cell* 58:901 (1989)), or introduction of modifications in cultured virus, (see Hirsch et al., *Nature* 341:767 (1989); Kodama et al., *J. Virol.* 63:4709 (1989)). For FIV, Sparger et al. (Sparger et al., *Virology* 205:546 (1994)) reported that the pF34 clone derived from the CrFK-adapted Petaluma isolate is less pathogenic than the parent Petaluma virus isolated from PBMCs. In contrast the FIV-pPPR molecular clone derived from PPR-infected PBMCs and the biological parent PPR isolate show similar pathogenicities, including virus burden in PBMCs and reduced CD4+/CD8+ ratios (Sparger et al., *Virology* 205:546 (1994)). The JSY3 molecular clone also retains the essential biological characteristics of the parent isolate. This may be largely because the risk of culture-related artifacts was minimized by isolating FIV-NCSU$_1$ genomic DNA from FIV-inoculated CD4+ lymphocytes (FCD4E cells). The FCD4E cells used had been in laboratory culture for several years, but remained interleukin-2 dependent and appeared to express a normal rather than a transformed phenotype and thus represent as near as possible in vitro the primary in vivo target of FIV.

The value of a molecular clone for studies of pathogenesis depends on its ability to replicate the disease caused by its biological parent virus. The $NCSU_1$ isolate of FIV causes an acute-stage clinical disease characterized by fever and lymphadenopathy that is transient and resolves as the infection progresses to the clinically asymptomatic stage of infection. The JSY3 acute-stage infection was also characterized by a fever and lymphadenopathy that was followed by a clinically asymptomatic stage.

Davidson et al. (*Am. J. Pathol.* 143:1486 (1993)) reported that cats infected with FIV-$NCSU_1$ become highly susceptible to a normally avirulent strain of *T. gondii* as early as 18 weeks post-FIV infection. This dual FIV-*T. gondii* infection was utilized herein to determine if infection with clone JSY3 also caused an immunodeficiency early in the asymptomatic stage of infection; *T. gondii* infection of cats with prior JSY3 infection resulted in severe clinical infection as described below.

The present observations indicate that the JSY3 molecular clone causes a major impairment in the immune response, resulting in enhanced susceptibility to secondary infection by *T. gondii*. Thus, JSY3 possesses all of the essential biological characteristics of the parent $NCSU_1$ isolate, including induction of immunodeficiency.

A. The JSY3 Genome

The DNA sequence of the JSY3 provirus clone of FIV-$NCSU_1$ is provided in FIG. 1, with the group specific antigen (gag), polymerase (pol), and envelope protein (env) regions marked. The JSY3 proviral DNA sequence consists of 9471 base pairs (SEQ ID NO:1).

The coding region of gag is nucleotides 631–1980 of SEQ ID NO:1 (SEQ ID NO:4) and encodes a 450 amino acid product (SEQ ID NO:2).

The coding region for the p15 protein is nucleotides 631–1035 of SEQ ID NO:1 (SEQ ID NO:5), with a polypeptide product of 135 amino acids (SEQ ID NO:6).

The coding region for the p25 protein is nucleotides 1036–1704 of SEQ ID NO:1 (SEQ ID NO:7), with a polypeptide product of 223 amino acids (SEQ ID NO:8).

The coding region for the p24a protein is nucleotides 1264–1305 of SEQ ID NO:1 (SEQ ID NO:9), with a polypeptide product of 14 amino acids (SEQ ID NO:10).

The coding region for the p10 protein is nucleotides 1717–1980 of SEQ ID NO:1 (SEQ ID NO:11), with a polypeptide product of 88 amino acids (SEQ ID NO:12).

The coding region of pol is amino acids 2151–5991 of SEQ ID NO:1 (SEQ ID NO:13). Two open reading frames (orfs) are found in the pol region. Orf 1 is nucleotides 2151–5243 of SEQ ID NO:1 (SEQ ID NO:14), encoding a product of 1031 amino acids (SEQ ID NO:15); Orf 2 is nucleotides 5239–5991 of SEQ ID NO:1 (SEQ ID NO:16) and encodes a product of 251 amino acids (SEQ ID NO:17).

The env coding region is nucleotides 6269–8824 of SEQ ID NO:1 (SEQ ID NO:18) and encodes a protein of 852 amino acids (SEQ ID NO:3). The transmembrane (TM) peptide is encoded by nucleotides 8339–8374 of SEQ ID NO:1 (SEQ ID NO:19), and is 12 amino acids in length (SEQ ID NO:20).

FIG. 2 aligns the gag open reading frames of the JSY3 clone of $NCSU_1$ (FIV-NCSU), FIV PPR, FIV Z1, FIV CG, FIV 14, FIV TM1, and FIV TM2. FIG. 3 aligns the whole envelope protein sequence of clone JSY3 of $NCSU_1$ with FIV 14, FIV Z1, FIV CG, FIV 19k, and FIV PPR.

Amino acid sequences disclosed herein are presented in the amino to carboxy direction, from left to right. The amino and carboxy groups are not presented in the sequence. Nucleotide sequences are presented herein by single strand only, in the 5' to 3' direction, from left to right. Nucleotides and amino acids are represented herein in the manner recommended by the IUPAC-IUB Biochemical Nomenclature Commission, or (for amino acids) by three letter code in accordance with 37 C.F.R. §1.822 and established usage. See, e.g. Patent In User Manual, 99–102 (November 1990) (U.S. Patent and Trademark Office, Office of the Assistant Commissioner for Patents, Washington D.C. 20231); U.S. Pat. No. 4,871,670 to Hudson et al. at Col. 3, lines 20–43 (applicants specifically intend that the disclosure of this and all patent references cited herein are to be incorporated herein by reference).

Aspects of the present invention are achieved by a viral clone having the DNA sequence as provided herein for Feline Immunodeficiency Virus clone JSY3.

B. Identification of Antigenic Fragments

Antigenic fragments of the present invention are peptides which contain at least one epitope (antibody binding site) which binds antibodies which bind to the FIV clone of the present invention. The antigenic fragments are preferably capable of inducing an immune response when administered to a feline subject, as discussed in greater detail below. In addition, the antigenic fragments preferably bind antibodies which do not bind to prior FIV isolates. DNA encoding such antigenic fragments may be used to transform host cells to thereby produce such antigenic fragments, as explained in greater detail below.

Antigenic fragments may be identified by a variety of means. A protein from FIV clone JSY3 (such as the envelope protein, the gag open reading frame product, or a gag peptide such as p10, p10, p24a or p25) may be fragmented with a protease, and the fragments tested to determine whether or not a fragment reacts with antiserum against the protein. See, e.g., J. Robinson et al., *Mol. Cell Biochem.* 21, 23–32 (1978). Another technique is to synthesize peptides which are fragments of the entire protein, and determine whether the individual fragments are recognized by neutralizing antibodies against the protein. See, e.g., J. Gerin et al., in *Vaccines* 85: *Molecular and Chemical Basis of Resistance to Parasitic, Bacterial and Viral Diseases,* 235–239 (Lerner et al., eds. 1985). Still another method useful for obtaining immunogenic fragments of a protein is by isolation and identification of monoclonal escape mutants. In this strategy, FIV is produced in the presence of a monoclonal antibody to the virus. The only virus which can grow under these conditions are those with a mutation in the nucleotide sequence which codes for an epitope to which the monoclonal antibody binds. A mutant virus which grows under these conditions is referred to as the "monoclonal escape mutant." The monoclonal escape mutant is then sequenced and the mutant sequence compared with the nucleotide sequence of clone JSY3 to find the specific location of the mutation. The mutation is located in a region which codes for a protective epitope, or an "immunogenic fragment." See, e.g., J. Lopez et al., Location of a Highly Conserved Neutralizing Epitope in the F Glycoprotein of Human Respiratory Syncytial Virus, *J. Virol.* 64, 927 (1990).

C. Genetic Engineering Techniques

The production of DNA, vectors, transformed host cells, FIV virus, proteins, and protein fragments of the present invention by genetic engineering techniques can be carried out in accordance with methods known in the art. See, e.g., U.S. Pat. No. 4,761,371 to Bell et al. at Col. 6 line 3 to Col. 9 line 65; U.S. Pat. No. 4,877,729 to Clark et al. at Col. 4 line 38 to Col. 7 line 6; U.S. Pat. No. 4,912,038 to Schilling at Col. 3 line 26 to Col. 14 line 12; and U.S. Pat. No. 4,879,224 to Wallner at Col. 6 line 8 to Col. 8 line 59.

Vectors are replicable DNA constructs used to either amplify or express DNA of the present invention. An expression vector is a replicable DNA construct in which DNA of the present invention is operably linked to control sequences capable of expressing that DNA in a suitable host. Generally, control sequences include a transcriptional promoter, an optional operator sequence to control transcription, a sequence encoding suitable mRNA ribosomal binding sites, and sequences which control the termination of transcription and translation. Suitable vectors include plasmids, viruses (e.g., vaccinia virus, adenovirus, baculovirus, cytomegalovirus), phage, and integratable DNA fragments (i.e., fragments integratable into the host genome by recombination).

DNA regions are operably linked or operably associated when they are functionally related to each other. For example, a promoter is operably linked to a coding sequence if it controls the transcription of the sequence; or a ribosome binding site is operably linked to a coding sequence if it is positioned so as to permit translation.

Transformed host cells are cells which have been transformed or transfected with vectors as described above. Transformed host cells ordinarily express the DNA of the present invention. As used herein, host cells containing the FIV clone JSY3 refer to isolated cells (or cultures of such cells) naturally infected with JSY3, including cells containing the JSY3 proviral DNA integrated into cellular DNA. Suitable host cells include prokaryote, yeast or higher eukaryotic cells such as mammalian cells and insect cells.

Prokaryote host cells include gram negative or gram positive organisms, for example *Escherichia coli* (*E. coli*) or Bacilli. Exemplary host cells are *E. coli* W3110 (ATCC 27,325), *E. coli* B, *E. coli* X1776 (ATCC 31,537), *E. coli* 294 (ATCC 31,446). A broad variety of suitable prokaryotic and microbial vectors are available. *E. coli* is typically transformed using pBR322. Promoters most commonly used in recombinant microbial expression vectors include the β-lactamase (penicillinase) and lactose promoter systems (Chang et al., *Nature* 275:615 (1978); and Goeddel et al., *Nature* 281:544 (1979)), a tryptophan (trp) promoter system (Goeddel et al., *Nucleic Acids Res.* 8:4057 (1980) and EPO App. Publ. No. 36,776) and the tac promoter (H. De Boer et al., *Proc. Natl. Acad. Sci. USA* 80:21 (1983)). The promoter and Shine-Dalgarno sequence are operably linked to the DNA of the invention, i.e., they are positioned so as to promote transcription of messenger RNA from the DNA.

Eukaryotic microbes such as yeast cultures may also be transformed with vectors of the present invention. See, e.g., U.S. Pat. No. 4,745,057. *Saccharomyces cerevisiae* is the most commonly used yeast, although other yeast may also be used. Yeast vectors may contain an origin of replication from the 2 micron yeast plasmid or an autonomously replicating sequence (ARS), a promoter, a JSY3 coding region, sequences for polyadenylation and transcription termination, and a selection gene. An exemplary plasmid is YRp7, (Stinchcomb et al., *Nature* 282:39 (1979); Kingsman et al., Gene 7:141 (1979); Tschemper et al., *Gene* 10:157 (1980)). Suitable promoting sequences in yeast vectors include the promoters for metallothionein, 3-phosphoglycerate kinase (Hitzeman et al., *J. Biol. Chem.* 255:2073 (1980) or other glycolytic enzymes (Hess et al., *J. Adv. Enzyme Reg.* 7:149 (1968); and Holland et al., *Biochemistry* 17:4900 (1978)).

Host cells such as insect cells (e.g., cultured *Spodoptera frugiperda* cells) and expression vectors such as the baculovirus expression vector (e.g., vectors derived from Autographa californica MNPV, Trichoplusia ni MNPV, Rachiplusia ou MNPV, or Galleria ou MNPV) may be employed in carrying out the present invention, as described in U.S. Pat. Nos. 4,745,051 and 4,879,236 to Smith et al. In general, a baculovirus expression vector comprises a baculovirus genome containing the gene or coding region to be expressed inserted into the polyhedrin gene at a position ranging from the polyhedrin transcriptional start signal to the ATG start site and under the transcriptional control of a baculovirus polyhedrin promoter.

Examples of useful mammalian host cell lines are VERO and HeLa cells, Chinese hamster ovary (CHO) cell lines, and WI138, BHK, COS-7, CV, and MDCK cell lines. The transcriptional and translational control sequences in expression vectors to be used in transforming vertebrate cells are often provided by viral sources. For example, commonly used promoters are derived from polyoma, Adenovirus 2, and Simian Virus 40 (SV40). See, e.g., U.S. Pat. No. 4,599,308. An origin of replication may be provided either by construction of the vector to include an exogenous origin, such as may be derived from SV40 or other viral (e.g. Polyoma, Adenovirus, VSV, or BPV) source, or may be provided by the host cell chromosomal replication mechanism. If the vector is integrated into the host cell chromosome, the latter is often sufficient. Rather than using vectors which contain viral origins of replication, one can transform mammalian cells by the method of cotransformation with a selectable marker and DNA of the present invention, as described in U.S. Pat. No. 4,399,216.

Alternatively, the invention DNA sequences can be translated into RNA, which can then be transfected into amphibian cells for transcription into protein. Suitable amphibian cells include Xenopus oocytes.

Use of the phrase "substantial sequence similarity" in the present specification and claims means that DNA, RNA or amino acid sequences which have slight and non-consequential sequence variations from the actual sequences disclosed and claimed herein are considered to be equivalent to the sequences of the present invention. In this regard, "slight and non-consequential sequence variations" mean that "similar" sequences (i.e., the sequences that have substantial sequence similarity with the DNA, RNA, or proteins disclosed and claimed herein) will be functionally equivalent to the sequences disclosed and claimed in the present invention. Functionally equivalent sequences will function in substantially the same manner to produce substantially the same compositions as the nucleic acid and amino acid compositions disclosed and claimed herein.

As used herein, the term 'gene' refers to a DNA sequence that incorporates (1) upstream (5') regulatory signals including the promoter, (2) a coding region specifying the product, protein or RNA of the gene, (3) downstream (3') regions including transcription termination and polyadenylation signals and (4) associated sequences required for efficient and specific expression.

The term 'promoter' refers to a region of a DNA sequence that incorporates the necessary signals for the efficient expression of a coding sequence. THis may include sequences to which an RNA polymerase binds but is not limited to such sequences and may include regions to which other regulatory proteins bind together with regions involved in the control of protein translation and may include coding sequences.

D. Vaccines and Vaccine Formulations

The present invention provides for a variety of different vaccines useful for protecting feline species against FIV.

Examples include live attenuated clone JSY3 virus, fixed whole virus, host cells which express virus antigen on the surface thereof (with the cells optionally fixed), preparations of virus fragments, purified proteins, antigenic fragments of proteins, and antigenic peptides which are derivatives of the antigenic fragments (as discussed in detail below). These various compounds and mixtures are generically referred to herein as active agents.

Live attenuated FIV clone JSY3 virus is made by serial passage of the virus in tissue culture or genetically altered by recombinant techniques, in accordance with known procedures. Fixed virus is made by contacting live virus (attenuated or unattenuated) to a suitable fixative, such as formalin.

Preparations of viral fragments are made by lysing host cells, such as E. coli cells, transformed with a vector encoding the FIV of the present invention or a portion thereof. For example, the vector may encode a JSY3 DNA segment which produces hollow virus particles which are antigenic. The lysate may be used in crude form, partially purified, or a particular viral protein (or antigenic fragment thereof) such as the envelope protein purified to homogeneity, and used as an active agent for a vaccine against FIV.

Host cells such as yeast cells may be transformed with vectors of the present invention capable of expressing JSY3 proteins, or antigenic fragments thereof, on the surface of the host cells, and the transformed host cells used as an active vaccine agent per se or fixed (e.g., with formalin) and used as an active agent.

Antigenic peptides are selected from the group consisting of antigenic fragments of FIV clone JSY3 proteins, such as the envelope protein, the gag open reading frame product, and gag peptides (such as p10, p15, p24a, p25) and the antigenic equivalents thereof (i.e., analogs or derivatives). Antigenic peptides may be chemically synthesized or produced by recombinant techniques. The antigenic fragments are preferably not more than 20 amino acid residues in length, and are more preferably not more than 10 amino acid residues in length. The antigenic equivalents are selected from the group consisting of: (a) modified peptides comprising the aforesaid antigenic fragments modified by the inclusion of one or more changes to the amino acid sequence thereof; and (b) longer peptides which incorporate the sequence of the aforesaid fragments or the aforesaid modified peptides and which have (i) up to four extra amino acid residues attached to the C-terminal end thereof, (ii) up to four extra amino acid residues attached to the N-terminal end thereof, or (iii) up to four extra amino acid residues attached to the C-terminal end thereof and up to four extra amino acid residues attached to the N-terminal end thereof.

The term "antigenic equivalents," as used herein, refers to proteins or peptides which bind to an antibody which binds to the protein or peptide with which equivalency is sought to be established. Antibodies which are used to select such antigenic equivalents are referred to as "selection antibodies" herein. Preferred selection antibodies are monoclonal antibodies which bind to clone JSY3, but preferably not to isolates of FIV other than FIV strain $NCSU_1$ (such as the Petaluma strain isolated by N. Pedersen), and most preferably not to other molecular clones of FIV $NCSU_1$.

One or more amino acids of an antigenic peptide sequence may be replaced by one or more other amino acids which does not affect the antigenicity of that sequence. Such changes can be guided by known similarities between amino acids in physical features such as charge density, hydrophobicity/hydrophilicity, size and configuration. For example, Thr may be replaced by Ser and vice versa, Asp may be Replaced by Glu and vice versa, and Leu may be replaced by Ile and vice versa.

Antigenic equivalents may be formed by modifying reactive groups within a natural sequence or modifying the N-terminal amino and/or C-terminal carboxyl group. Such equivalents include salts formed with acids and/or bases, particularly physiologically acceptable inorganic and organic acids and bases. Other equivalents include modified carboxyl and/or amino groups on the synthetic peptide to produce esters or amides, or amino acid protecting groups such as N-t-butoxycarbonyl. Preferred modifications are those which provide a more stable, active peptide which will be less prone to enzymatic degradation in vivo.

For use as a vaccine, the active agents of the present invention may be administered to the subject by any suitable means. Exemplary are by intramuscular injection, by subcutaneous injection, by intravenous injection, by intraperitoneal injection, by oral injection, and by nasal spray.

The amount of active agent administered will depend upon factors such as route of administration, species, and the use of booster administrations. In general, a dosage of about 0.1 to about 100 $\mu$g per pound subject body weight may be used, more particularly about 1 $\mu$g per pound.

Vaccine formulations of the present invention comprise the active agent in a pharmaceutically acceptable carrier. The active agent is included in the carrier in an amount effective to protect the subject being treated. Pharmaceutically acceptable carriers are preferably liquid, particularly aqueous, carriers, such as sodium phosphate buffered saline. The vaccine formulation may be stored in a sterile glass container sealed with a rubber stopper through which liquids may be injected and formulations withdrawn by syringe.

Vaccine formulations of the present invention may optionally contain one or more adjuvants. Any suitable adjuvant can be used, exemplary being aluminum hydroxide, aluminum phosphate, plant and animal oils, synthetic polymers and the like, with the amount of adjuvant depending on the nature of the particular adjuvant employed. In addition, the vaccine formulations may also contain one or more stabilizer, exemplary being carbohydrates such as sorbitol, mannitol, starch, sucrose, dextrin, and glucose, proteins such as albumin or casein, and buffers such as alkaline metal phosphates and the like.

E. Infection of Cats with FIV clone JSY3

Cats infected with FIV clone JSY3 are useful as a model system for the study of retroviral infections, such as by HIV. Cats used for this purpose are preferably specific pathogen-free (SPF) cats, which are commercially available from sources such as Charles River Laboratories and Berkshire Laboratories. Infected cats are preferably maintained as a single colony of two or more cats, all infected with FIV clone JSY3. The colony may be maintained in a single room with each cat housed in an appropriate cage, in accordance with standard practices for the maintenance of animals. A colony will consist of a plurality of infected cats, typically from ten, fifteen, twenty, thirty or more cats; the number of individual cats will vary according to need. Preferably, all members of the colony are SPF cats (i.e., free of pathogens other than FIV clone JSY3).

SPF cats may be infected with FIV clone JSY3 by any suitable means, such as by intraperitoneal, intravenous, or subcutaneous injection with a solution containing FIV clone JSY3. The solution may be blood from a previously infected cat, a blood fraction containing peripheral blood mononuclear cells from a previously infected cat, a pharmaceutically acceptable carrier such as saline solution containing FIV clone JSY3, etc.

Cats infected with FIV clone JSY3 are particularly useful as a model system for immunodeficient states associated with retroviral infection because of the rapid inversion of the CD4+:CD8+ ratio caused by JSY3. When used as a model system, the cat or cats infected with FIV clone JSY3 is subjected to a treatment, which treatment is a candidate for use in combating retroviral infections, and the progress of the FIV infection cat or cats thereafter examined. A control group of cats infected with FIV clone JSY3 but untreated, or placebo treated, may be included as a control group. A slowing in the progression of the disease in the cats indicates that the treatment may be useful for combating retroviral diseases in other animal subjects. Typically, the candidate treatment will then be subjected to further screening procedures and toxicological testing to determine whether the treatment may be clinically useful. The treatment to which the cats are subjected may be any treatment, such as the administration of candidate drugs (e.g., candidate antiretroviral compounds) or drug combinations, including small organic compounds, peptides, or proteins, which may be administered orally or parenterally, or may involve treatments other than the administration of drugs such as a biological response modifier or a vaccine. The progress of the disease in the cats after treatment can be monitored by any suitable means, such as examination for inhibition of the deterioration of CD4+ cell levels, declines in the circulating levels of the FIV GAG protein, the weight of the cat and its general appearance, etc.

An advantage of using JSY3 infected cats as a model for retroviral disease as described above is that the FIV virus is not infectious to humans. A disadvantage of this model is that cats are somewhat large animals; mice are much more practical as animal models of disease.

An additional aspect of the present invention is an immunodeficient mouse containing feline tissue, which feline tissue is capable of infection with feline -immunodeficiency virus (FIV). The mouse is infected with FIV clone JSY3, and used as an animal model in essentially the same manner as cats as described above. Any suitable immunodeficient mouse may be employed, such as SCID mice (e.g., the C.B.-17 scid/scid mouse) athymic mice such as the nude mouse, and mice which have been rendered immunodeficient by treatment with radiation. The mouse may be deficient in T lymphocytes function alone (e.g., athymic mice), but is preferably deficient in both T and B lymphocyte function.

The feline tissue which the immunodeficient mice contains preferably comprises one or more of the following: feline thymus tissue, feline lymph node tissue, feline liver cells, feline bone marrow cells, feline peripheral blood mononuclear cells such as peripheral blood lymphocytes and peripheral blood monocytes, and feline spleen cells. The feline tissue may be introduced into the mouse by any suitable means, such as intraperitoneal injection, intravenous injection, surgical implantation, and combinations thereof. Feline tissue may be introduced as organized tissues (e.g., thymus and lymph node) or as discrete cells. One example is an immunodeficient mouse having feline thymus tissue and/or lymph node tissue surgically implanted. Another example is an immunodeficient mouse into which peripheral blood mononuclear cells have been intraperitoneally injected.

F. Diagnostic Probes

The FIV clone JSY3 nucleotide sequence can be used to generate hybridization probes which specifically bind to FIV clone JSY3 genetic material, or the genetic material of FIV clones having all of, or essentially all of, the identifying characteristics of FIV clone JSY3, to determine the presence of such FIV in cats. The hybridization probe may be selected so that it does not bind to known FIV isolates (such as the Petaluma strain) other than $NCSU_1$, or to any FIV isolate or clone other than JSY3. Hybridization probes may be cDNA fragments or oligonucleotides, and may be labelled with a detectable group as discussed hereinbelow. Pairs of probes which will serve as PCR primers for the JSY3 genome or a portion thereof may be used in accordance with the process described in U.S. Pat. Nos. 4,683,202 and 4,683,195.

For example, an illustrative embodiment of the above probes comprises DNA sequences set forth in SEQ ID NOS:4, 5, 7, 9, 11, 13, 14, 16, 18, and 19, or suitable fragments thereof.

The term "labelled" is used herein to refer to the conjugating or covalent bonding of any suitable detectable group, including enzymes (e.g., horseradish peroxidase, β-glucuronidase, alkaline phosphatase, and β-D-galactosidase), fluorescent labels (e.g., fluorescein, luciferase), and radiolabels (e.g., $^{14}C$, $^{131}I$, $^3H$, $^{32}P$, and $^{35}S$) to the compound being labelled. Techniques for labelling various compounds, including proteins, peptides, and antibodies, are well known. See, e.g., Morrison, *Methods in Enzymology* 32b, 103 (1974); Syvanen et al., *J. Biol. Chem.* 284, 3762 (1973); Bolton and Hunter, *Biochem. J.* 133, 529 (1973).

G. DNA Sequence and Genome Organization

Isolated DNA from the JSY3 provirus may be used to generate hybridization probes, which may be used in diagnostic assays as discussed above. Isolated DNA capable of expressing antigenic proteins or antigenic fragments thereof may be used for producing proteins which are also useful in diagnostic assays.

An aspect of the present invention is oligonucleotide probes which selectively hybridize to DNA encoding a group antigen (gag) polypeptide (or an antigenic fragment thereof) of FIV clone JSY3 under stringent conditions, which probes do not bind to DNA encoding the group antigen (gag) polypeptide of the following known FIV strains under the same stringency conditions: FIV-Petaluma (U.S. Pat. No. 5,037,753); FIV-PPR (Phillips et al., *J. Virology*, 64:4605 (1990)); FIV-TM1 and FIV-TM2 (Miyazawa et al., *Arch. Virology* 108:59 (1989)); FIV-UT113 (Verschoor et al., *J. Cell. Biochem.*, Suppl. 14D:143 (1990). Conditions which will permit other DNA coding for an FIV gag polypeptide to hybridize to the DNA of FIV clone JSY3 gag polypeptide can be determined in a routine manner. For example, hybridization may be carried out under conditions of reduced stringency or even stringent conditions (e.g., conditions represented by a wash stringency of 0.3M NaCl, 0.03M sodium citrate, and 0.1% SDS at 60° C. or even 70° C.) to DNA encoding the gag polypeptide of FIV clone JSY3 disclosed herein in a standard in situ hybridization assay. See J. Sambrook et al., Molecular Cloning, A Laboratory Manual (2nd Ed. 1989) (Cold Spring Harbor Laboratory)).

In general, DNA which codes for FIV gag polypeptide or antigenic fragments thereof and which hybridizes to DNA encoding gag polypeptide (or antigenic fragments thereof) of FIV clone JSY3 disclosed herein will have at least 75%, 80%, 85%, or even 90% or more sequence similarity with the DNA of the gag polypeptide (or antigenic fragments thereof) of FIV clone JSY3 disclosed herein. Further, DNA which codes for FIV gag polypeptide (or antigenic fragments thereof), or which codes for a gag polypeptide or antigenic fragment coded for by DNA which hybridizes to the DNA which codes for FIV clone JSY3 gag polypeptide or antigenic fragment thereof, but which differ in codon sequence from these due to the degeneracy of the genetic code, are also an aspect of this invention. The degeneracy of the genetic code, which allows different nucleic acid sequences to code for the same protein or peptide, is well known in the literature. See, e.g., U.S. Pat. No. 4,757,006 to Toole et al. at Col. 2, Table 1.

A particular embodiment of the foregoing also disclosed herein is isolated DNA encoding the group antigen (gag) polypeptide or an antigenic fragment thereof, of FIV clone JSY3, and isolated DNA encoding the envelope protein or an antigenic fragment thereof, where the DNA is: (a) isolated DNA encoding group antigen (gag) polypeptide or envelope protein, or an antigenic fragment thereof, of FIV clone JSY3, (b) isolated DNA which hybridizes to isolated DNA of (a) above under stringent conditions and which encodes a feline immunodeficiency virus group antigen (gag) polypeptide, envelope protein, or antigenic fragment thereof with at least 75%, 80%, 85% or even 90% or more sequence similarity to isolated DNA of (a) above; or (c) isolated DNA differing from the isolated DNAs of (a) and (b) above in nucleotide sequence due to the degeneracy of the genetic code, and which encodes a feline immunodeficiency virus group antigen (gag) polypeptide, envelope protein, or antigenic fragment thereof encoded by the isolated DNAs of (a) or (b), above.

An illustrative embodiment of the foregoing DNA which codes for FIV clone JSY3 gag polypeptide (or antigenic fragments thereof) is DNA according to SEQ ID NO:4 or a portion thereof; DNA according to SEQ ID NO:5 (p15) or a portion thereof; DNA according to SEQ ID NO:7 (p25) or a portion thereof; DNA according to SEQ ID NO:9 (p24a) or a portion thereof; DNA according to SEQ ID NO:11 (p10) or a portion thereof. An illustrative embodiment of the foregoing DNA which codes for FIV clone JSY3 envelope protein (or antigenic fragments thereof) is SEQ ID NO:18 or SEQ ID NO:19. Also disclosed herein are recombinant DNA sequences comprising vector DNA and a DNA encoding group specific antigen (gag) polypeptides of clone JSY3, or the envelope protein of JSY3, or antigenic fragments thereof (as given above).

The FIV provirus includes the structural genes for group-specific antigens (gag gene), envelope proteins (env gene) and reverse transcriptase (pol gene), as well as several short open reading frames similar to those of other lentiviruses. Omsted et al., *Proc. Natl. Acad. Sci. USA*, 86, 2448 (1989); Olmsted et al., *Proc. Natl. Acad. Sci. USA*, 86, 8088 (1989). The gag gene of FIV has been reported to encode a polyprotein of about 450 amino acids, which is subjected to post-translational cleavage. Talbot et al., *Proc. Natl. Acad. Sci. USA*, 86, 5743 (1989); Phillips et al., *J. Virology*, 64, 4605 (1990). The gag gene and its predicted protein product has been reported to be highly conserved among isolates of FIV. Phillips et al., *J. Virology*, 64, 4605 (1990); Morikawa et al., *Virology*, 183, 288 (1991). FIV gag gene has been expressed in baculovirus vectors and assembled into virus-like particles. Morikawa et al., *Virology*, 183, 288 (1991).

Isolated and purified FIV clone JSY3 group antigen (gag) polypeptide, envelope protein, or antigenic fragments thereof are also an aspect of the present invention. These polypeptides or fragments are coded for by: (a) isolated DNA which encodes group antigen (gag) polypeptide or envelope protein, or an antigenic fragment thereof, of FIV clone JSY3; (b) isolated DNA which hybridizes to isolated DNA of (a) above under stringent conditions and which encodes a FIV gag polypeptide, envelope protein, or antigenic fragment thereof with at least 75% sequence similarity to isolated DNA of (a) above; or (c) isolated DNA differing from the isolated DNAs of (a) and (b) above in nucleotide sequence due to the degeneracy of the genetic code, and which encodes a FIV gag polypeptide, envelope protein, or antigenic fragment thereof encoded by DNAs of (a) or (b), above. By antigenic polypeptide is meant a polypeptide which is able to raise (with the aid of an adjuvant if necessary) an antibody response in cats. The polypeptide may be a fragment of a polypeptide naturally occurring in FIV particles. The fragment may be from a naturally occurring polypeptide or produced by isolation or synthesis of a gene or coding region encoding a desired polypeptide and expression within an appropriate expression system.

An illustrative embodiment of the foregoing polypeptides is the JSY3 group antigen specific polypeptide (SEQ ID NO:2) and peptides thereof (SEQ ID NO:6 (p15); SEQ ID NO:8 (p25); SEQ ID NO:10 (p24a); SEQ ID NO:12 (p10)); and the JSY3 envelope protein (SEQ ID NO:3) and TM protein (SEQ ID NO:19).

The present invention is explained in greater detail in the non-limiting Examples set forth below.

EXAMPLE 1

Materials and Methods

Viruses. The biological parent virus isolate FIV-NCSU$_1$ (U.S. Pat. No. 5,413,927 to Tompkins et al.) was obtained from the peripheral blood mononuclear cells (PBMCs) of a cat naturally infected with FIV and has been described elsewhere (Davidson et al., *Am. J. Pathol.* 143:1486 (1993); English et al., *J. Virol.* 67:5175 (1993); English et al., *J. Infect. Dis.* 170:543 (1994); Tompkins et al., *J. Am. Vet. Med. Assoc.* 199:1311 (1991)). The NCSU$_1$ isolate (or "NCSU-1") is available from the American Type Culture Collection (ATCC Number VR2333), 12301 Parklawn Drive, Rockville, Md. 20852 USA (deposited in accordance with the provisions of the Budapest Treaty, Jul. 23, 1991). See U.S. Pat. No. 5,413,927 to Tompkins et al. The FIV-NCSU$_1$ molecular clone JSY3 inoculum was collected from an FCD4E feline lymphocyte culture which had been cocultured with transfected Crandell feline kidney (CrFK) cells (see below).

Figure 4:
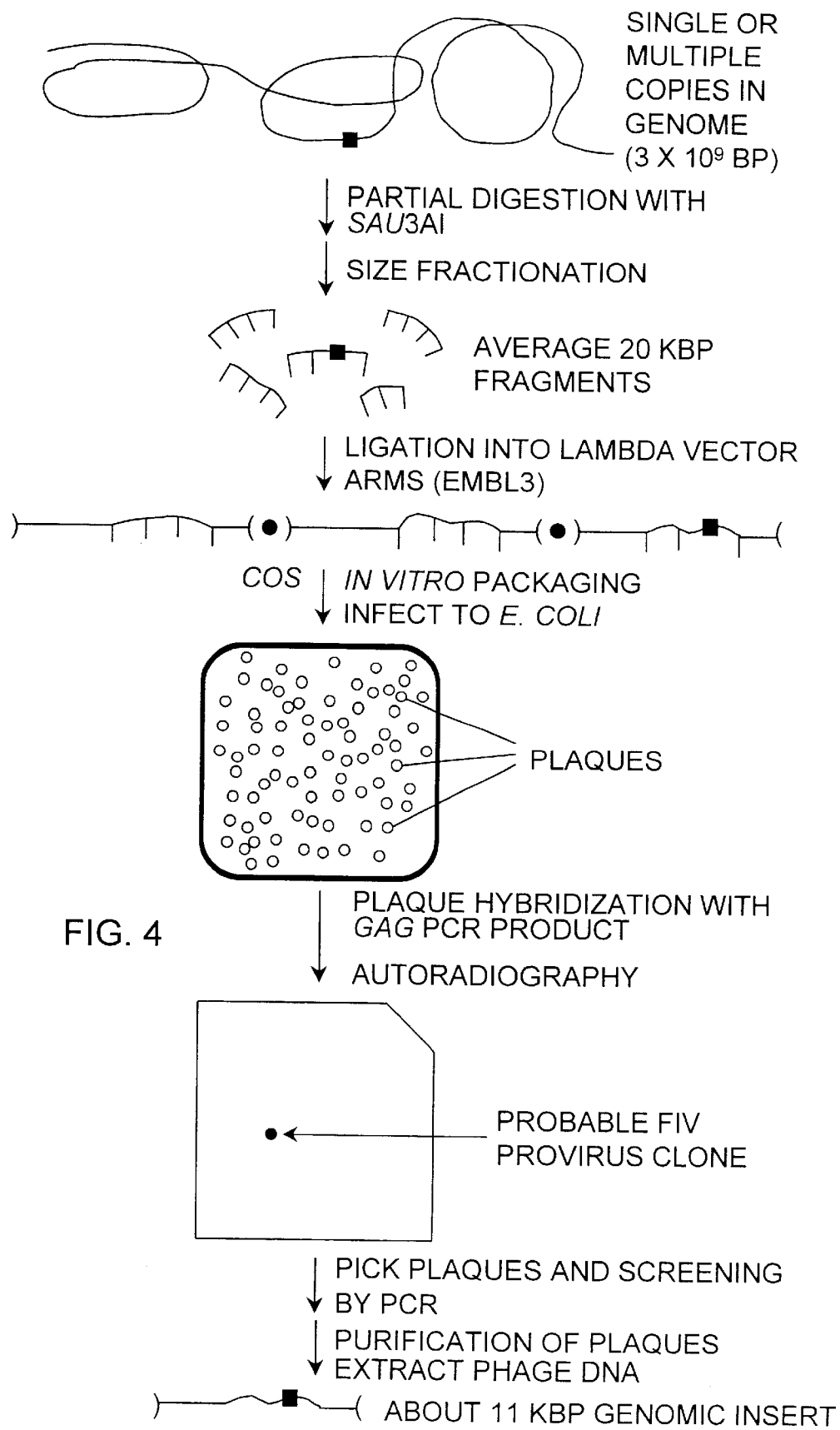
FIG. 4 is a schematic of the strategy used for the molecular cloning of the FIV JSY3 full-length genome, beginning with total cellular DNA from FCD4E cells directly infected with FIV-$NCSU_1$.

Molecular cloning of the FIV proviral genome. Genomic DNA was isolated by equilibrium centrifugation in CsCl-ethidium bromide gradients (Maniatis et al., Molecular cloning: A laboratory manual, Cold Spring Harbor Laboratory, Cold Spring Harbor, N.Y.) from 5×10$^7$ FCD4E cells (interleukin-2-dependent, FIV-NCSU$_1$-infected feline CD4+ lymphocytes) inoculated with FIV-NCSU$_1$ obtained from the original source cat. As shown in FIG. 4, FCD4E genomic DNA which had been partially digested with Sau3AI and size fractionated was cloned into the EMBL3 lambda vector arm. Genomic libraries were screened primarily by plaque hybridization with a gag region PCR product probe (838 bp) as described elsewhere (Maniatis et al., *Molecular cloning: A laboratory manual,* Cold Spring Harbor Laboratory, Cold Spring Harbor, N.Y.). A full-length clone was identified by PCR of phage suspension with six primer sets designed from FIV-14 sequences (GenBank accession no. M25381). These primer sets amplified 5' long terminal repeat, gag, env, and 3' long terminal repeat regions under the PCR conditions described below. The following primers were used for identification of the full-length lambda clone JSY3 (each primer designated by the 5' nucleotide of the complete FIV-14 sequence): 3U (U3) 5'-GGA TGA GTA TTG AAA CCC TGA A-3' (SEQ ID NO:21); 337L (US) 5'-GAT TCC GAG ACC TCA CAG GTA A-3' (SEQ ID NO:22); 447U 5'-AAT AGG GAA GCA GTA GCA GAC-3' (SEQ ID NO:23); 829L 5'-GTA AAT CGC AAA TAA CCA ACC-3' (SEQ ID NO:24); 919U (FIV7) 5'-TGA CGG TGT CTA CTG CTG CT-3' (SEQ ID NO:25); 1756L (FIV8) 5'-CAC ACT GGT CCT GAT CCT TTT-3' (SEQ ID NO:26); 1057U 5'-CCA CAA TAT GTA GCA CTT GAC C-3' (SEQ ID NO:27); 1639L 5'-GGG TAC TTT CTG GCT TAA GGT G-3' (SEQ ID NO:28); 6938U 5'-GGG GGA CCT ACC TTG GGG AAT TGG GCT-3' (SEQ ID NO:29); 7252L 5'-GGT GAT CAT GAT CAG TGG GAT TTG TAA TGG GTC TG-3' (SEQ ID NO:30); 7252L 5'-GGT GAT CAT GAT CAG TGG GAT TTG TAA TGG GTC TG-3' (SEQ ID NO:31); 8859U 5'-ATA AGG GAG ATA CTG TGC TGA-3' (SEQ ID NO:32); 9029L 5'- GCG ATC TTC TAA CTC TGT CAT-3' (SEQ ID NO:33).

DNA transfection. Ten micrograms of lambda clone DNA was transfected into CrFK and AH927 (a feline embryonic fibroblast cell line) cells by using the cationic liposome DOTAP (Boehringer Mannheim, Indianapolis, Ind.) according to the manufacturer's protocol. Twenty-four hours after transfection, these cells were cocultured for 72 hours with FCD4E or concanavalin A (10 µg/ml)-stimulated normal cat PBMCs. FCD4E (or PBMCs) and CrFK (or AH927) cells were then cultured separately. Culture supernatant was collected at 3- to 4- day intervals and assayed for RT activity. Pooled samples for in vivo infection were titrated in FCD4E cells by the 50% tissue culture infective dose ($TCID_{50}$) method.

In vitro infections with JSY3 clone. Cultures of FCD4E or DEAE-dextran-treated CrFK cells were inoculated with cell-free FIV-NCSU$_1$ JSY3 clone containing $2 \times 10^4$ cpm of RT activity. The culture supernatant was collected twice weekly and assayed for RT activity.

In vivo FIV infection. Six 6-month old female cats were inoculated intravenously with $10^6$ $TCID_{50}$s of the JSY3 clone. Nine age- and sex-matched specific-pathogen-fee (SPF) cats were inoculated with wild-type FIV-NCSU$_1$, and nine mock-infected SPF cats were used as controls. The wild-type FIV-NCSU$_1$ infected group was examined up to 18 weeks post infection (p.i.) in parallel with the JSY3-infected cats.

Blood sampling. Whole blood was collected by jugular venipuncture into sodium citrate anticoagulant tubes. Aliquots were removed for complete blood counts and flow cytometry, and plasma was collected for anti-FIV antibody assays. PBMCs were purified over Percoll as described (Tompkins et al., Vet. Immunol. Immunopathol., 16:1 (1987)). PBMCs were then cocultured with FCD4E cells for infectious virus recovery, lysed for provirus detection by PCR, or sorted for lymphocyte subset tropism studies.

Lymphocyte subset analysis by flow cytometry. Lymphocyte subsets were determined by two-color flow cytometric analysis as described (Davidson et al., Am. J. Pathol. 143:1486 (1993)) using a panel of monoclonal antibodies (MAbs) (Tompkins et al., Vet. immunol. Immunopathol. 26:305 (1990)). Briefly, plasma was removed, the cells were washed twice in phosphate-buffered saline (PBS), and MAbs were added in a combination of fluorescein isothiocyanate-labeled anti-cat immunoglobulin (Kirkegaard & Perry Laboratories, Inc., Gaithersburg, Md.) and biotin-labeled anti-pan T-cell antibodies or fluorescein isothiocyanate-labeled anti-CD8 and biotin-labeled anti-CD4 antibodies. Biotin-labeled antibodies were developed with phycoerythrin. Erythrocytes were lysed with fluorescence-activated cell sorter (FACS) lysing solution (Becton Dickinson Immunocytometry Systems, San Jose, Calif.), and the percent positively stained lymphocytes was determined by flow cytometric analysis using a Becton Dickinson FACScan. The absolute numbers for each lymphocyte subset were calculated by multiplying the percent positive cells by the total number of lymphocytes, determined by a complete blood count and differential performed on the blood sample.

PCR-Southern blot analysis for FIV-provirus detection. Percoll-purified PBMCs were washed with PBS, and cell pellets were stored at −70° C. until assayed. Cells ($10^6$) were lysed in 200 µl of 1×PCR buffer and digested with 600 µg of proteinase K per ml. An 838-bp length of the FIV gag region was amplified with the primer set 919U-1756L. Amplification was performed as described previously (English et al., J. Virol. 67:5175 (1993)), with minor modifications. Briefly, 2 µl of cell lysate (equivalent to $10^4$ cells) was amplified in a 100-µl PCR mixture (1×PCR buffer, 1.5 mM $MgCl_2$, 200 µM each deoxynucleoside triphosphate, 0.5 µM each primer, and 2.5 U of Taq DNA polymerase over 40 cycles (one cycle was 94° C. for 1 minute, 59° C. for 2 minutes, and 72° C. for 1 minute, final extension was done at 72° C. for 10 minutes). Amplified products were resolved on a 1.2% agarose gel, blotted, and hybridized with radiolabeled internal oligonucleotides probe.

Western blot analysis for plasma antibody to FIV. The Western blot (immunoblot) assay was performed as described (Novotney et al., AIDS 4:1213 (1990)).

RT activity assay. The $Mg^{2+}$-dependent RT activity assay was performed as described (Novotney et al., AIDS 4:1213 (1990)) and is a modification of a procedure of Goff et al. (Goff et al., J. Virol. 38:239 (1981)).

Lymphocyte subset sorting of feline PBMCs. The JSY3 clone-infected cat PBMCs were sorted into CD4+, CD8+ and B lymphocyte subsets using MiniMACS (Miltenyi Biotec, Sunnyvale, Calif.) magnetic beads. Percoll-enriched PBMCs were divided among three tubes and incubated at 4° C. for 30 minutes with biotin-labeled anti-CD4 or anti-CD8 or anti-canine B-cell MAb (B5) for a non-immunoglobulin-positive B-cell epitope (English et al., J. Virol. 67:5175 (1993)). Streptavidin-conjugated MiniMACS beads were then added, and the cells were incubated for an additional 20 minutes at 4° C. and then positively sorted. A fraction of each sorted subset was analyzed for purity by two-color flow cytometry. Cells were stained with biotin-labeled MAbs, developed with phycoerythrin-conjugated streptavidin, and analyzed on the FACScan. The remaining sorted lymphocytes were stored at −70° C. until they were assayed for the presence of FIV provirus by PCR-Southern blotting.

T. gondii infection. Twenty-nine weeks after infection with the JSY3 clone, cats were inoculated via the carotid artery with 10,000 tachyzoites of the ME49 strain of T. gondii as described (Davidson et al., Am. J. Pathol. 143:1486 (1993)). Six age- and sex-matched SPF cats were also inoculated with T. gondii as controls. The cats were examined daily for clinical signs of illness using scoring criteria (Davidson et al., Am. J. Pathol. 143:1486 (1993)). Cats with severe clinical signs indicative of generalized toxoplasmosis were euthanized by barbiturate overdose.

Postmortem examination. Following euthanasia, a gross necropsy was performed and tissues were sampled for microscopic examination. Tissues were fixed in 10% neutral buffered formalin, embedded in paraffin, sectioned and stained with hematoxylin and eosin stain.

EXAMPLE 2

Molecular Cloning and Sequencing of the JSY3 Proviral Genome

A total of $5 \times 10^7$ FCD4E cells were infected with wild-type FIV-NCSU$_1$ from the FIV-NCSU$_1$ source cat. Genomic DNA from this culture was cloned into the EMBL3 lambda vector arm. Primary hybridization-positive clones, determined by plaque hybridization with a randomly labeled 838 bp FIV gag PCR product probe, were screened further by PCR as described in Example 1. Five microliters of phage plaque suspensions of each hybridization-positive clone was directly amplified with six different primer sets, and a full-length proviral clone was identified (designated JSY3). The specificity of each FIV PCR product was established by comparing it with the FIV-pPPR plasmid clone (Phillips et al., *J. Virol.* 64:4605 (1990)).

The genomic proviral insert was subcloned into pJEM vectors, and the provirus genome was sequenced by primer directed sequencing, using techniques as are known in the art. Nucleotide and predicted amino acid sequences were computer analyzed, and open reading frames (orfs) were identified.

The provirus DNA sequence of the JSY3 provirus clone of FIV-NCSU$_1$ is provided in FIG. 1, with the group specific antigen (gag), polymerase (pol), and envelope protein (env) regions marked. As shown in FIG. 1, the DNA sequence consists of 9471 base pairs (SEQ ID NO:1).

The coding region of gag is nucleotides 631–1980 of SEQ ID NO:1 (SEQ ID NO:4) and encodes a 450 amino acid product (SEQ ID NO:2).

The coding region for the p15 protein is nucleotides 631–1035 of SEQ ID NO:1 (SEQ ID NO:5), with a polypeptide product of 135 amino acids (SEQ ID NO:6).

The coding region for the p25 protein is nucleotides 1036–1704 of SEQ ID NO:1 (SEQ ID NO:7), with a polypeptide product of 223 amino acids (SEQ ID NO:8).

The coding region for the p24a protein is nucleotides 1264–1305 of SEQ ID NO:1 (SEQ ID NO:9), with a polypeptide product of 14 amino acids (SEQ ID NO:10).

The coding region for the p10 protein is nucleotides 1717–1980 of SEQ ID NO:1 (SEQ ID NO:11), with a polypeptide product of 88 amino acids (SEQ ID NO:12).

The coding region of pol is amino acids 2151–5991 of SEQ ID NO:1 (SEQ ID NO:13). Two open reading frames (orfs) are found in the pol region. Orf 1 is nucleotides 2151–5243 of SEQ ID NO:1 (SEQ ID NO:14), encoding a product of 1031 amino acids (SEQ ID NO:15); Orf 2 is nucleotides 5239–5991 of SEQ ID NO:1 (SEQ ID NO:16) and encodes a product of 251 amino acids (SEQ ID NO:17).

The env coding region is nucleotides 6269–8824 of SEQ ID NO:1 (SEQ ID NO:18) and encodes a protein of 852 amino acids (SEQ ID NO:3). The transmembrane (TM) peptide is encoded by nucleotides 8339–8374 of SEQ ID NO:1 (SEQ ID NO:19), and is 12 amino acids in length (SEQ ID NO:20).

FIG. 2 aligns the gag open reading frames of the JSY3 clone of NCSU$_1$ (FIV-NCSU) with known FIV isolates FIV PPR, FIV Z1, FIV CG, FIV 14, FIV TM1, and FIV TM2. FIG. 3 aligns the whole envelope protein sequence of clone JSY3 of NCSU$_1$ with known FIV isolates FIV 14, FIV Z1, FIV CG, FIV 19k, and FIV PPR.

EXAMPLE 3

Biological Activity of JSY3

To determine the biological activity of the JSY3 clone, lambda DNA was transfected into CrFK, AH927, and FCD4E cells, which were then cocultured with FCD4E cells or PBMCs. While no RT activity was detected in culture supernatants of JSY3-transfected CrFK or AH927 cells when cultured alone, RT activity was detected when the transfected cells were cocultured with either PBMCs or FCD4E cells (data not shown). The replication kinetics of FIV in FCD4E cells is more rapid than in PBMCs because of the greater percentage of CD4+ cells in the FCD4E culture. Supernatants collected at 15 and 19 days of culture from FCD4E cells were filtered (0.2 μm pore size) and stored in aliquots for use an in vitro and in vivo inocula. These inocula were designated the FIV-NCSU$_1$-JSY3 clone. No RT activity was detected in the FCD4E cultures directly transfected with JSY3, suggesting that the transfection was unsuccessful (data not shown).

To determine the in vitro infectivity of the JSY3 clone, FCD4E and CrFK cells were inoculated with cell-free JSY3 clone. Similarly to the FIV-NCSU$_1$ wild-type virus (English et al., *J. Virol.* 67:5175 (1993)), the JSY3 clone replicated efficiently in FCD4E cells, resulting in syncytium formation and cell death (data not shown). However, the JSY3 clone was unable to infect CrFK cells.

EXAMPLE 4

In vivo Infectivity of JSY3

To determine the in vivo infectivity of the JSY3 molecular clone, six SPF cats were inoculated intravenously with $10_6$ TCID$_{50}$ of JSY3 clone. Nine age-matched SPF cats were inoculated with $10^6$ TCID$_{50}$s of FIV-NCSU$_1$, also produced in FCD4E cells. Plasma and PBMCs were collected at various times post infection, and tested for antibodies to FIV by Western blotting and tested for cell-associated FIV provirus by PCR. As previously reported (English et al., *J. Infect. Dis.* 170:543 (1994); Tompkins et al., *J. Am. Vet. Med. Assoc.* 199:1311 (1991)) cats infected with FIV-NCSU$_1$ parent virus were anti-FIV positive by 4 weeks post infection and were provirus positive by PCR by 2 weeks post infection (data not shown).

The response of cats infected with the JSY3 clone was similar to that of the cats infected with the wild-type. By four weeks post infection, all six cats had antibody to the FIV gag proteins p17 and p24, and they were still antibody positive at 25 weeks post infection (data not shown). The presence of FIV provirus in PBMCs from six cats infected with the JSY3 clone was determined by PCR and southern analysis. A PBMC lysate (equivalent to $10^4$ cells) was amplified with the gag region primer set 919U-1756L, resolved on an agarose gel, and subjected to Southern blot analysis with a 5'-end-labeled internal probe. Provirus was detected in PBMCs from all cats by two weeks post infection (data not shown). All cats remained provirus positive when the amount of cell lysate in the PCR mixture was increased (data not shown).

To establish the presence of infectious virus in PBMCs from the JSY3-infected cats, PBMCs collected at 6 and 25 weeks post infection were cocultured with FCD4E cells and the supernatants were assayed for RT activity. Syncytium formation and cell death were observed in cocultures from all six cats at both six and 25 weeks p.i. RT activity was detectable in all cocultures by 8 to 10 days and peaked by 16 to 18 days of culture (data not shown).

EXAMPLE 5

Lymphocyte Subset Changes in JSY3-infected Cats

Lymphocyte profiles in naturally and experimentally FIV-infected cats are well documented (Ackley et al., *J. Virol.* 64:5652 (1990); English et al., *J. Infect. Dis.* 170:543 (1994); Hoffmann-Fezer et al., *J. Virol.* 66:1484 (1992);

Novotney et al., *AIDS* 4:1213 (1990); Tompkins et al., *J. Am. Vet. Med. Assoc.* 199:1311 (1991)). To determine whether the JSY3 clone causes hematologic and immunologic abnormalities similar to those of the biological parent FIV-NCSU$_1$, lymphocyte subset profiles were analyzed by two-color flow cytometry. As reported for NCSU$_1$ (English et al., *J. Infect. Dis.* 170:543 (1994); Tompkins et al., *J. Am. Vet. Med. Assoc.* 199:1311 (1991)), both the biological virus and the JSY3 clone caused a panlymphopenia two to four weeks p.i. The parent FIV-NCSU$_1$ and the JSY3 molecular clone caused parallel alterations in the CD4+/CD8+ ratio (data not shown). At six weeks p.i., the mean CD4+/CD8+ cell ratios (± standard errors) decreased from 3.48±0.50 to 1.30±0.21 for the parent virus-infected cats. By using total cell counts and flow cytometric analysis of lymphocyte subsets, the decrease in the CD4+/CD8+ ratio was determined to be the result of a decrease in CD4+ lymphocytes and an increase in CD8+ lymphocytes (data not shown). These results indicate that the JSY3 clone-infected cats have hematologic and immunologic abnormalities, including CD4+ and CD8+ lymphocyte changes similar to those of cats infected with the biological parent virus.

EXAMPLE 6

In vivo Lymphocyte Tropism

The in vivo hematopoietic target cells of FIV isolates, including NCSU$_1$, have been reported to be CD4+, CD8+, monocytes, and B lymphocytes (Beebe et al., *J. Virol.* 68:3080 (1994); Brown et al., *J. Virol.* 65:3359 (1991); English et al., *J. Virol.* 67:5175 (1993)). To determine whether the JSY3 molecular clone has a similar panlymphotropism in vivo, PBMCs from JSY3 clone infected cats were sorted into CD4+, CD8+, and B lymphocyte populations using antibody-coated magnetic beads. Each cell subset was lysed, PCR amplified with the gag region 919U-1756L primer set, and analyzed by Southern blotting. As previously reported for the NCSU$_1$ parent virus, FIV provirus was first detected in CD4+ lymphoctyes during the acute-stage infection with JSY3 (2 to 4 weeks p.i.) (data not shown). At a later stage of infection (as early as 14 weeks p.i.), FIV provirus was found in CD8+ and B lymphocytes in addition to CD4+ lymphocytes, as reported for FIV-NCSU$_1$ (English et al., *J. Virol.* 67:5175 (1993)). All six JSY3-infected cats showed similar shifts in provirus burden from predominately CD4+ cells during the acute-stage infection to predominately B cells during the asymptomatic stage. While CD4+ and CD8+ cells were not always positive for provirus under PCR conditions described in Example 1, provirus was always able to be detected in these cells during the asymptomatic-stage infection by increasing cell numbers or using nested primers as described by English et al., *J. Virol.* 67:5175 (1993). The JSY3 molecular clone, similar to the parent biological isolate, exhibits a CD4+ tropism during the acute-stage infection that then shifts to a panlymphotropism as the infection progresses.

EXAMPLE 7

JSY3-Infected Cats

Acute-stage disease. In the primary phase of infection (2 to 16 weeks p.i.), both the JSY3- and the parent isolate-infected cats developed low-grade fevers, panlymphopenia, neutropenia, and generalized lymphadenopathy (data not shown), as has been reported for a number of biological isolates of FIV (Yamamoto et al., *Am. J. Vet. Res.* 49:1246 (1988)), including NCSU$_1$ (English et al., *J. Infect. Dis.* 170:543 (1994)).

Clinical response of JSY3-infected cats to *T. gondii* challenge. Davidson et al., (*Am. J. Pathol.* 143:1486 (1993)) reported that FIV-NCSU$_1$ causes immune system impairment in cats as early as eighteen weeks after infection and enhances susceptibility to a primary *t. gondii* infection. To determine if the molecular clone JSY3 caused immune impairment early in the asymptomatic stage of infection, the cats were parenterally inoculated with the ME49 strain of *T. gondii* 29 weeks after JSY3 infection. six age-matched SPF control cats were similarly infected with *T. gondii*. At the time of *T. gondii* inoculation, all six FIV-infected cats were clinically normal; however, they had a marked decrease in their CD4+/CD8+ ratios in comparison with preinfection ratios and those of the control cats (data not shown). Only one of six *T. gondii*-infected cats in the non-FIV-inoculated group had positive clinical scores, as a result of anorexia and lethargy on days 8 to 11 after inoculation. Cats in this group also developed multifocal chorioretinitis beginning on days 7 to 10 after inoculation, which resolved over a three week course. The infection was otherwise subclinical in these cats. This clinical response is similar to that previously reported for healthy cats challenged with the mildly virulent ME49 strain of *T. gondii* (Davidson et al., *Invest. Ophthalmol. Visual Sci.* 34:3653 (1993); Davidson et al., *Am. J. Pathol.* 143:1486 (1993)).

Five of the six FIV-positive cats challenged with *t. gondii* had positive clinical scores in all three categories (attitude, appetite, and respiratory signs), and the total scores were higher than those of the *T. gondii* control group. Beginning on days 6 to 9 after inoculation, three FIV-infected cats challenged with *T. gondii* developed high fevers, depression, and moderate to severe ocular lesions, including chorioretinitis with subretinal granuloma formation, localized retinal detachment, and fibrinous anterior uveitis. Severe and progressive tachypnea, dyspnea, tachycardia, and icterus were noted, and interstitial and consolidated lung sounds were auscultated. These three cats were euthanized when moribund on day 9 or 10 after inoculation. Two of the three remaining cats developed mild to moderate clinical toxoplasmosis but recovered. This clinical course of *T. gondii* infection in JSY3 infected cats, including the high morbidity, was similar to that reported by Davidson et al. (*Am. J. Pathol.* 143:1486 (1993)) for cats infected with NCSU$_1$.

Postmortem findings. Postmortem exams were performed on the three FIV-*T.gondii*-infected cats that were euthanized to confirm that their clinical disease was due to toxoplasmosis. One cat had gross evidence of interstitial pneumonia. All three animals had foci of discoloration in the liver consistent with hepatic necrosis, and the hearts contained foci of myocardial necrosis. Histologically, lesions were present in the lungs, livers, hearts, and brains of the three cats, and were similar to those seen in cats with dual FIV-NCSU$_1$-*T. gondii* infection as described by Davidson et al., (*Am. J. Pathol.* 143:1486 (1993)). Except for the heart, *T. gondii* tachyzooites were seen in all tissues examined. The tachyzooites were never numerous but most conspicuous as clusters inside of macrophages in the regions of severe inflammation and necrosis in the brain, lung, and liver.

The foregoing examples are illustrative of the present invention, and are not to be construed as limiting thereof. The invention is defined by the following claims, with equivalents of the claims to be included therein.

That which is claimed is:

1. An isolated DNA molecule consisting of a DNA sequence selected from the group consisting of SEQ ID NO:18 and SEQ ID NO: 19.

2. A vector comprising the molecule of claim 1.

3. A vector according to claim 2, wherein said vector comprises bacteriophage lambda.

4. A host cell containing and capable of expressing a vector according to claim 3.

5. A host cell according to claim 4, wherein said host cell comprises Escherichia coli.

6. A host cell according to claim 4, wherein said host cell comprises a yeast cell.

7. A host cell according to claim 4, wherein said host cell comprises a mammalian host cell.

* * * * *

SEQUENCE LISTING (1) GENERAL INFORMATION:

(iii) NUMBER OF SEQUENCES: 33

(2) INFORMATION FOR SEQ ID NO:1:

(i) SEQUENCE CHARACTERISTICS:
      (A) LENGTH: 9471 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 631..1980

(ix) FEATURE:
      (A) NAME/KEY: CDS
      (B) LOCATION: 6269..8824

(xi) SEQUENCE DESCRIPTION: SEQ ID NO:1:

```
TGGGATGAGT ATTGGGACCC TGAAGAAATA GAAAGAATGC TTATGGACTA GTGACTGTTT      60

ACGAACAAAT GATAAATGAT GGAAACAGCT GAGCATGACT CATAGTTAAA GCGCTAGCAG     120

CTGCTTAACC GCAAAACCAC ATCCTATGTA AAGCTTGCTG ATGACGTATA ATTTGCTCCA     180

CTGTAAAAGT ATATAACCAG TGCTTTGTGA GACTTCGGGG AGTCTCTCCG TTGAGGACTT     240

TCGAGTTCTC CCTTGAGGCT CCCACAGATA CAATAAATAT TTGAGATTGA ACCCTGTCAA     300

GTATCTGTGT AATCTTTTTT ACCTGTGAGG TCTCGGAATC CGGGCCGAGA ACTTCGCAGT     360

TGGCGCCCGA ACAGGGACTT GATTGAGAGT GATTGAGGAA GTGAAGCTAG AGCAATAGAA     420

AGCTGTTAAG CAGAACTCCT GCTGACCTAA ATAGGGAAGC AGTAGCAGAC GCTGCTAACA     480

GTGAGTATCT CTAGTGAAGC AGACTCGAGC TCATAATCAA GTCACTGTTT AAAGGCCCAG     540

ATAAATTACA TCTGGTGACT CTTCGCGGAC CTTCAAGCCA GGAGATTCGC CGAGGGACAG     600

TCAACAAGGT AGGAGAGATT CTGCAGCAAC ATG GGG AAC GGA CAG GGG CGA GAT     654
                                  Met Gly Asn Gly Gln Gly Arg Asp
                                    1               5

TGG AAA ATG GCC ATT AAG AGA TGT AGT AAT GTT GCT GTA GGA GTA GGG      702
Trp Lys Met Ala Ile Lys Arg Cys Ser Asn Val Ala Val Gly Val Gly
    10                  15                  20

GGG AAG AGT AAA AAA TTT GGA GAA GGG AAT TTC AGA TGG GCC ATT AGA      750
Gly Lys Ser Lys Lys Phe Gly Glu Gly Asn Phe Arg Trp Ala Ile Arg
 25                  30                  35                  40

ATG GCT AAT GTA TCT ACA GGA CGA GAA CCT GGT GAT ATA CCA GAG ACT      798
Met Ala Asn Val Ser Thr Gly Arg Glu Pro Gly Asp Ile Pro Glu Thr
                 45                  50                  55

TTA GAT CAA CTA AGG TTG GTT ATT TGC GAT TTA CAA GAA AGA AGA GAA      846
Leu Asp Gln Leu Arg Leu Val Ile Cys Asp Leu Gln Glu Arg Arg Glu
             60                  65                  70

AAA TTT GGG TCG AGC AAA GAA ATT GAC ATG GCA ATT GTT ACA TTA AAA      894
Lys Phe Gly Ser Ser Lys Glu Ile Asp Met Ala Ile Val Thr Leu Lys
         75                  80                  85

GTC TTT GCG GTA GTA GGA CTT TTA AAT ATG ACA GTG TCT ACT GCT GCT      942
Val Phe Ala Val Val Gly Leu Leu Asn Met Thr Val Ser Thr Ala Ala
     90                  95                 100

GCA GCT GAA AAT ATG TAC ACT CAG ATG GGA TTA GAC ACT AGA CCA TCT      990
Ala Ala Glu Asn Met Tyr Thr Gln Met Gly Leu Asp Thr Arg Pro Ser
105                 110                 115                 120
```

-continued

```
ATG AGA GAA GCA GGA GGA AAA GAG GAA AGC CCT CCA CAG GCA TCT CCT        1038
Met Arg Glu Ala Gly Gly Lys Glu Glu Ser Pro Pro Gln Ala Ser Pro
                125                 130                 135

ATT CAA ACA GCA AAT GGA GCA CCA CAA TAT GTA GCA CTT GAC CCA AAA        1086
Ile Gln Thr Ala Asn Gly Ala Pro Gln Tyr Val Ala Leu Asp Pro Lys
            140                 145                 150

ATG GTG TCC ATT TTT ATG GAA AAG GCA AGA GAA GGA TTA GGA GGT GAG        1134
Met Val Ser Ile Phe Met Glu Lys Ala Arg Glu Gly Leu Gly Gly Glu
            155                 160                 165

GAA GTT CAG CTA TGG TTT ACT GCC TTC TCT GCA AAT TTA ACA CCT ACT        1182
Glu Val Gln Leu Trp Phe Thr Ala Phe Ser Ala Asn Leu Thr Pro Thr
170                 175                 180

GAC ATG GCC ACA TTA ATA ATG GCC GCA CCA GGG TGC GCT GCA GAT AAA        1230
Asp Met Ala Thr Leu Ile Met Ala Ala Pro Gly Cys Ala Ala Asp Lys
185                 190                 195                 200

GAA ATA TTG GAT GAA AGC TTA AAG CAA TTG ACG GCA GAG TAT GAT CGT        1278
Glu Ile Leu Asp Glu Ser Leu Lys Gln Leu Thr Ala Glu Tyr Asp Arg
                205                 210                 215

ACC CAT CCT CCT GAT GGA CCT AGA CCA TTA CCC TAT TTT ACT GCA GCA        1326
Thr His Pro Pro Asp Gly Pro Arg Pro Leu Pro Tyr Phe Thr Ala Ala
                220                 225                 230

GAA ATT ATG GGT ATA GGA TTA ACT CAA GAA CAA CAA GCA GAA GCA AGA        1374
Glu Ile Met Gly Ile Gly Leu Thr Gln Glu Gln Gln Ala Glu Ala Arg
            235                 240                 245

TTT GCA CCA GCT AGG ATG CAG TGT AGA GCA TGG TAT CTC GAG GCA CTA        1422
Phe Ala Pro Ala Arg Met Gln Cys Arg Ala Trp Tyr Leu Glu Ala Leu
        250                 255                 260

GGA AAA TTG GCC GCC ATA AAA GCT AAG TCT CCT CGA GCT GTG CAG TTA        1470
Gly Lys Leu Ala Ala Ile Lys Ala Lys Ser Pro Arg Ala Val Gln Leu
265                 270                 275                 280

AGA CAA GGA GCT AAG GAA GAT TAT TCA TCC TTT ATA GAC AGA TTG TTT        1518
Arg Gln Gly Ala Lys Glu Asp Tyr Ser Ser Phe Ile Asp Arg Leu Phe
                285                 290                 295

GCC CAA ATA GAT CAA GAA CAA AAT ACA GCT GAA GTT AAG TTA TAT TTA        1566
Ala Gln Ile Asp Gln Glu Gln Asn Thr Ala Glu Val Lys Leu Tyr Leu
                300                 305                 310

AAA CAG TCA TTA AGC ATG GCT AAT GCT AAT GCA GAA TGT AAA AAG GCA        1614
Lys Gln Ser Leu Ser Met Ala Asn Ala Asn Ala Glu Cys Lys Lys Ala
            315                 320                 325

ATG AGC CAC CTT AAG CCA GAA AGT ACC CTA GAA GAA AAG CTG AGA GCT        1662
Met Ser His Leu Lys Pro Glu Ser Thr Leu Glu Glu Lys Leu Arg Ala
            330                 335                 340

TGT CAA GAA GTA GGC TCA CCA GGA TAT AAA ATG CAA CTC TTG GCA GAA        1710
Cys Gln Glu Val Gly Ser Pro Gly Tyr Lys Met Gln Leu Leu Ala Glu
345                 350                 355                 360

GCT CTT ACA AAA GTT CAA GTA GTG CAA TCA AAA GGA TCA GGA CCA GTG        1758
Ala Leu Thr Lys Val Gln Val Val Gln Ser Lys Gly Ser Gly Pro Val
                365                 370                 375

TGT TTC AAC TGT AAA AAA CCA GGA CAT CTA GCA AAA CAG TGT AGA GAT        1806
Cys Phe Asn Cys Lys Lys Pro Gly His Leu Ala Lys Gln Cys Arg Asp
                380                 385                 390

GTG AAA AAA TGT AAT AAA TGT GGA AAG CCT GGT CAT TTA GCT GCC AAA        1854
Val Lys Lys Cys Asn Lys Cys Gly Lys Pro Gly His Leu Ala Ala Lys
            395                 400                 405

TGC TGG CAA GGT GGT AAA AAG AAT TCG GGA AAC TGG AAG GCG GGG CGA        1902
Cys Trp Gln Gly Gly Lys Lys Asn Ser Gly Asn Trp Lys Ala Gly Arg
        410                 415                 420

GCT GCA GCC CCA GTG AAT CAA GTG CAG CAA GCA GTA ATG CCA TCT GCA        1950
Ala Ala Ala Pro Val Asn Gln Val Gln Gln Ala Val Met Pro Ser Ala
```

```
                425               430               435               440
CCT CCA ATG GAG GAG AGA CTA TTG GAT TTA TAAATTATAA TAAAGTAGGT          2000
Pro Pro Met Glu Glu Arg Leu Leu Asp Leu
                445                         450

ACTACTACAA CATTAGAAAA GAGGCCAGAA ATACTTATAT TTGTAAATGG GTACCCTATA      2060
AAATTTTTAT TAGATACAGG AGCAGATATA ACAATTTTAA ATAGGAGAGA TTTTCAAGTA      2120
AAAAATTCTA TAGAAAATGG AAGGCAAAAT ATGATTGGAG TAGGAGGAGG AAAGAGAGGA      2180
ACAAATTATA TCAATGTGCA TTTAGAGATT AGAGATGAAA ATTATAAGAC ACAATGTATA      2240
TTTGGCAATG TTTGTGTCTT AGAAGATAAC TCATTAATAC AACCATTATT AGGGAGAGAT      2300
AATATGATTA GATTCAATAT TAGGTTAGTA ATGGCTCAAA TTTCTGACAA GATTCCAATA      2360
GTAAAAGTAA AAATGAAGGA TCCAAATAAA GGACCTCAAA TAAAACAATG GCCATTAACA      2420
AATGAAAAAA TTGAAGCTTT AACAGAAATA GTAGAAAGAC TAGAAAGAGA AGGGAAAGTA      2480
AAAAGAGCAG ATCCAAATAA CCCATGGAAT ACACCAGTAT TTGCAATAAA AAAGAAAAGT      2540
GGAAAATGGA GAATGCTCAT AGATTTTAGA GAATTGAACA AATTAACTGA AAAGGGGCA      2600
GAAGTCCAGT TAGGACTCCC TCATCCTGCT GGATTAAAAA TGAAAAAACA AGTTACTGTG      2660
CTAGATATAG GAGATGCATA CTTCACTATT CCCTTGGATC CAGACTATGC TCCCTATACT      2720
GCATTCACAT TACCTAGAAA GAATAATGCA GGACCAGGGA GGAGATATGT ATGGTGCAGT      2780
TTACCACAGG GGTGGGTTCT AAGCCCATTG ATATATCAAA GTACTTTAGA TAATATAATA      2840
CAACCTTTTA TTAGACAAAA TCCTGAGTTA GATATTTATC AATATATGGA TGACATTTAT      2900
ATAGGATCAA ACTTAAGTAA AAAGGAGCAT AAAGAAAAAG TAGAAGAATT AAGAAAATTG      2960
TTATTATGGT GGGGATTTGA AACCCCGGAA GACAAATTAC AAGAAGAGCC CCCATATAAG      3020
TGGATGGGCT ATGAATTACA TCCATTAACA TGGTCAATAC AGCAAAAACA ATTAGAAATT      3080
CCAGAAAGAC CCACATTAAA TGAACTGCAG AAATTAGCAG GTAAGATAAA CTGGGCCAGT      3140
CAAACTATCC CAGACTTAAG TATAAAAGAA CTAACTAACA TGATGAGAGG AGATCAGAAG      3200
TTAGACTCAA TAAGAGAATG GACTGTGGAA GCCAAGAGAA AGTACAAAA AGCTAAGGAA      3260
GCTATTGAGA TGCAAGCACA GCTAAATTAT TATGATCCCC ACCGAGAATT ATATGCAAAA      3320
TTAAGTTTAG TGGGACCACA TCAAATATGT TATCAAGTGT ATCATAAGAA CCAGAATGT      3380
ATTTTATGGT ATGGTAAGAT GAATAGACAA AAGAAAAAGG CAGAAAATAC CTGTGATATA      3440
GCTCTAAGGG CATGTTATAA AATAAGAGAA GAATCTATTA TAAGAATAGG AAAAGAACCA      3500
ATATATGAAA TACCTACTTC TAGAGAAGCC TGGGAGTCAA ATTTAATTAA TTCACCATAT      3560
CTTAAGGCCC CACCTCCTGA GGTAGAATAT ATCCATGCTG CTGTGAATAT AAAAAGAGCA      3620
TTAAGTATGA TAAAAGATGT TCCAATACCA GAAGCAGAAA CGTGGTATAT AGATGGAGGC      3680
AGAAAGCTAG GAAAAGCAGC AAAAGCAGCC TATTGGACAG ATACAGGGAA GTGGCAAGTA      3740
ATGGAGTTAG AAGGCAGTAA TCAGAAGGCA GAAGTACAAG CATTATTATT GGCATTAAAA      3800
GCAGGATCAG AGGAAATGAA TATTATAACA GATTCACAAT ATGTTATAAA TATTATTCTT      3860
CAACAACCAG ATATGATGGA GGGAATCTGG CAAGAAGTTT TAGAAGAATT GGAGAAAAAA      3920
ACAGCAATAT TTATAGATTG GGTCCCAGGA CATAAAGGTA TTCCAGGAAA TGAGGAAGTA      3980
GATAAGCTTT GTCAAACAAT GATGATAATA GAAGGGGATG GGATATTAGA TAAAAGGTCA      4040
GAAGATGCGG GATATGATTT ATTGGCTGCA AAAGAAATAC ATTTATTGCC AGGAGAGGTA      4100
AAAGTAATAC CAACAGGGGT AAAGCTAATG CTGCCTAAAG GACATTGGGG ACTAATAATG      4160
GGAAGAAGCT CGATAGGGAG TAAAGGATTG GATGTATTAG GAGGGTAAT AGATGAAGGA      4220
```

```
TATCGAGGTG AAATTGGAGT AATAATGATT AATGTATCAA GAAAATCAAT CACCTTAATG    4280

GAACAACAAA AGATAGCACA ATTAATAATA TTGCCTTGTA ACATGAAGT ATTAGAACAA     4340

GGAAAAGTTG TAATGGATTC AGAGAGAGGA GACAAAGGTT ATGGGTCAAC AGGAGTATTC    4400

TCCTCTTGGG TTGACAGGAT TGAGGAAGCA GAAATAAATC ATGAAAAATT TCACTCAGAT    4460

CCACAATACT TAAGGACTGA ATTTAATTTA CCCAAGATGG TTGCAGAAGA GATAAGACGA    4520

AAGTGCCCTG TATGTAGAAT CAGAGGAGAA CAAGTGGGAG GACAATTGAA AATAGGGCCT    4580

GGAATATGGC AAGTGGATTG CACACACTTT AATAGTAAGA TAATCATTGT AGCAGTACAT    4640

GTGGAATCAG GATTTTTATG GGCACAGATA ATTCCACAGG AGACTGCAGA TTGTACAGTC    4700

AAGGCTCTTC TGCAACTTAT ATGTGCTCAT AATGTTACAG AATTACAAAC AGACAATGGA    4760

CCAAATTTTA AAAATCAGAA AATGGAAGGT TTATTAAATT TTATGGGAAT AAAACATAAA    4820

TTAGGGATAC CAGGTAACCC ACAATCACAG GCATTAGTGG AAAATGCTAA TAACACATTA    4880

AAAGCTTGGA TTCAAAAATT CCTACCAGAG ACTACCTCTC TGGATAATGC TCTGGCCCTA    4940

GCCCTGTATA GTCTCAACTT TAAACAAAGG GGTAGACTAG GAAGGATGGC CCCTTATGAA    5000

TTATACATAC AACAAGAATC ATTAAGAATA CAAGACTATT TTTCGCAGAT TCCACAAAAG    5060

TTAATGATGC AGTGGGTGTA TTACAAAGAT CAAAAAGACA AAAAATGGAA GGGACCAATG    5120

AGAGTGGAAT ATTGGGACA GGATCAGTA TTATTAAAGG ATGAAGAGAA GGGATATTTT     5180

CTTGTACCTA GGAGACACAT AAGAAGAGTC CCAGAACCCT GCACTCTTCC TGAAGGGGAT    5240

GAGTGACGAA GATTGGCAGG TAAGTAGAAG ACTCTTTGCA GTGCTCCAAG GAGGAGTACG    5300

TAGTGCTATG CTATACATAT CTAGACTACC TCCGGACGAA AGAGAAAGGT ATAAAAAAGA    5360

CTTTAAGAAA AGGCTTTTGG AAAAGGAAAC AGGATTCATA CAGAGATTAA GAAAAGCGGA    5420

AGGAATAAGG TGGAGCTTCC ATACTAGAGA TTATTATATA GGATATGTAA GAGAGATGGT    5480

GGCCGGATCT AGTCTACCAG ATAGTTTAAG ACTGTATATT TATATAAGCA ATCCATTGTG    5540

GCACTGGTCA TACCGTCCTG GCCTGACAAA TTTTAATACA GAATGGCCTT TTGTGAATAT    5600

GTGGATAAAG ACAGGATTCA TGTGGGATGA TATTGAAAGC CAGAATATTT GCAAAGGAGG    5660

AGAGATTTCA CATGGATGGG GACCTGGAAT GGTGGGAATT GTGATAAAAG CTTTTAGTTG    5720

TGGAGAAAGA AAGATTGAGG CTACTCCTGT AATGATTATA AGAGGAGAAA TAGATCCAAA    5780

AAAATGGTGT GGAGATTGTT GGAATTTGAT GTGTCTTAGG AACTCACCTC CACAGACTTT    5840

ACAAAGACTT GCTATGTTGG CATGTGGCGT GCCGGCTAAG GAGTGGCGAG GATGCTGTAA    5900

TCAACGCTTT GTTTCTCCTT ACAGAACGCC TGCTGATTTG GAGGTCATTC AATCCAAGCC    5960

CAGCTGGAGT CTATTATGGT CAGGGAGCCT ATGAATGGAA GACATACTAA CATTATTTAA    6020

TAAGGTCACT AAGAAACTAG AAAAGGAAAA AGCTATCAGA ATATTTGTAT TAGCACATCA    6080

ATTAGAAAGG GACAAAGTTA TTAGATTACT ACAAGGATTA GTTGGAGAC ATAGATTTAA     6140

GAAACCCCAA ACAAAATACT GTTTATGTTG GTTCTGTTGC AAATTCTACT ATTGGCAGTT    6200

GCAATCTACA TTATCAATAA CTACTGCTTA GAAATACTTA ATAATATATT TCATTTGCAA    6260

CAATAATT ATG GCA GAA GGA TTT GCA GCC AAT AGA CAA TGG ATA GGA CCA    6310
         Met Ala Glu Gly Phe Ala Ala Asn Arg Gln Trp Ile Gly Pro
           1               5                  10

GAA GAA GCT GAA GAG TTA TTA GAT TTT GAT ATA GCA ACA CAA ATG AAT    6358
Glu Glu Ala Glu Glu Leu Leu Asp Phe Asp Ile Ala Thr Gln Met Asn
 15                  20                  25                  30

GAA GAA GGG CCA CTA AAT CCA GGG ATG AAC CCA TTT AGG GTA CCT GGA    6406
Glu Glu Gly Pro Leu Asn Pro Gly Met Asn Pro Phe Arg Val Pro Gly
```

```
                        35                      40                      45
ATA ACA GAT AAA GAA AAG CAA GAC TAT TGT AAC ATA TTA CAA CCT AAG          6454
Ile Thr Asp Lys Glu Lys Gln Asp Tyr Cys Asn Ile Leu Gln Pro Lys
                50                      55                      60

TTA CAA GAT TTA CGG AAT GAA CTT CAA GAG GTA AAA CTA GAA GAA GGA          6502
Leu Gln Asp Leu Arg Asn Glu Leu Gln Glu Val Lys Leu Glu Glu Gly
                65                      70                      75

AAT GCA GGT AAG TTT AGA AGG GCA AGA TAT TTA AGA TAT TCT GAT GAA          6550
Asn Ala Gly Lys Phe Arg Arg Ala Arg Tyr Leu Arg Tyr Ser Asp Glu
        80                      85                      90

AAT GTG CTA TCT ATA GTC TAT TTG CTA ATA GGA TAT CTA AGA TAT TTA          6598
Asn Val Leu Ser Ile Val Tyr Leu Leu Ile Gly Tyr Leu Arg Tyr Leu
95                      100                     105                 110

ATA AAT CGT AGG AGT TTA GGA TCT TTA AGA CAT GAT ATA GAC ATA GAA          6646
Ile Asn Arg Arg Ser Leu Gly Ser Leu Arg His Asp Ile Asp Ile Glu
                115                     120                     125

ACA CCT CAA GAG GAA TAT TAT AGT AAT AGT GAA AGG GGT ACC ACA TTA          6694
Thr Pro Gln Glu Glu Tyr Tyr Ser Asn Ser Glu Arg Gly Thr Thr Leu
                130                     135                     140

AAT CAA AAA TAT GCG AGA AGA TGT TGT GTT AGC ACA CTT ATT ATG TAT          6742
Asn Gln Lys Tyr Ala Arg Arg Cys Cys Val Ser Thr Leu Ile Met Tyr
                145                     150                     155

TTA ATT CTT TTT GCA GTA GGC ATC TGG TGG GGA GCT AGA GCA CAA GTA          6790
Leu Ile Leu Phe Ala Val Gly Ile Trp Trp Gly Ala Arg Ala Gln Val
        160                     165                     170

GTG TGG AGA CTT CCC CCT TTA GTA GTT CCA GTA GAA GAA TCA GAA ATA          6838
Val Trp Arg Leu Pro Pro Leu Val Val Pro Val Glu Glu Ser Glu Ile
175                     180                     185                 190

ATT TTT TGG GAT TGT TGG GCA CCA GAA GAA CCC GCC TGT CAA GAC TTT          6886
Ile Phe Trp Asp Cys Trp Ala Pro Glu Glu Pro Ala Cys Gln Asp Phe
                195                     200                     205

CTT GGG GCA ATG ATA CAT CTA AAA GCT AGT ACG AAT ATA AGT ATA CAA          6934
Leu Gly Ala Met Ile His Leu Lys Ala Ser Thr Asn Ile Ser Ile Gln
                210                     215                     220

GAG GGA CCT ACC TTG GGG AAT TGG GCT AGA GAA ATA TGG GGA ACA TTA          6982
Glu Gly Pro Thr Leu Gly Asn Trp Ala Arg Glu Ile Trp Gly Thr Leu
                225                     230                     235

TTC AAA AAG GCT ACC AGA CAA TGT AGA AGA GGT AGA ATA TGG AAA AGA          7030
Phe Lys Lys Ala Thr Arg Gln Cys Arg Arg Gly Arg Ile Trp Lys Arg
        240                     245                     250

TGG AAT GAA ACT ATA ACA GGA CCA TTA GGA TGT GCT AAT AAC ACA TGT          7078
Trp Asn Glu Thr Ile Thr Gly Pro Leu Gly Cys Ala Asn Asn Thr Cys
255                     260                     265                 270

TAT AAT ATT TCA GTA ATA GTA CCT GAT TAT CAA TGT TAT CTA GAC CGA          7126
Tyr Asn Ile Ser Val Ile Val Pro Asp Tyr Gln Cys Tyr Leu Asp Arg
                275                     280                     285

GTA GAT ACT TGG TTA CAA GGG AAA GTA AAT ATA TCA TTA TGT CTA ACA          7174
Val Asp Thr Trp Leu Gln Gly Lys Val Asn Ile Ser Leu Cys Leu Thr
                290                     295                     300

GGA GGA AAA ATG TTG TAC AAT AAA TAT ACA AAA CAA TTA AGC TAT TGT          7222
Gly Gly Lys Met Leu Tyr Asn Lys Tyr Thr Lys Gln Leu Ser Tyr Cys
                305                     310                     315

ACA GAC CCA TTA CAA ATC CCA CTG ATC AAT TAT ACA TTT GGA CCT AAT          7270
Thr Asp Pro Leu Gln Ile Pro Leu Ile Asn Tyr Thr Phe Gly Pro Asn
        320                     325                     330

CAA ACA TGT ATG TGG AAC ACT TCA CAA ATT CAG GAC CCT GAG ATA CCA          7318
Gln Thr Cys Met Trp Asn Thr Ser Gln Ile Gln Asp Pro Glu Ile Pro
335                     340                     345                 350

AAA TGT GGA TGG TGG AAT CAA AGA GCC TAT TAT AAA AAT TGT AAA TGG          7366
```

| | | | | | | | | | | | | |
|---|---|---|---|---|---|---|---|---|---|---|---|---|
| Lys | Cys | Gly | Trp | Trp | Asn | Gln | Arg | Ala | Tyr | Tyr | Lys | Asn | Cys | Lys | Trp |
| | | | 355 | | | | | 360 | | | | 365 | | | |

```
GAA AAA ACA GAT GTA AAG TTT CAT TGT CAA AGA ACA CAG AGT CAG CCT      7414
Glu Lys Thr Asp Val Lys Phe His Cys Gln Arg Thr Gln Ser Gln Pro
            370                 375                 380

GGA ACA TGG CTT AGA GCA ATC TCG TCA TGG AGA CAA AGG AAT AGA TGG      7462
Gly Thr Trp Leu Arg Ala Ile Ser Ser Trp Arg Gln Arg Asn Arg Trp
        385                 390                 395

GAA TGG AGA CCA GAT TTT GAA AGT GAA AAG GTG AAA ATA TCT CTA AAG      7510
Glu Trp Arg Pro Asp Phe Glu Ser Glu Lys Val Lys Ile Ser Leu Lys
    400                 405                 410

TGT AAT AGC ACA AAA AAC CTA ACC TTT GCA ATG AGA AGT TCA GGA GAT      7558
Cys Asn Ser Thr Lys Asn Leu Thr Phe Ala Met Arg Ser Ser Gly Asp
415                 420                 425                 430

TAT GGA GAA GTA ACG GGA GCT TGG ATA GAG TTT GGA TGT CAT AGA AAT      7606
Tyr Gly Glu Val Thr Gly Ala Trp Ile Glu Phe Gly Cys His Arg Asn
                435                 440                 445

AAA TCA AAA CTT CAT GAT GAA GCA AGG TTT AGA ATT AGA TGT AGA TGG      7654
Lys Ser Lys Leu His Asp Glu Ala Arg Phe Arg Ile Arg Cys Arg Trp
            450                 455                 460

AAT ATA GGG GAG AAT ACC TCA CTC ATT GAT ACA TGT GGA AAC ACT CAA      7702
Asn Ile Gly Glu Asn Thr Ser Leu Ile Asp Thr Cys Gly Asn Thr Gln
        465                 470                 475

AAT GTT TCA GGG GCA AAT CCT GTA GAT TGT ACC ATG TAT GCA AAT AAA      7750
Asn Val Ser Gly Ala Asn Pro Val Asp Cys Thr Met Tyr Ala Asn Lys
    480                 485                 490

ATG TAC AAT TGT TCT TTA CAA AAC GGG TTT ACT ATG AAG GTA GAT GAC      7798
Met Tyr Asn Cys Ser Leu Gln Asn Gly Phe Thr Met Lys Val Asp Asp
495                 500                 505                 510

CTT ATT ATG CAT TTC AAT ATG ACA AAA GCT GTA GAA ATG TAT AAT ATT      7846
Leu Ile Met His Phe Asn Met Thr Lys Ala Val Glu Met Tyr Asn Ile
                515                 520                 525

GCT GGA AAT TGG TCT TGT ACA TCT GAC TTG CCA CCA ACA TGG GGG TAT      7894
Ala Gly Asn Trp Ser Cys Thr Ser Asp Leu Pro Pro Thr Trp Gly Tyr
            530                 535                 540

ATG AAT TGT AAC TGT ACA AAT AAT AGT AAT GAT AAT ACT AGA ATG GCA      7942
Met Asn Cys Asn Cys Thr Asn Asn Ser Asn Asp Asn Thr Arg Met Ala
        545                 550                 555

TGT CCT AAC AAT CAA GGC ATC TTA AGG AAT TGG TAT AAC CCA GTA GCA      7990
Cys Pro Asn Asn Gln Gly Ile Leu Arg Asn Trp Tyr Asn Pro Val Ala
    560                 565                 570

GGA TTA CGA CAA TCC TTG GAA AAG TAT CAA GTT GTA AAA CAA CCA GAT      8038
Gly Leu Arg Gln Ser Leu Glu Lys Tyr Gln Val Val Lys Gln Pro Asp
575                 580                 585                 590

TAC TTA GTG GTC CCA GGG GAA GTC ATG GAA TAT AAA ACT AGA AGG AAA      8086
Tyr Leu Val Val Pro Gly Glu Val Met Glu Tyr Lys Thr Arg Arg Lys
                595                 600                 605

AGG GCA GCT ATT CAT GTT ATG TTA GCT CTT GCA ACA GTA TTA TCT ATG      8134
Arg Ala Ala Ile His Val Met Leu Ala Leu Ala Thr Val Leu Ser Met
            610                 615                 620

GCC GGA GCA GGG ACG GGG GCT ACT GCT ATA GGG ATG GTA ACA CAA TAT      8182
Ala Gly Ala Gly Thr Gly Ala Thr Ala Ile Gly Met Val Thr Gln Tyr
        625                 630                 635

CAC CAA GTT CTA GCA ACC CAT CAA GAA GCT ATT GAA AAG GTG ACT GAA      8230
His Gln Val Leu Ala Thr His Gln Glu Ala Ile Glu Lys Val Thr Glu
    640                 645                 650

GCC TTA AAG ATA AAC AAC TTG AGA TTA GTT ACA TTA GAG CAT CAA GTA      8278
Ala Leu Lys Ile Asn Asn Leu Arg Leu Val Thr Leu Glu His Gln Val
655                 660                 665                 670
```

```
CTA GTA ATA GGA TTA AAA GTA GAA GCT ATG GAA AAA TTT TTA TAT ACA              8326
Leu Val Ile Gly Leu Lys Val Glu Ala Met Glu Lys Phe Leu Tyr Thr
                675                 680                 685

GCT TTC GCT ATG CAA GAA TTA GGA TGT AAT CAA AAT CAA TTC TTC TGC              8374
Ala Phe Ala Met Gln Glu Leu Gly Cys Asn Gln Asn Gln Phe Phe Cys
            690                 695                 700

AAA GTC CCT CCT GAA TTG TGG ATG AGG TAT AAT ATG TCT ATA AAT CAA              8422
Lys Val Pro Pro Glu Leu Trp Met Arg Tyr Asn Met Ser Ile Asn Gln
        705                 710                 715

ACA ATA TGG AAT CAT GGA AAT ATA ACT TTG GGG GAA TGG TAT AAC CAA              8470
Thr Ile Trp Asn His Gly Asn Ile Thr Leu Gly Glu Trp Tyr Asn Gln
    720                 725                 730

ACA AAA GAT TTA CAA CAA AAG TTT TAT GAA ATA ATA ATG GAC ATA GAA              8518
Thr Lys Asp Leu Gln Gln Lys Phe Tyr Glu Ile Ile Met Asp Ile Glu
735                 740                 745                 750

CAA AAT AAT GTA CAA GGG AAA AAA GGG ATA CAA CAA TTA CAA AAG TGG              8566
Gln Asn Asn Val Gln Gly Lys Lys Gly Ile Gln Gln Leu Gln Lys Trp
                755                 760                 765

GAA GAT TGG GTA GGA TGG ATA GGA AAT ATT CCA CAA TAC TTA AAG GGA              8614
Glu Asp Trp Val Gly Trp Ile Gly Asn Ile Pro Gln Tyr Leu Lys Gly
            770                 775                 780

CTA TTG GGA GGT ATC TTG GGA ATA GGA TTA GGA GTG TTA TTA TTA ATT              8662
Leu Leu Gly Gly Ile Leu Gly Ile Gly Leu Gly Val Leu Leu Leu Ile
        785                 790                 795

TTA TGT TTA CCC ACA TTG GTT GAT TGT ATA AGA AAT TGT ATC CAC AAG              8710
Leu Cys Leu Pro Thr Leu Val Asp Cys Ile Arg Asn Cys Ile His Lys
    800                 805                 810

ATA CTA GGA TAC ACA GTA ATT GCA ATG CCT GAA GTA GAA GGA GAA GAA              8758
Ile Leu Gly Tyr Thr Val Ile Ala Met Pro Glu Val Glu Gly Glu Glu
815                 820                 825                 830

ATA CAA CCA CAA ATG GAA TTG AGG AGA AAT GGT AGG CAA TGT GGC ATA              8806
Ile Gln Pro Gln Met Glu Leu Arg Arg Asn Gly Arg Gln Cys Gly Ile
                835                 840                 845

TCT GAA AAA GAG GAG GAA TGATGAAGTA TCTCAGACTT ATTTTATAAG                     8854
Ser Glu Lys Glu Glu Glu
            850

GGAGATGCTG TGCTGAGTTC TTCCCTTTGA GGAAGGTATG TCATATGAAT CCATTTCAAA            8914

TCAAATTAAA CTAATAAAGT ATGTATTATA AGGTAAAAAG AAAAAAAGAC AAAGAAGAAG            8974

AAGAAGGAAG AAAGCCTTCA AGAATATGAT GACAGCTTTA AGAGATCGCT TTAGAAAGCT            9034

ATTTGGCACA AATTCTACAA CGGGAGACAG TACAGTGGAA TCTGACGATG AACCTCCTAA            9094

AAAAGAAAAA AGGGTGGACT GGGATGAGTA TTGGGACCCT GAAGAAATAG AAAGAATGCT            9154

TATGGACTAG TGACTGTTTA CGAACAAATG ATAAATGATG GAAACAGCTG AGCATGACTC            9214

ATAGTTAAAG CGCTAGCAGC TGCTTAACCG CAAAACCACA TCCTATGTAA AGCTTGCTGA            9274

TGACGTATAA TTTGCTCCAC TGTAAAAGTA TATAACCAGT GCTTTGTGAG ACTTCGGGGA            9334

GTCTCTCCGT TGAGGACTTT CGAGTTCTCC CTTGAGGCTC CCACAGATAC AATAAATATT            9394

TGAGATTGAA CCCTGTCAAG TATCTGTGTA ATCTTTTTTA CCTGTGAGGT CTCGGAATCC            9454

GGGCCGAGAA CTTCGCA                                                          9471
```

(2) INFORMATION FOR SEQ ID NO:2:

(i) SEQUENCE CHARACTERISTICS:
        (A) LENGTH: 450 amino acids
        (B) TYPE: amino acid
        (D) TOPOLOGY: linear (ii) MOLECULE TYPE: protein (xi) SEQUENCE DESCRIPTION: SEQ ID NO:2:

Met Gly Asn Gly Gln Gly Arg Asp Trp Lys Met Ala Ile Lys Arg Cys
1               5                   10                  15

Ser Asn Val Ala Val Gly Val Gly Lys Ser Lys Lys Phe Gly Glu
            20                  25                  30

Gly Asn Phe Arg Trp Ala Ile Arg Met Ala Asn Val Ser Thr Gly Arg
        35                  40                  45

Glu Pro Gly Asp Ile Pro Glu Thr Leu Asp Gln Leu Arg Leu Val Ile
    50                  55                  60

Cys Asp Leu Gln Glu Arg Arg Glu Lys Phe Gly Ser Ser Lys Glu Ile
65                  70                  75                  80

Asp Met Ala Ile Val Thr Leu Lys Val Phe Ala Val Val Gly Leu Leu
                85                  90                  95

Asn Met Thr Val Ser Thr Ala Ala Ala Glu Asn Met Tyr Thr Gln
            100                 105                 110

Met Gly Leu Asp Thr Arg Pro Ser Met Arg Glu Ala Gly Gly Lys Glu
        115                 120                 125

Glu Ser Pro Pro Gln Ala Ser Pro Ile Gln Thr Ala Asn Gly Ala Pro
    130                 135                 140

Gln Tyr Val Ala Leu Asp Pro Lys Met Val Ser Ile Phe Met Glu Lys
145                 150                 155                 160

Ala Arg Glu Gly Leu Gly Gly Glu Val Gln Leu Trp Phe Thr Ala
            165                 170                 175

Phe Ser Ala Asn Leu Thr Pro Thr Asp Met Ala Thr Leu Ile Met Ala
        180                 185                 190

Ala Pro Gly Cys Ala Ala Asp Lys Glu Ile Leu Asp Glu Ser Leu Lys
    195                 200                 205

Gln Leu Thr Ala Glu Tyr Asp Arg Thr His Pro Pro Asp Gly Pro Arg
210                 215                 220

Pro Leu Pro Tyr Phe Thr Ala Glu Ile Met Gly Ile Gly Leu Thr
225                 230                 235                 240

Gln Glu Gln Gln Ala Glu Ala Arg Phe Ala Pro Ala Arg Met Gln Cys
            245                 250                 255

Arg Ala Trp Tyr Leu Glu Ala Leu Gly Lys Leu Ala Ala Ile Lys Ala
        260                 265                 270

Lys Ser Pro Arg Ala Val Gln Leu Arg Gln Gly Ala Lys Glu Asp Tyr
    275                 280                 285

Ser Ser Phe Ile Asp Arg Leu Phe Ala Gln Ile Asp Gln Glu Gln Asn
    290                 295                 300

Thr Ala Glu Val Lys Leu Tyr Leu Lys Gln Ser Leu Ser Met Ala Asn
305                 310                 315                 320

Ala Asn Ala Glu Cys Lys Lys Ala Met Ser His Leu Lys Pro Glu Ser
            325                 330                 335

Thr Leu Glu Glu Lys Leu Arg Ala Cys Gln Glu Val Gly Ser Pro Gly
        340                 345                 350

Tyr Lys Met Gln Leu Leu Ala Glu Ala Leu Thr Lys Val Gln Val Val
    355                 360                 365

Gln Ser Lys Gly Ser Gly Pro Val Cys Phe Asn Cys Lys Lys Pro Gly
    370                 375                 380

His Leu Ala Lys Gln Cys Arg Asp Val Lys Lys Cys Asn Lys Cys Gly
385                 390                 395                 400

Lys Pro Gly His Leu Ala Ala Lys Cys Trp Gln Gly Gly Lys Lys Asn

```
                    405                 410                 415
Ser Gly Asn Trp Lys Ala Gly Arg Ala Ala Pro Val Asn Gln Val
                420                 425                 430

Gln Gln Ala Val Met Pro Ser Ala Pro Pro Met Glu Glu Arg Leu Leu
            435                 440                 445

Asp Leu
    450

(2) INFORMATION FOR SEQ ID NO:3:

(i) SEQUENCE CHARACTERISTICS:
        (A) LENGTH: 852 amino acids
        (B) TYPE: amino acid
        (D) TOPOLOGY: linear (ii) MOLECULE TYPE: protein (xi) SEQUENCE DESCRIPTION: SEQ ID NO:3:

Met Ala Glu Gly Phe Ala Ala Asn Arg Gln Trp Ile Gly Pro Glu Glu
  1               5                  10                  15

Ala Glu Leu Leu Asp Phe Asp Ile Ala Thr Gln Met Asn Glu Glu
             20                  25                  30

Gly Pro Leu Asn Pro Gly Met Asn Pro Phe Arg Val Pro Gly Ile Thr
         35                  40                  45

Asp Lys Glu Lys Gln Asp Tyr Cys Asn Ile Leu Gln Pro Lys Leu Gln
 50                  55                  60

Asp Leu Arg Asn Glu Leu Gln Glu Val Lys Leu Glu Glu Gly Asn Ala
 65                  70                  75                  80

Gly Lys Phe Arg Arg Ala Arg Tyr Leu Arg Tyr Ser Asp Glu Asn Val
                 85                  90                  95

Leu Ser Ile Val Tyr Leu Leu Ile Gly Tyr Leu Arg Tyr Leu Ile Asn
            100                 105                 110

Arg Arg Ser Leu Gly Ser Leu Arg His Asp Ile Asp Ile Glu Thr Pro
        115                 120                 125

Gln Glu Glu Tyr Tyr Ser Asn Ser Glu Arg Gly Thr Thr Leu Asn Gln
    130                 135                 140

Lys Tyr Ala Arg Arg Cys Cys Val Ser Thr Leu Ile Met Tyr Leu Ile
145                 150                 155                 160

Leu Phe Ala Val Gly Ile Trp Trp Gly Ala Arg Ala Gln Val Val Trp
                165                 170                 175

Arg Leu Pro Pro Leu Val Val Pro Val Glu Glu Ser Glu Ile Ile Phe
            180                 185                 190

Trp Asp Cys Trp Ala Pro Glu Glu Pro Ala Cys Gln Asp Phe Leu Gly
        195                 200                 205

Ala Met Ile His Leu Lys Ala Ser Thr Asn Ile Ser Ile Gln Glu Gly
    210                 215                 220

Pro Thr Leu Gly Asn Trp Ala Arg Glu Ile Trp Gly Thr Leu Phe Lys
225                 230                 235                 240

Lys Ala Thr Arg Gln Cys Arg Arg Gly Arg Ile Trp Lys Arg Trp Asn
                245                 250                 255

Glu Thr Ile Thr Gly Pro Leu Gly Cys Ala Asn Asn Thr Cys Tyr Asn
            260                 265                 270

Ile Ser Val Ile Val Pro Asp Tyr Gln Cys Tyr Leu Asp Arg Val Asp
        275                 280                 285

Thr Trp Leu Gln Gly Lys Val Asn Ile Ser Leu Cys Leu Thr Gly Gly
    290                 295                 300
```

```
Lys Met Leu Tyr Asn Lys Tyr Thr Lys Gln Leu Ser Tyr Cys Thr Asp
305                 310                 315                 320

Pro Leu Gln Ile Pro Leu Ile Asn Tyr Thr Phe Gly Pro Asn Gln Thr
            325                 330                 335

Cys Met Trp Asn Thr Ser Gln Ile Gln Asp Pro Glu Ile Pro Lys Cys
                340                 345                 350

Gly Trp Trp Asn Gln Arg Ala Tyr Tyr Lys Asn Cys Lys Trp Glu Lys
                355                 360                 365

Thr Asp Val Lys Phe His Cys Gln Arg Thr Gln Ser Gln Pro Gly Thr
            370                 375                 380

Trp Leu Arg Ala Ile Ser Ser Trp Arg Gln Arg Asn Arg Trp Glu Trp
385                 390                 395                 400

Arg Pro Asp Phe Glu Ser Glu Lys Val Lys Ile Ser Leu Lys Cys Asn
                405                 410                 415

Ser Thr Lys Asn Leu Thr Phe Ala Met Arg Ser Ser Gly Asp Tyr Gly
            420                 425                 430

Glu Val Thr Gly Ala Trp Ile Glu Phe Gly Cys His Arg Asn Lys Ser
            435                 440                 445

Lys Leu His Asp Glu Ala Arg Phe Arg Ile Arg Cys Arg Trp Asn Ile
            450                 455                 460

Gly Glu Asn Thr Ser Leu Ile Asp Thr Cys Gly Asn Thr Gln Asn Val
465                 470                 475                 480

Ser Gly Ala Asn Pro Val Asp Cys Thr Met Tyr Ala Asn Lys Met Tyr
                485                 490                 495

Asn Cys Ser Leu Gln Asn Gly Phe Thr Met Lys Val Asp Asp Leu Ile
                500                 505                 510

Met His Phe Asn Met Thr Lys Ala Val Glu Met Tyr Asn Ile Ala Gly
            515                 520                 525

Asn Trp Ser Cys Thr Ser Asp Leu Pro Pro Thr Trp Gly Tyr Met Asn
            530                 535                 540

Cys Asn Cys Thr Asn Asn Ser Asn Asp Asn Thr Arg Met Ala Cys Pro
545                 550                 555                 560

Asn Asn Gln Gly Ile Leu Arg Asn Trp Tyr Asn Pro Val Ala Gly Leu
                565                 570                 575

Arg Gln Ser Leu Glu Lys Tyr Gln Val Val Lys Gln Pro Asp Tyr Leu
            580                 585                 590

Val Val Pro Gly Glu Val Met Glu Tyr Lys Thr Arg Arg Lys Arg Ala
            595                 600                 605

Ala Ile His Val Met Leu Ala Leu Ala Thr Val Leu Ser Met Ala Gly
610                 615                 620

Ala Gly Thr Gly Ala Thr Ala Ile Gly Met Val Thr Gln Tyr His Gln
625                 630                 635                 640

Val Leu Ala Thr His Gln Glu Ala Ile Glu Lys Val Thr Glu Ala Leu
                645                 650                 655

Lys Ile Asn Asn Leu Arg Leu Val Thr Leu Glu His Gln Val Leu Val
                660                 665                 670

Ile Gly Leu Lys Val Glu Ala Met Glu Lys Phe Leu Tyr Thr Ala Phe
            675                 680                 685

Ala Met Gln Glu Leu Gly Cys Asn Gln Asn Gln Phe Phe Cys Lys Val
            690                 695                 700

Pro Pro Glu Leu Trp Met Arg Tyr Asn Met Ser Ile Asn Gln Thr Ile
705                 710                 715                 720
```

```
Trp Asn His Gly Asn Ile Thr Leu Gly Glu Trp Tyr Asn Gln Thr Lys
                725                 730                 735

Asp Leu Gln Gln Lys Phe Tyr Glu Ile Ile Met Asp Ile Glu Gln Asn
            740                 745                 750

Asn Val Gln Gly Lys Lys Gly Ile Gln Gln Leu Gln Lys Trp Glu Asp
            755                 760                 765

Trp Val Gly Trp Ile Gly Asn Ile Pro Gln Tyr Leu Lys Gly Leu Leu
        770                 775                 780

Gly Gly Ile Leu Gly Ile Gly Leu Gly Val Leu Leu Ile Leu Cys
785                 790                 795                 800

Leu Pro Thr Leu Val Asp Cys Ile Arg Asn Cys Ile His Lys Ile Leu
                805                 810                 815

Gly Tyr Thr Val Ile Ala Met Pro Glu Val Glu Gly Glu Glu Ile Gln
                820                 825                 830

Pro Gln Met Glu Leu Arg Arg Asn Gly Arg Gln Cys Gly Ile Ser Glu
            835                 840                 845

Lys Glu Glu Glu
    850
```

(2) INFORMATION FOR SEQ ID NO:4:

(i) SEQUENCE CHARACTERISTICS:
        (A) LENGTH: 1350 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

```
ATGGGGAACG GACAGGGGCG AGATTGGAAA ATGGCCATTA AGAGATGTAG TAATGTTGCT      60
GTAGGAGTAG GGGGGAAGAG TAAAAAATTT GGAGAAGGGA ATTTCAGATG GGCCATTAGA     120
ATGGCTAATG TATCTACAGG ACGAGAACCT GGTGATATAC CAGAGACTTT AGATCAACTA     180
AGGTTGGTTA TTTGCGATTT ACAAGAAAGA GAGAAAAAT TTGGGTCGAG CAAAGAAATT      240
GACATGGCAA TTGTTACATT AAAAGTCTTT GCGGTAGTAG GACTTTTAAA TATGACAGTG     300
TCTACTGCTG CTGCAGCTGA AAATATGTAC ACTCAGATGG GATTAGACAC TAGACCATCT     360
ATGAGAGAAG CAGGAGGAAA AGAGGAAAGC CCTCCACAGG CATCTCCTAT TCAAACAGCA     420
AATGGAGCAC ACAATATGT AGCACTTGAC CCAAAAATGG TGTCCATTTT TATGGAAAAG     480
GCAAGAGAAG GATTAGGAGG TGAGGAAGTT CAGCTATGGT TTACTGCCTT CTCTGCAAAT     540
TTAACACCTA CTGACATGGC CACATTAATA ATGGCCGCAC CAGGGTGCGC TGCAGATAAA     600
GAAATATTGG ATGAAAGCTT AAAGCAATTG ACGGCAGAGT ATGATCGTAC CCATCCTCCT     660
GATGGACCTA GACCATTACC CTATTTTACT GCAGCAGAAA TTATGGGTAT AGGATTAACT     720
CAAGAACAAC AAGCAGAAGC AAGATTTGCA CCAGCTAGGA TGCAGTGTAG AGCATGGTAT     780
CTCGAGGCAC TAGGAAAATT GGCCGCCATA AAAGCTAAGT CTCCTCGAGC TGTGCAGTTA     840
AGACAAGGAG CTAAGGAAGA TTATTCATCC TTTATAGACA GATTGTTTGC CCAAATAGAT     900
CAAGAACAAA ATACAGCTGA AGTTAAGTTA TATTTAAAAC AGTCATTAAG CATGGCTAAT     960
GCTAATGCAG AATGTAAAAA GGCAATGAGC CACCTTAAGC CAGAAAGTAC CCTAGAAGAA    1020
AAGCTGAGAG CTTGTCAAGA AGTAGGCTCA CCAGGATATA AAATGCAACT CTTGGCAGAA    1080
GCTCTTACAA AAGTTCAAGT AGTGCAATCA AAAGGATCAG GACCAGTGTG TTTCAACTGT    1140
AAAAACCAG GACATCTAGC AAAACAGTGT AGAGATGTGA AAAAATGTAA TAAATGTGGA    1200
```

```
AAGCCTGGTC ATTTAGCTGC CAAATGCTGG CAAGGTGGTA AAAAGAATTC GGGAAACTGG      1260

AAGGCGGGGC GAGCTGCAGC CCCAGTGAAT CAAGTGCAGC AAGCAGTAAT GCCATCTGCA      1320

CCTCCAATGG AGGAGAGACT ATTGGATTTA                                      1350
```

(2) INFORMATION FOR SEQ ID NO:5:

(i) SEQUENCE CHARACTERISTICS:
        (A) LENGTH: 405 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..405

(xi) SEQUENCE DESCRIPTION: SEQ ID NO:5:

```
ATG GGG AAC GGA CAG GGG CGA GAT TGG AAA ATG GCC ATT AAG AGA TGT           48
Met Gly Asn Gly Gln Gly Arg Asp Trp Lys Met Ala Ile Lys Arg Cys
            855                 860                 865

AGT AAT GTT GCT GTA GGA GTA GGG GGG AAG AGT AAA AAA TTT GGA GAA           96
Ser Asn Val Ala Val Gly Val Gly Gly Lys Ser Lys Lys Phe Gly Glu
    870                 875                 880

GGG AAT TTC AGA TGG GCC ATT AGA ATG GCT AAT GTA TCT ACA GGA CGA          144
Gly Asn Phe Arg Trp Ala Ile Arg Met Ala Asn Val Ser Thr Gly Arg
885                 890                 895                 900

GAA CCT GGT GAT ATA CCA GAG ACT TTA GAT CAA CTA AGG TTG GTT ATT          192
Glu Pro Gly Asp Ile Pro Glu Thr Leu Asp Gln Leu Arg Leu Val Ile
                905                 910                 915

TGC GAT TTA CAA GAA AGA AGA GAA AAA TTT GGG TCG AGC AAA GAA ATT          240
Cys Asp Leu Gln Glu Arg Arg Glu Lys Phe Gly Ser Ser Lys Glu Ile
            920                 925                 930

GAC ATG GCA ATT GTT ACA TTA AAA GTC TTT GCG GTA GTA GGA CTT TTA          288
Asp Met Ala Ile Val Thr Leu Lys Val Phe Ala Val Val Gly Leu Leu
        935                 940                 945

AAT ATG ACA GTG TCT ACT GCT GCT GCA GCT GAA AAT ATG TAC ACT CAG          336
Asn Met Thr Val Ser Thr Ala Ala Ala Ala Glu Asn Met Tyr Thr Gln
    950                 955                 960

ATG GGA TTA GAC ACT AGA CCA TCT ATG AGA GAA GCA GGA GGA AAA GAG          384
Met Gly Leu Asp Thr Arg Pro Ser Met Arg Glu Ala Gly Gly Lys Glu
965                 970                 975                 980

GAA AGC CCT CCA CAG GCA TCT                                              405
Glu Ser Pro Pro Gln Ala Ser
                985
```

(2) INFORMATION FOR SEQ ID NO:6:

(i) SEQUENCE CHARACTERISTICS:
        (A) LENGTH: 135 amino acids
        (B) TYPE: amino acid
        (D) TOPOLOGY: linear (ii) MOLECULE TYPE: protein (xi) SEQUENCE DESCRIPTION: SEQ ID NO:6:

```
Met Gly Asn Gly Gln Gly Arg Asp Trp Lys Met Ala Ile Lys Arg Cys
  1               5                  10                  15

Ser Asn Val Ala Val Gly Val Gly Gly Lys Ser Lys Lys Phe Gly Glu
             20                  25                  30

Gly Asn Phe Arg Trp Ala Ile Arg Met Ala Asn Val Ser Thr Gly Arg
```

-continued

```
                35                  40                  45
Glu Pro Gly Asp Ile Pro Glu Thr Leu Asp Gln Leu Arg Leu Val Ile
         50                  55                  60

Cys Asp Leu Gln Glu Arg Arg Glu Lys Phe Gly Ser Ser Lys Glu Ile
 65                  70                  75                  80

Asp Met Ala Ile Val Thr Leu Lys Val Phe Ala Val Val Gly Leu Leu
                 85                  90                  95

Asn Met Thr Val Ser Thr Ala Ala Ala Glu Asn Met Tyr Thr Gln
                100                 105                 110

Met Gly Leu Asp Thr Arg Pro Ser Met Arg Glu Ala Gly Gly Lys Glu
            115                 120                 125

Glu Ser Pro Pro Gln Ala Ser
130                 135
```

(2) INFORMATION FOR SEQ ID NO:7:

(i) SEQUENCE CHARACTERISTICS:
      (A) LENGTH: 669 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 1..669

(xi) SEQUENCE DESCRIPTION: SEQ ID NO:7:

```
CCT ATT CAA ACA GCA AAT GGA GCA CCA CAA TAT GTA GCA CTT GAC CCA     48
Pro Ile Gln Thr Ala Asn Gly Ala Pro Gln Tyr Val Ala Leu Asp Pro
                140                 145                 150

AAA ATG GTG TCC ATT TTT ATG GAA AAG GCA AGA GAA GGA TTA GGA GGT     96
Lys Met Val Ser Ile Phe Met Glu Lys Ala Arg Glu Gly Leu Gly Gly
            155                 160                 165

GAG GAA GTT CAG CTA TGG TTT ACT GCC TTC TCT GCA AAT TTA ACA CCT    144
Glu Glu Val Gln Leu Trp Phe Thr Ala Phe Ser Ala Asn Leu Thr Pro
        170                 175                 180

ACT GAC ATG GCC ACA TTA ATA ATG GCC GCA CCA GGG TGC GCT GCA GAT    192
Thr Asp Met Ala Thr Leu Ile Met Ala Ala Pro Gly Cys Ala Ala Asp
185                 190                 195

AAA GAA ATA TTG GAT GAA AGC TTA AAG CAA TTG ACG GCA GAG TAT GAT    240
Lys Glu Ile Leu Asp Glu Ser Leu Lys Gln Leu Thr Ala Glu Tyr Asp
200                 205                 210                 215

CGT ACC CAT CCT CCT GAT GGA CCT AGA CCA TTA CCC TAT TTT ACT GCA    288
Arg Thr His Pro Pro Asp Gly Pro Arg Pro Leu Pro Tyr Phe Thr Ala
                220                 225                 230

GCA GAA ATT ATG GGT ATA GGA TTA ACT CAA GAA CAA CAA GCA GAA GCA    336
Ala Glu Ile Met Gly Ile Gly Leu Thr Gln Glu Gln Gln Ala Glu Ala
            235                 240                 245

AGA TTT GCA CCA GCT AGG ATG CAG TGT AGA GCA TGG TAT CTC GAG GCA    384
Arg Phe Ala Pro Ala Arg Met Gln Cys Arg Ala Trp Tyr Leu Glu Ala
        250                 255                 260

CTA GGA AAA TTG GCC GCC ATA AAA GCT AAG TCT CCT CGA GCT GTG CAG    432
Leu Gly Lys Leu Ala Ala Ile Lys Ala Lys Ser Pro Arg Ala Val Gln
265                 270                 275

TTA AGA CAA GGA GCT AAG GAA GAT TAT TCA TCC TTT ATA GAC AGA TTG    480
Leu Arg Gln Gly Ala Lys Glu Asp Tyr Ser Ser Phe Ile Asp Arg Leu
280                 285                 290                 295

TTT GCC CAA ATA GAT CAA GAA CAA AAT ACA GCT GAA GTT AAG TTA TAT    528
Phe Ala Gln Ile Asp Gln Glu Gln Asn Thr Ala Glu Val Lys Leu Tyr
```

```
                    300              305              310
TTA AAA CAG TCA TTA AGC ATG GCT AAT GCT AAT GCA GAA TGT AAA AAG      576
Leu Lys Gln Ser Leu Ser Met Ala Asn Ala Asn Ala Glu Cys Lys Lys
                315              320              325

GCA ATG AGC CAC CTT AAG CCA GAA AGT ACC CTA GAA GAA AAG CTG AGA      624
Ala Met Ser His Leu Lys Pro Glu Ser Thr Leu Glu Glu Lys Leu Arg
            330              335              340

GCT TGT CAA GAA GTA GGC TCA CCA GGA TAT AAA ATG CAA CTC TTG          669
Ala Cys Gln Glu Val Gly Ser Pro Gly Tyr Lys Met Gln Leu Leu
345              350              355
```

(2) INFORMATION FOR SEQ ID NO:8:

(i) SEQUENCE CHARACTERISTICS:
        (A) LENGTH: 223 amino acids
        (B) TYPE: amino acid
        (D) TOPOLOGY: linear (ii) MOLECULE TYPE: protein (xi) SEQUENCE DESCRIPTION: SEQ ID NO:8:

```
Pro Ile Gln Thr Ala Asn Gly Ala Pro Gln Tyr Val Ala Leu Asp Pro
1               5                   10                  15

Lys Met Val Ser Ile Phe Met Glu Lys Ala Arg Glu Gly Leu Gly Gly
                20                  25                  30

Glu Glu Val Gln Leu Trp Phe Thr Ala Phe Ser Ala Asn Leu Thr Pro
            35                  40                  45

Thr Asp Met Ala Thr Leu Ile Met Ala Ala Pro Gly Cys Ala Ala Asp
        50                  55                  60

Lys Glu Ile Leu Asp Glu Ser Leu Lys Gln Leu Thr Ala Glu Tyr Asp
65                  70                  75                  80

Arg Thr His Pro Pro Asp Gly Pro Arg Pro Leu Pro Tyr Phe Thr Ala
                85                  90                  95

Ala Glu Ile Met Gly Ile Gly Leu Thr Gln Glu Gln Ala Glu Ala
                100                 105                 110

Arg Phe Ala Pro Ala Arg Met Gln Cys Arg Ala Trp Tyr Leu Glu Ala
            115                 120                 125

Leu Gly Lys Leu Ala Ala Ile Lys Ala Lys Ser Pro Arg Ala Val Gln
        130                 135                 140

Leu Arg Gln Gly Ala Lys Glu Asp Tyr Ser Ser Phe Ile Asp Arg Leu
145                 150                 155                 160

Phe Ala Gln Ile Asp Gln Glu Gln Asn Thr Ala Glu Val Lys Leu Tyr
                165                 170                 175

Leu Lys Gln Ser Leu Ser Met Ala Asn Ala Asn Ala Glu Cys Lys Lys
            180                 185                 190

Ala Met Ser His Leu Lys Pro Glu Ser Thr Leu Glu Glu Lys Leu Arg
        195                 200                 205

Ala Cys Gln Glu Val Gly Ser Pro Gly Tyr Lys Met Gln Leu Leu
210                 215                 220
```

(2) INFORMATION FOR SEQ ID NO:9:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(ix) FEATURE:
    (A) NAME/KEY: CDS
    (B) LOCATION: 1..42

(xi) SEQUENCE DESCRIPTION: SEQ ID NO:9:

```
GCA GAG TAT GAT CGT ACC CAT CCT CCT GAT GGA CCT AGA CCA        42
Ala Glu Tyr Asp Arg Thr His Pro Pro Asp Gly Pro Arg Pro
225                 230                 235
```

(2) INFORMATION FOR SEQ ID NO:10:

(i) SEQUENCE CHARACTERISTICS:
        (A) LENGTH: 14 amino acids
        (B) TYPE: amino acid
        (D) TOPOLOGY: linear (ii) MOLECULE TYPE: protein (xi) SEQUENCE DESCRIPTION: SEQ ID NO:10:

```
Ala Glu Tyr Asp Arg Thr His Pro Pro Asp Gly Pro Arg Pro
1               5                   10
```

(2) INFORMATION FOR SEQ ID NO:11:

(i) SEQUENCE CHARACTERISTICS:
        (A) LENGTH: 264 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..264

(xi) SEQUENCE DESCRIPTION: SEQ ID NO:11:

```
ACA AAA GTT CAA GTA GTG CAA TCA AAA GGA TCA GGA CCA GTG TGT TTC    48
Thr Lys Val Gln Val Val Gln Ser Lys Gly Ser Gly Pro Val Cys Phe
15                  20                  25                  30

AAC TGT AAA AAA CCA GGA CAT CTA GCA AAA CAG TGT AGA GAT GTG AAA    96
Asn Cys Lys Lys Pro Gly His Leu Ala Lys Gln Cys Arg Asp Val Lys
                35                  40                  45

AAA TGT AAT AAA TGT GGA AAG CCT GGT CAT TTA GCT GCC AAA TGC TGG   144
Lys Cys Asn Lys Cys Gly Lys Pro Gly His Leu Ala Ala Lys Cys Trp
            50                  55                  60

CAA GGT GGT AAA AAG AAT TCG GGA AAC TGG AAG GCG GGG CGA GCT GCA   192
Gln Gly Gly Lys Lys Asn Ser Gly Asn Trp Lys Ala Gly Arg Ala Ala
        65                  70                  75

GCC CCA GTG AAT CAA GTG CAG CAA GCA GTA ATG CCA TCT GCA CCT CCA   240
Ala Pro Val Asn Gln Val Gln Gln Ala Val Met Pro Ser Ala Pro Pro
    80                  85                  90

ATG GAG GAG AGA CTA TTG GAT TTA                                   264
Met Glu Glu Arg Leu Leu Asp Leu
95                  100
```

(2) INFORMATION FOR SEQ ID NO:12:

(i) SEQUENCE CHARACTERISTICS:
        (A) LENGTH: 88 amino acids
        (B) TYPE: amino acid
        (D) TOPOLOGY: linear (ii) MOLECULE TYPE: protein (xi) SEQUENCE DESCRIPTION: SEQ ID NO:12:

```
Thr Lys Val Gln Val Val Gln Ser Lys Gly Ser Gly Pro Val Cys Phe
```

```
               1               5                    10                   15
           Asn Cys Lys Lys Pro Gly His Leu Ala Lys Gln Cys Arg Asp Val Lys
                           20                  25                  30
           Lys Cys Asn Lys Cys Gly Lys Pro Gly His Leu Ala Ala Lys Cys Trp
                       35                  40                  45
           Gln Gly Gly Lys Lys Asn Ser Gly Asn Trp Lys Ala Gly Arg Ala Ala
                   50                  55                  60
           Ala Pro Val Asn Gln Val Gln Gln Ala Val Met Pro Ser Ala Pro Pro
           65                  70                  75                  80
           Met Glu Glu Arg Leu Leu Asp Leu
                           85
```

(2) INFORMATION FOR SEQ ID NO:13:

(i) SEQUENCE CHARACTERISTICS:
        (A) LENGTH: 3841 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

```
ATGATTGGAG TAGGAGGAGG AAAGAGAGGA ACAAATTATA TCAATGTGCA TTTAGAGATT     60

AGAGATGAAA ATTATAAGAC ACAATGTATA TTTGGCAATG TTTGTGTCTT AGAAGATAAC    120

TCATTAATAC AACCATTATT AGGGAGAGAT AATATGATTA GATTCAATAT TAGGTTAGTA    180

ATGGCTCAAA TTTCTGACAA GATTCCAATA GTAAAAGTAA AAATGAAGGA TCCAAATAAA    240

GGACCTCAAA TAAAACAATG GCCATTAACA AATGAAAAAA TTGAAGCTTT AACAGAAATA    300

GTAGAAAGAC TAGAAAGAGA AGGGAAAGTA AAAAGAGCAG ATCCAAATAA CCCATGGAAT    360

ACACCAGTAT TTGCAATAAA AAAGAAAAGT GGAAAATGGA GAATGCTCAT AGATTTTAGA    420

GAATTGAACA AATTAACTGA AAAGGGGCA GAAGTCCAGT TAGGACTCCC TCATCCTGCT     480

GGATTAAAAA TGAAAAAACA AGTTACTGTG CTAGATATAG GAGATGCATA CTTCACTATT    540

CCCTTGGATC CAGACTATGC TCCCTATACT GCATTCACAT TACCTAGAAA GAATAATGCA    600

GGACCAGGGA GGAGATATGT ATGGTGCAGT TTACCACAGG GGTGGGTTCT AAGCCCATTG    660

ATATATCAAA GTACTTTAGA TAATATAATA CAACCTTTTA TTAGACAAAA TCCTGAGTTA    720

GATATTTATC AATATATGGA TGACATTTAT ATAGGATCAA ACTTAAGTAA AAAGGAGCAT    780

AAAGAAAAAG TAGAAGAATT AAGAAAATTG TTATTATGGT GGGGATTTGA AACCCCGGAA    840

GACAAATTAC AAGAAGAGCC CCCATATAAG TGGATGGGCT ATGAATTACA TCCATTAACA    900

TGGTCAATAC AGCAAAAACA ATTAGAAATT CCAGAAAGAC CCACATTAAA TGAACTGCAG    960

AAATTAGCAG GTAAGATAAA CTGGGCCAGT CAAACTATCC CAGACTTAAG TATAAAAGAA   1020

CTAACTAACA TGATGAGAGG AGATCAGAAG TTAGACTCAA TAAGAGAATG GACTGTGGAA   1080

GCCAAGAGAG AAGTACAAAA AGCTAAGGAA GCTATTGAGA TGCAAGCACA GCTAAATTAT   1140

TATGATCCCC ACCGAGAATT ATATGCAAAA TTAAGTTTAG TGGGACCACA TCAAATATGT   1200

TATCAAGTGT ATCATAAGAA CCCAGAATGT ATTTTATGGT ATGGTAAGAT GAATAGACAA   1260

AAGAAAAAGG CAGAAAATAC CTGTGATATA GCTCTAAGGG CATGTTATAA AATAAGAGAA   1320

GAATCTATTA TAAGAATAGG AAAAGAACCA ATATATGAAA TACCTACTTC TAGAGAAGCC   1380

TGGGAGTCAA ATTTAATTAA TTCACCATAT CTTAAGGCCC CACCTCCTGA GGTAGAATAT   1440

ATCCATGCTG CTGTGAATAT AAAAAGAGCA TTAAGTATGA TAAAAGATGT TCCAATACCA   1500
```

```
GAAGCAGAAA CGTGGTATAT AGATGGAGGC AGAAAGCTAG GAAAAGCAGC AAAAGCAGCC   1560

TATTGGACAG ATACAGGGAA GTGGCAAGTA ATGGAGTTAG AAGGCAGTAA TCAGAAGGCA   1620

GAAGTACAAG CATTATTATT GGCATTAAAA GCAGGATCAG AGGAAATGAA TATTATAACA   1680

GATTCACAAT ATGTTATAAA TATTATTCTT CAACAACCAG ATATGATGGA GGGAATCTGG   1740

CAAGAAGTTT TAGAAGAATT GGAGAAAAAA ACAGCAATAT TTATAGATTG GGTCCCAGGA   1800

CATAAAGGTA TTCCAGGAAA TGAGGAAGTA GATAAGCTTT GTCAAACAAT GATGATAATA   1860

GAAGGGGATG GGATATTAGA TAAAAGGTCA GAAGATGCGG GATATGATTT ATTGGCTGCA   1920

AAAGAAATAC ATTTATTGCC AGGAGAGGTA AAAGTAATAC CAACAGGGGT AAAGCTAATG   1980

CTGCCTAAAG GACATTGGGG ACTAATAATG GGAAGAAGCT CGATAGGGAG TAAAGGATTG   2040

GATGTATTAG GAGGGTAAT AGATGAAGGA TATCGAGGTG AAATTGGAGT AATAATGATT   2100

AATGTATCAA GAAAATCAAT CACCTTAATG GAACAACAAA AGATAGCACA ATTAATAATA   2160

TTGCCTTGTA AACATGAAGT ATTAGAACAA GGAAAAGTTG TAATGGATTC AGAGAGAGGA   2220

GACAAAGGTT ATGGGTCAAC AGGAGTATTC TCCTCTTGGG TTGACAGGAT TGAGGAAGCA   2280

GAAATAAATC ATGAAAAATT TCACTCAGAT CCACAATACT TAAGGACTGA ATTTAATTTA   2340

CCCAAGATGG TTGCAGAAGA GATAAGACGA AAGTGCCCTG TATGTAGAAT CAGAGGAGAA   2400

CAAGTGGGAG GACAATTGAA ATAGGGCCTG GAATATGGC AAGTGGATTG CACACACTTT   2460

AATAGTAAGA TAATCATTGT AGCAGTACAT GTGGAATCAG GATTTTTATG GGCACAGATA   2520

ATTCCACAGG AGACTGCAGA TTGTACAGTC AAGGCTCTTC TGCAACTTAT ATGTGCTCAT   2580

AATGTTACAG AATTACAAAC AGACAATGGA CCAAATTTTA AAAATCAGAA AATGGAAGGT   2640

TTATTAAATT TTATGGGAAT AAAACATAAA TTAGGGATAC CAGGTAACCC ACAATCACAG   2700

GCATTAGTGG AAAATGCTAA TAACACATTA AAAGCTTGGA TTCAAAAATT CCTACCAGAG   2760

ACTACCTCTC TGGATAATGC TCTGGCCCTA GCCCTGTATA GTCTCAACTT TAAACAAAGG   2820

GGTAGACTAG GAAGGATGGC CCCTTATGAA TTATACATAC AACAAGAATC ATTAAGAATA   2880

CAAGACTATT TTTCGCAGAT TCCACAAAAG TTAATGATGC AGTGGGTGTA TTACAAAGAT   2940

CAAAAAGACA AAAAATGGAA GGGACCAATG AGAGTGGAAT ATTGGGGACA GGATCAGTA    3000

TTATTAAAGG ATGAAGAGAA GGGATATTTT CTTGTACCTA GGAGACACAT AAGAAGAGTC   3060

CCAGAACCCT GCACTCTTCC TGAAGGGGAT GAGTGACGAA GATTGGCAGG TAAGTAGAAG   3120

ACTCTTTGCA GTGCTCCAAG GAGGAGTACG TAGTGCTATG CTATACATAT CTAGACTACC   3180

TCCGGACGAA AGAAAAGGT ATAAAAAAGA CTTTAAGAAA AGGCTTTTGG AAAAGGAAAC    3240

AGGATTCATA CAGAGATTAA GAAAAGCGGA AGGAATAAGG TGGAGCTTCC ATACTAGAGA   3300

TTATTATATA GGATATGTAA GAGAGATGGT GGCCGGATCT AGTCTACCAG ATAGTTTAAG   3360

ACTGTATATT TATATAAGCA ATCCATTGTG GCACTGGTCA TACCGTCCTG GCCTGACAAA   3420

TTTTAATACA GAATGGCCTT TTGTGAATAT GTGGATAAAG ACAGGATTCA TGTGGGATGA   3480

TATTGAAAGC CAGAATATTT GCAAAGGAGG AGAGATTTCA CATGGATGGG GACCTGGAAT   3540

GGTGGGAATT GTGATAAAAG CTTTTAGTTG TGGAGAAAGA AAGATTGAGG CTACTCCTGT   3600

AATGATTATA AGAGGAGAAA TAGATCCAAA AAAATGGTGT GGAGATTGTT GGAATTTGAT   3660

GTGTCTTAGG AACTCACCTC CACAGACTTT ACAAAGACTT GCTATGTTGG CATGTGGCGT   3720

GCCGGCTAAG GAGTGGCGAG GATGCTGTAA TCAACGCTTT GTTTCTCCTT ACAGAACGCC   3780

TGCTGATTTG GAGGTCATTC AATCCAAGCC CAGCTGGAGT CTATTATGGT CAGGGAGCCT   3840
```

—continued

A 3841

(2) INFORMATION FOR SEQ ID NO:14:

(i) SEQUENCE CHARACTERISTICS:
        (A) LENGTH: 3093 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..3093

(xi) SEQUENCE DESCRIPTION: SEQ ID NO:14:

```
ATG ATT GGA GTA GGA GGA GGA AAG AGA GGA ACA AAT TAT ATC AAT GTG       48
Met Ile Gly Val Gly Gly Gly Lys Arg Gly Thr Asn Tyr Ile Asn Val
 90                  95                 100

CAT TTA GAG ATT AGA GAT GAA AAT TAT AAG ACA CAA TGT ATA TTT GGC       96
His Leu Glu Ile Arg Asp Glu Asn Tyr Lys Thr Gln Cys Ile Phe Gly
105                 110                 115                 120

AAT GTT TGT GTC TTA GAA GAT AAC TCA TTA ATA CAA CCA TTA TTA GGG      144
Asn Val Cys Val Leu Glu Asp Asn Ser Leu Ile Gln Pro Leu Leu Gly
                125                 130                 135

AGA GAT AAT ATG ATT AGA TTC AAT ATT AGG TTA GTA ATG GCT CAA ATT      192
Arg Asp Asn Met Ile Arg Phe Asn Ile Arg Leu Val Met Ala Gln Ile
                140                 145                 150

TCT GAC AAG ATT CCA ATA GTA AAA GTA AAA ATG AAG GAT CCA AAT AAA      240
Ser Asp Lys Ile Pro Ile Val Lys Val Lys Met Lys Asp Pro Asn Lys
                155                 160                 165

GGA CCT CAA ATA AAA CAA TGG CCA TTA ACA AAT GAA AAA ATT GAA GCT      288
Gly Pro Gln Ile Lys Gln Trp Pro Leu Thr Asn Glu Lys Ile Glu Ala
170                 175                 180

TTA ACA GAA ATA GTA GAA AGA CTA GAA AGA GAA GGG AAA GTA AAA AGA      336
Leu Thr Glu Ile Val Glu Arg Leu Glu Arg Glu Gly Lys Val Lys Arg
185                 190                 195                 200

GCA GAT CCA AAT AAC CCA TGG AAT ACA CCA GTA TTT GCA ATA AAA AAG      384
Ala Asp Pro Asn Asn Pro Trp Asn Thr Pro Val Phe Ala Ile Lys Lys
                205                 210                 215

AAA AGT GGA AAA TGG AGA ATG CTC ATA GAT TTT AGA GAA TTG AAC AAA      432
Lys Ser Gly Lys Trp Arg Met Leu Ile Asp Phe Arg Glu Leu Asn Lys
                220                 225                 230

TTA ACT GAG AAA GGG GCA GAA GTC CAG TTA GGA CTC CCT CAT CCT GCT      480
Leu Thr Glu Lys Gly Ala Glu Val Gln Leu Gly Leu Pro His Pro Ala
                235                 240                 245

GGA TTA AAA ATG AAA AAA CAA GTT ACT GTG CTA GAT ATA GGA GAT GCA      528
Gly Leu Lys Met Lys Lys Gln Val Thr Val Leu Asp Ile Gly Asp Ala
250                 255                 260

TAC TTC ACT ATT CCC TTG GAT CCA GAC TAT GCT CCC TAT ACT GCA TTC      576
Tyr Phe Thr Ile Pro Leu Asp Pro Asp Tyr Ala Pro Tyr Thr Ala Phe
265                 270                 275                 280

ACA TTA CCT AGA AAG AAT AAT GCA GGA CCA GGG AGG AGA TAT GTA TGG      624
Thr Leu Pro Arg Lys Asn Asn Ala Gly Pro Gly Arg Arg Tyr Val Trp
                285                 290                 295

TGC AGT TTA CCA CAG GGG TGG GTT CTA AGC CCA TTG ATA TAT CAA AGT      672
Cys Ser Leu Pro Gln Gly Trp Val Leu Ser Pro Leu Ile Tyr Gln Ser
                300                 305                 310

ACT TTA GAT AAT ATA ATA CAA CCT TTT ATT AGA CAA AAT CCT GAG TTA      720
Thr Leu Asp Asn Ile Ile Gln Pro Phe Ile Arg Gln Asn Pro Glu Leu
                315                 320                 325
```

```
GAT ATT TAT CAA TAT ATG GAT GAC ATT TAT ATA GGA TCA AAC TTA AGT      768
Asp Ile Tyr Gln Tyr Met Asp Asp Ile Tyr Ile Gly Ser Asn Leu Ser
    330                 335                 340

AAA AAG GAG CAT AAA GAA AAA GTA GAA GAA TTA AGA AAA TTG TTA TTA      816
Lys Lys Glu His Lys Glu Lys Val Glu Glu Leu Arg Lys Leu Leu Leu
345                 350                 355                 360

TGG TGG GGA TTT GAA ACC CCG GAA GAC AAA TTA CAA GAA GAG CCC CCA      864
Trp Trp Gly Phe Glu Thr Pro Glu Asp Lys Leu Gln Glu Glu Pro Pro
                365                 370                 375

TAT AAG TGG ATG GGC TAT GAA TTA CAT CCA TTA ACA TGG TCA ATA CAG      912
Tyr Lys Trp Met Gly Tyr Glu Leu His Pro Leu Thr Trp Ser Ile Gln
            380                 385                 390

CAA AAA CAA TTA GAA ATT CCA GAA AGA CCC ACA TTA AAT GAA CTG CAG      960
Gln Lys Gln Leu Glu Ile Pro Glu Arg Pro Thr Leu Asn Glu Leu Gln
        395                 400                 405

AAA TTA GCA GGT AAG ATA AAC TGG GCC AGT CAA ACT ATC CCA GAC TTA     1008
Lys Leu Ala Gly Lys Ile Asn Trp Ala Ser Gln Thr Ile Pro Asp Leu
    410                 415                 420

AGT ATA AAA GAA CTA ACT AAC ATG ATG AGA GGA GAT CAG AAG TTA GAC     1056
Ser Ile Lys Glu Leu Thr Asn Met Met Arg Gly Asp Gln Lys Leu Asp
425                 430                 435                 440

TCA ATA AGA GAA TGG ACT GTG GAA GCC AAG AGA GAA GTA CAA AAA GCT     1104
Ser Ile Arg Glu Trp Thr Val Glu Ala Lys Arg Glu Val Gln Lys Ala
                445                 450                 455

AAG GAA GCT ATT GAG ATG CAA GCA CAG CTA AAT TAT TAT GAT CCC CAC     1152
Lys Glu Ala Ile Glu Met Gln Ala Gln Leu Asn Tyr Tyr Asp Pro His
            460                 465                 470

CGA GAA TTA TAT GCA AAA TTA AGT TTA GTG GGA CCA CAT CAA ATA TGT     1200
Arg Glu Leu Tyr Ala Lys Leu Ser Leu Val Gly Pro His Gln Ile Cys
        475                 480                 485

TAT CAA GTG TAT CAT AAG AAC CCA GAA TGT ATT TTA TGG TAT GGT AAG     1248
Tyr Gln Val Tyr His Lys Asn Pro Glu Cys Ile Leu Trp Tyr Gly Lys
    490                 495                 500

ATG AAT AGA CAA AAG AAA AAG GCA GAA AAT ACC TGT GAT ATA GCT CTA     1296
Met Asn Arg Gln Lys Lys Lys Ala Glu Asn Thr Cys Asp Ile Ala Leu
505                 510                 515                 520

AGG GCA TGT TAT AAA ATA AGA GAA GAA TCT ATT ATA AGA ATA GGA AAA     1344
Arg Ala Cys Tyr Lys Ile Arg Glu Glu Ser Ile Ile Arg Ile Gly Lys
                525                 530                 535

GAA CCA ATA TAT GAA ATA CCT ACT TCT AGA GAA GCC TGG GAG TCA AAT     1392
Glu Pro Ile Tyr Glu Ile Pro Thr Ser Arg Glu Ala Trp Glu Ser Asn
            540                 545                 550

TTA ATT AAT TCA CCA TAT CTT AAG GCC CCA CCT CCT GAG GTA GAA TAT     1440
Leu Ile Asn Ser Pro Tyr Leu Lys Ala Pro Pro Pro Glu Val Glu Tyr
        555                 560                 565

ATC CAT GCT GCT GTG AAT ATA AAA AGA GCA TTA AGT ATG ATA AAA GAT     1488
Ile His Ala Ala Val Asn Ile Lys Arg Ala Leu Ser Met Ile Lys Asp
    570                 575                 580

GTT CCA ATA CCA GAA GCA GAA ACG TGG TAT ATA GAT GGA GGC AGA AAG     1536
Val Pro Ile Pro Glu Ala Glu Thr Trp Tyr Ile Asp Gly Gly Arg Lys
585                 590                 595                 600

CTA GGA AAA GCA GCA AAA GCA GCC TAT TGG ACA GAT ACA GGG AAG TGG     1584
Leu Gly Lys Ala Ala Lys Ala Ala Tyr Trp Thr Asp Thr Gly Lys Trp
                605                 610                 615

CAA GTA ATG GAG TTA GAA GGC AGT AAT CAG AAG GCA GAA GTA CAA GCA     1632
Gln Val Met Glu Leu Glu Gly Ser Asn Gln Lys Ala Glu Val Gln Ala
            620                 625                 630

TTA TTA TTG GCA TTA AAA GCA GGA TCA GAG GAA ATG AAT ATT ATA ACA     1680
Leu Leu Leu Ala Leu Lys Ala Gly Ser Glu Glu Met Asn Ile Ile Thr
        635                 640                 645
```

```
GAT TCA CAA TAT GTT ATA AAT ATT ATT CTT CAA CAA CCA GAT ATG ATG         1728
Asp Ser Gln Tyr Val Ile Asn Ile Ile Leu Gln Gln Pro Asp Met Met
    650                 655                 660

GAG GGA ATC TGG CAA GAA GTT TTA GAA GAA TTG GAG AAA AAA ACA GCA         1776
Glu Gly Ile Trp Gln Glu Val Leu Glu Glu Leu Glu Lys Lys Thr Ala
665                 670                 675                 680

ATA TTT ATA GAT TGG GTC CCA GGA CAT AAA GGT ATT CCA GGA AAT GAG         1824
Ile Phe Ile Asp Trp Val Pro Gly His Lys Gly Ile Pro Gly Asn Glu
                685                 690                 695

GAA GTA GAT AAG CTT TGT CAA ACA ATG ATG ATA ATA GAA GGG GAT GGG         1872
Glu Val Asp Lys Leu Cys Gln Thr Met Met Ile Ile Glu Gly Asp Gly
            700                 705                 710

ATA TTA GAT AAA AGG TCA GAA GAT GCG GGA TAT GAT TTA TTG GCT GCA         1920
Ile Leu Asp Lys Arg Ser Glu Asp Ala Gly Tyr Asp Leu Leu Ala Ala
        715                 720                 725

AAA GAA ATA CAT TTA TTG CCA GGA GAG GTA AAA GTA ATA CCA ACA GGG         1968
Lys Glu Ile His Leu Leu Pro Gly Glu Val Lys Val Ile Pro Thr Gly
    730                 735                 740

GTA AAG CTA ATG CTG CCT AAA GGA CAT TGG GGA CTA ATA ATG GGA AGA         2016
Val Lys Leu Met Leu Pro Lys Gly His Trp Gly Leu Ile Met Gly Arg
745                 750                 755                 760

AGC TCG ATA GGG AGT AAA GGA TTG GAT GTA TTA GGA GGG GTA ATA GAT         2064
Ser Ser Ile Gly Ser Lys Gly Leu Asp Val Leu Gly Gly Val Ile Asp
                765                 770                 775

GAA GGA TAT CGA GGT GAA ATT GGA GTA ATA ATG ATT AAT GTA TCA AGA         2112
Glu Gly Tyr Arg Gly Glu Ile Gly Val Ile Met Ile Asn Val Ser Arg
            780                 785                 790

AAA TCA ATC ACC TTA ATG GAA CAA CAA AAG ATA GCA CAA TTA ATA ATA         2160
Lys Ser Ile Thr Leu Met Glu Gln Gln Lys Ile Ala Gln Leu Ile Ile
        795                 800                 805

TTG CCT TGT AAA CAT GAA GTA TTA GAA CAA GGA AAA GTT GTA ATG GAT         2208
Leu Pro Cys Lys His Glu Val Leu Glu Gln Gly Lys Val Val Met Asp
    810                 815                 820

TCA GAG AGA GGA GAC AAA GGT TAT GGG TCA ACA GGA GTA TTC TCC TCT         2256
Ser Glu Arg Gly Asp Lys Gly Tyr Gly Ser Thr Gly Val Phe Ser Ser
825                 830                 835                 840

TGG GTT GAC AGG ATT GAG GAA GCA GAA ATA AAT CAT GAA AAA TTT CAC         2304
Trp Val Asp Arg Ile Glu Glu Ala Glu Ile Asn His Glu Lys Phe His
                845                 850                 855

TCA GAT CCA CAA TAC TTA AGG ACT GAA TTT AAT TTA CCC AAG ATG GTT         2352
Ser Asp Pro Gln Tyr Leu Arg Thr Glu Phe Asn Leu Pro Lys Met Val
            860                 865                 870

GCA GAA GAG ATA AGA CGA AAG TGC CCT GTA TGT AGA ATC AGA GGA GAA         2400
Ala Glu Glu Ile Arg Arg Lys Cys Pro Val Cys Arg Ile Arg Gly Glu
        875                 880                 885

CAA GTG GGA GGA CAA TTG AAA ATA GGG CCT GGA ATA TGG CAA GTG GAT         2448
Gln Val Gly Gly Gln Leu Lys Ile Gly Pro Gly Ile Trp Gln Val Asp
    890                 895                 900

TGC ACA CAC TTT AAT AGT AAG ATA ATC ATT GTA GCA GTA CAT GTG GAA         2496
Cys Thr His Phe Asn Ser Lys Ile Ile Ile Val Ala Val His Val Glu
905                 910                 915                 920

TCA GGA TTT TTA TGG GCA CAG ATA ATT CCA CAG GAG ACT GCA GAT TGT         2544
Ser Gly Phe Leu Trp Ala Gln Ile Ile Pro Gln Glu Thr Ala Asp Cys
                925                 930                 935

ACA GTC AAG GCT CTT CTG CAA CTT ATA TGT GCT CAT AAT GTT ACA GAA         2592
Thr Val Lys Ala Leu Leu Gln Leu Ile Cys Ala His Asn Val Thr Glu
            940                 945                 950

TTA CAA ACA GAC AAT GGA CCA AAT TTT AAA AAT CAG AAA ATG GAA GGT         2640
Leu Gln Thr Asp Asn Gly Pro Asn Phe Lys Asn Gln Lys Met Glu Gly
```

```
                 955                 960                 965
TTA TTA AAT TTT ATG GGA ATA AAA CAT AAA TTA GGG ATA CCA GGT AAC     2688
Leu Leu Asn Phe Met Gly Ile Lys His Lys Leu Gly Ile Pro Gly Asn
        970                 975                 980

CCA CAA TCA CAG GCA TTA GTG GAA AAT GCT AAT AAC ACA TTA AAA GCT     2736
Pro Gln Ser Gln Ala Leu Val Glu Asn Ala Asn Asn Thr Leu Lys Ala
985                 990                 995                 1000

TGG ATT CAA AAA TTC CTA CCA GAG ACT ACC TCT CTG GAT AAT GCT CTG     2784
Trp Ile Gln Lys Phe Leu Pro Glu Thr Thr Ser Leu Asp Asn Ala Leu
            1005                1010                1015

GCC CTA GCC CTG TAT AGT CTC AAC TTT AAA CAA AGG GGT AGA CTA GGA     2832
Ala Leu Ala Leu Tyr Ser Leu Asn Phe Lys Gln Arg Gly Arg Leu Gly
                1020                1025                1030

AGG ATG GCC CCT TAT GAA TTA TAC ATA CAA CAA GAA TCA TTA AGA ATA     2880
Arg Met Ala Pro Tyr Glu Leu Tyr Ile Gln Gln Glu Ser Leu Arg Ile
                    1035                1040                1045

CAA GAC TAT TTT TCG CAG ATT CCA CAA AAG TTA ATG ATG CAG TGG GTG     2928
Gln Asp Tyr Phe Ser Gln Ile Pro Gln Lys Leu Met Met Gln Trp Val
        1050                1055                1060

TAT TAC AAA GAT CAA AAA GAC AAA AAA TGG AAG GGA CCA ATG AGA GTG     2976
Tyr Tyr Lys Asp Gln Lys Asp Lys Lys Trp Lys Gly Pro Met Arg Val
1065                1070                1075                1080

GAA TAT TGG GGA CAA GGA TCA GTA TTA TTA AAG GAT GAA GAG AAG GGA     3024
Glu Tyr Trp Gly Gln Gly Ser Val Leu Leu Lys Asp Glu Glu Lys Gly
                1085                1090                1095

TAT TTT CTT GTA CCT AGG AGA CAC ATA AGA AGA GTC CCA GAA CCC TGC     3072
Tyr Phe Leu Val Pro Arg Arg His Ile Arg Arg Val Pro Glu Pro Cys
                    1100                1105                1110

ACT CTT CCT GAA GGG GAT GAG                                         3093
Thr Leu Pro Glu Gly Asp Glu
            1115

(2) INFORMATION FOR SEQ ID NO:15:

(i) SEQUENCE CHARACTERISTICS:
        (A) LENGTH: 1031 amino acids
        (B) TYPE: amino acid
        (D) TOPOLOGY: linear (ii) MOLECULE TYPE: protein (xi) SEQUENCE DESCRIPTION: SEQ ID NO:15:

Met Ile Gly Val Gly Gly Gly Lys Arg Gly Thr Asn Tyr Ile Asn Val
 1               5                  10                  15

His Leu Glu Ile Arg Asp Glu Asn Tyr Lys Thr Gln Cys Ile Phe Gly
                20                  25                  30

Asn Val Cys Val Leu Glu Asp Asn Ser Leu Ile Gln Pro Leu Leu Gly
            35                  40                  45

Arg Asp Asn Met Ile Arg Phe Asn Ile Arg Leu Val Met Ala Gln Ile
 50                  55                  60

Ser Asp Lys Ile Pro Ile Val Lys Val Lys Met Lys Asp Pro Asn Lys
 65                  70                  75                  80

Gly Pro Gln Ile Lys Gln Trp Pro Leu Thr Asn Glu Lys Ile Glu Ala
                85                  90                  95

Leu Thr Glu Ile Val Glu Arg Leu Glu Arg Glu Gly Lys Val Lys Arg
                100                 105                 110

Ala Asp Pro Asn Asn Pro Trp Asn Thr Pro Val Phe Ala Ile Lys Lys
            115                 120                 125

Lys Ser Gly Lys Trp Arg Met Leu Ile Asp Phe Arg Glu Leu Asn Lys
```

```
                130                 135                 140
Leu Thr Glu Lys Gly Ala Glu Val Gln Leu Gly Leu Pro His Pro Ala
145                 150                 155                 160
Gly Leu Lys Met Lys Lys Gln Val Thr Val Leu Asp Ile Gly Asp Ala
                165                 170                 175
Tyr Phe Thr Ile Pro Leu Asp Pro Asp Tyr Ala Pro Tyr Thr Ala Phe
            180                 185                 190
Thr Leu Pro Arg Lys Asn Asn Ala Gly Pro Gly Arg Arg Tyr Val Trp
                195                 200                 205
Cys Ser Leu Pro Gln Gly Trp Val Leu Ser Pro Leu Ile Tyr Gln Ser
            210                 215                 220
Thr Leu Asp Asn Ile Ile Gln Pro Phe Ile Arg Gln Asn Pro Glu Leu
225                 230                 235                 240
Asp Ile Tyr Gln Tyr Met Asp Asp Ile Tyr Ile Gly Ser Asn Leu Ser
                245                 250                 255
Lys Lys Glu His Lys Glu Lys Val Glu Glu Leu Arg Lys Leu Leu Leu
                260                 265                 270
Trp Trp Gly Phe Glu Thr Pro Glu Asp Lys Leu Gln Glu Glu Pro Pro
            275                 280                 285
Tyr Lys Trp Met Gly Tyr Glu Leu His Pro Leu Thr Trp Ser Ile Gln
            290                 295                 300
Gln Lys Gln Leu Glu Ile Pro Glu Arg Pro Thr Leu Asn Glu Leu Gln
305                 310                 315                 320
Lys Leu Ala Gly Lys Ile Asn Trp Ala Ser Gln Thr Ile Pro Asp Leu
                325                 330                 335
Ser Ile Lys Glu Leu Thr Asn Met Met Arg Gly Asp Gln Lys Leu Asp
            340                 345                 350
Ser Ile Arg Glu Trp Thr Val Glu Ala Lys Arg Glu Val Gln Lys Ala
            355                 360                 365
Lys Glu Ala Ile Glu Met Gln Ala Gln Leu Asn Tyr Tyr Asp Pro His
370                 375                 380
Arg Glu Leu Tyr Ala Lys Leu Ser Leu Val Gly Pro His Gln Ile Cys
385                 390                 395                 400
Tyr Gln Val Tyr His Lys Asn Pro Glu Cys Ile Leu Trp Tyr Gly Lys
                405                 410                 415
Met Asn Arg Gln Lys Lys Lys Ala Glu Asn Thr Cys Asp Ile Ala Leu
                420                 425                 430
Arg Ala Cys Tyr Lys Ile Arg Glu Glu Ser Ile Ile Arg Ile Gly Lys
            435                 440                 445
Glu Pro Ile Tyr Glu Ile Pro Thr Ser Arg Glu Ala Trp Glu Ser Asn
            450                 455                 460
Leu Ile Asn Ser Pro Tyr Leu Lys Ala Pro Pro Glu Val Glu Tyr
465                 470                 475                 480
Ile His Ala Ala Val Asn Ile Lys Arg Ala Leu Ser Met Ile Lys Asp
                485                 490                 495
Val Pro Ile Pro Glu Ala Glu Thr Trp Tyr Ile Asp Gly Gly Arg Lys
            500                 505                 510
Leu Gly Lys Ala Ala Lys Ala Ala Tyr Trp Thr Asp Thr Gly Lys Trp
            515                 520                 525
Gln Val Met Glu Leu Glu Gly Ser Asn Gln Lys Ala Glu Val Gln Ala
            530                 535                 540
Leu Leu Leu Ala Leu Lys Ala Gly Ser Glu Glu Met Asn Ile Ile Thr
545                 550                 555                 560
```

-continued

```
Asp Ser Gln Tyr Val Ile Asn Ile Ile Leu Gln Gln Pro Asp Met Met
                565                 570                 575

Glu Gly Ile Trp Gln Glu Val Leu Glu Leu Glu Lys Lys Thr Ala
            580                 585                 590

Ile Phe Ile Asp Trp Val Pro Gly His Lys Gly Ile Pro Gly Asn Glu
            595                 600                 605

Glu Val Asp Lys Leu Cys Gln Thr Met Met Ile Ile Glu Gly Asp Gly
            610                 615                 620

Ile Leu Asp Lys Arg Ser Glu Asp Ala Gly Tyr Asp Leu Leu Ala Ala
625                 630                 635                 640

Lys Glu Ile His Leu Leu Pro Gly Glu Val Lys Val Ile Pro Thr Gly
                645                 650                 655

Val Lys Leu Met Leu Pro Lys Gly His Trp Gly Leu Ile Met Gly Arg
                660                 665                 670

Ser Ser Ile Gly Ser Lys Gly Leu Asp Val Leu Gly Gly Val Ile Asp
                675                 680                 685

Glu Gly Tyr Arg Gly Glu Ile Gly Val Ile Met Ile Asn Val Ser Arg
            690                 695                 700

Lys Ser Ile Thr Leu Met Glu Gln Gln Lys Ile Ala Gln Leu Ile Ile
705                 710                 715                 720

Leu Pro Cys Lys His Glu Val Leu Glu Gln Gly Lys Val Val Met Asp
                725                 730                 735

Ser Glu Arg Gly Asp Lys Gly Tyr Gly Ser Thr Gly Val Phe Ser Ser
                740                 745                 750

Trp Val Asp Arg Ile Glu Glu Ala Glu Ile Asn His Glu Lys Phe His
                755                 760                 765

Ser Asp Pro Gln Tyr Leu Arg Thr Glu Phe Asn Leu Pro Lys Met Val
770                 775                 780

Ala Glu Glu Ile Arg Arg Lys Cys Pro Val Cys Arg Ile Arg Gly Glu
785                 790                 795                 800

Gln Val Gly Gly Gln Leu Lys Ile Gly Pro Gly Ile Trp Gln Val Asp
                805                 810                 815

Cys Thr His Phe Asn Ser Lys Ile Ile Ile Val Ala Val His Val Glu
            820                 825                 830

Ser Gly Phe Leu Trp Ala Gln Ile Ile Pro Gln Glu Thr Ala Asp Cys
            835                 840                 845

Thr Val Lys Ala Leu Leu Gln Leu Ile Cys Ala His Asn Val Thr Glu
            850                 855                 860

Leu Gln Thr Asp Asn Gly Pro Asn Phe Lys Asn Gln Lys Met Glu Gly
865                 870                 875                 880

Leu Leu Asn Phe Met Gly Ile Lys His Lys Leu Gly Ile Pro Gly Asn
                885                 890                 895

Pro Gln Ser Gln Ala Leu Val Glu Asn Ala Asn Asn Thr Leu Lys Ala
            900                 905                 910

Trp Ile Gln Lys Phe Leu Pro Glu Thr Thr Ser Leu Asp Asn Ala Leu
            915                 920                 925

Ala Leu Ala Leu Tyr Ser Leu Asn Phe Lys Gln Arg Gly Arg Leu Gly
            930                 935                 940

Arg Met Ala Pro Tyr Glu Leu Tyr Ile Gln Gln Glu Ser Leu Arg Ile
945                 950                 955                 960

Gln Asp Tyr Phe Ser Gln Ile Pro Gln Lys Leu Met Met Gln Trp Val
                965                 970                 975
```

```
Tyr Tyr Lys Asp Gln Lys Asp Lys Lys Trp Lys Gly Pro Met Arg Val
        980             985             990

Glu Tyr Trp Gly Gln Gly Ser Val Leu Leu Lys Asp Glu Glu Lys Gly
    995                 1000            1005

Tyr Phe Leu Val Pro Arg Arg His Ile Arg Arg Val Pro Glu Pro Cys
    1010            1015            1020

Thr Leu Pro Glu Gly Asp Glu
1025            1030

(2) INFORMATION FOR SEQ ID NO:16:

(i) SEQUENCE CHARACTERISTICS:
        (A) LENGTH: 753 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..753

(xi) SEQUENCE DESCRIPTION: SEQ ID NO:16:

ATG ATT GAC GAA GAT TGG CAG GTA AGT AGA AGA CTC TTT GCA GTG CTC      48
Met Ile Asp Glu Asp Trp Gln Val Ser Arg Arg Leu Phe Ala Val Leu
        1035            1040            1045

CAA GGA GGA GTA CGT AGT GCT ATG CTA TAC ATA TCT AGA CTA CCT CCG      96
Gln Gly Gly Val Arg Ser Ala Met Leu Tyr Ile Ser Arg Leu Pro Pro
        1050            1055            1060

GAC GAA AGA GAA AGG TAT AAA AAA GAC TTT AAG AAA AGG CTT TTG GAA     144
Asp Glu Arg Glu Arg Tyr Lys Lys Asp Phe Lys Lys Arg Leu Leu Glu
        1065            1070            1075

AAG GAA ACA GGA TTC ATA CAG AGA TTA AGA AAA GCG GAA GGA ATA AGG     192
Lys Glu Thr Gly Phe Ile Gln Arg Leu Arg Lys Ala Glu Gly Ile Arg
1080            1085            1090            1095

TGG AGC TTC CAT ACT AGA GAT TAT TAT ATA GGA TAT GTA AGA GAG ATG     240
Trp Ser Phe His Thr Arg Asp Tyr Tyr Ile Gly Tyr Val Arg Glu Met
                1100            1105            1110

GTG GCC GGA TCT AGT CTA CCA GAT AGT TTA AGA CTG TAT ATT TAT ATA     288
Val Ala Gly Ser Ser Leu Pro Asp Ser Leu Arg Leu Tyr Ile Tyr Ile
        1115            1120            1125

AGC AAT CCA TTG TGG CAC TGG TCA TAC CGT CCT GGC CTG ACA AAT TTT     336
Ser Asn Pro Leu Trp His Trp Ser Tyr Arg Pro Gly Leu Thr Asn Phe
        1130            1135            1140

AAT ACA GAA TGG CCT TTT GTG AAT ATG TGG ATA AAG ACA GGA TTC ATG     384
Asn Thr Glu Trp Pro Phe Val Asn Met Trp Ile Lys Thr Gly Phe Met
1145            1150            1155

TGG GAT GAT ATT GAA AGC CAG AAT ATT TGC AAA GGA GGA GAG ATT TCA     432
Trp Asp Asp Ile Glu Ser Gln Asn Ile Cys Lys Gly Gly Glu Ile Ser
1160            1165            1170            1175

CAT GGA TGG GGA CCT GGA ATG GTG GGA ATT GTG ATA AAA GCT TTT AGT     480
His Gly Trp Gly Pro Gly Met Val Gly Ile Val Ile Lys Ala Phe Ser
                1180            1185            1190

TGT GGA GAA AGA AAG ATT GAG GCT ACT CCT GTA ATG ATT ATA AGA GGA     528
Cys Gly Glu Arg Lys Ile Glu Ala Thr Pro Val Met Ile Ile Arg Gly
        1195            1200            1205

GAA ATA GAT CCA AAA AAA TGG TGT GGA GAT TGT TGG AAT TTG ATG TGT     576
Glu Ile Asp Pro Lys Lys Trp Cys Gly Asp Cys Trp Asn Leu Met Cys
        1210            1215            1220

CTT AGG AAC TCA CCT CCA CAG ACT TTA CAA AGA CTT GCT ATG TTG GCA     624
Leu Arg Asn Ser Pro Pro Gln Thr Leu Gln Arg Leu Ala Met Leu Ala
```

```
                1225                1230                1235
TGT GGC GTG CCG GCT AAG GAG TGG CGA GGA TGC TGT AAT CAA CGC TTT    672
Cys Gly Val Pro Ala Lys Glu Trp Arg Gly Cys Cys Asn Gln Arg Phe
1240                1245                1250                1255

GTT TCT CCT TAC AGA ACG CCT GCT GAT TTG GAG GTC ATT CAA TCC AAG    720
Val Ser Pro Tyr Arg Thr Pro Ala Asp Leu Glu Val Ile Gln Ser Lys
                1260                1265                1270

CCC AGC TGG AGT CTA TTA TGG TCA GGG AGC CTA                        753
Pro Ser Trp Ser Leu Leu Trp Ser Gly Ser Leu
            1275                1280

(2) INFORMATION FOR SEQ ID NO:17:

(i) SEQUENCE CHARACTERISTICS:
        (A) LENGTH: 251 amino acids
        (B) TYPE: amino acid
        (D) TOPOLOGY: linear (ii) MOLECULE TYPE: protein (xi) SEQUENCE DESCRIPTION: SEQ ID NO:17:

Met Ile Asp Glu Asp Trp Gln Val Ser Arg Arg Leu Phe Ala Val Leu
 1               5                  10                  15

Gln Gly Gly Val Arg Ser Ala Met Leu Tyr Ile Ser Arg Leu Pro Pro
                20                  25                  30

Asp Glu Arg Glu Arg Tyr Lys Lys Asp Phe Lys Lys Arg Leu Leu Glu
            35                  40                  45

Lys Glu Thr Gly Phe Ile Gln Arg Leu Arg Lys Ala Glu Gly Ile Arg
     50                  55                  60

Trp Ser Phe His Thr Arg Asp Tyr Tyr Ile Gly Tyr Val Arg Glu Met
65                  70                  75                  80

Val Ala Gly Ser Ser Leu Pro Asp Ser Leu Arg Leu Tyr Ile Tyr Ile
                85                  90                  95

Ser Asn Pro Leu Trp His Trp Ser Tyr Arg Pro Gly Leu Thr Asn Phe
                100                 105                 110

Asn Thr Glu Trp Pro Phe Val Asn Met Trp Ile Lys Thr Gly Phe Met
            115                 120                 125

Trp Asp Asp Ile Glu Ser Gln Asn Ile Cys Lys Gly Gly Glu Ile Ser
130                 135                 140

His Gly Trp Gly Pro Gly Met Val Gly Ile Val Ile Lys Ala Phe Ser
145                 150                 155                 160

Cys Gly Glu Arg Lys Ile Glu Ala Thr Pro Val Met Ile Ile Arg Gly
                165                 170                 175

Glu Ile Asp Pro Lys Lys Trp Cys Gly Asp Cys Trp Asn Leu Met Cys
            180                 185                 190

Leu Arg Asn Ser Pro Pro Gln Thr Leu Gln Arg Leu Ala Met Leu Ala
        195                 200                 205

Cys Gly Val Pro Ala Lys Glu Trp Arg Gly Cys Cys Asn Gln Arg Phe
210                 215                 220

Val Ser Pro Tyr Arg Thr Pro Ala Asp Leu Glu Val Ile Gln Ser Lys
225                 230                 235                 240

Pro Ser Trp Ser Leu Leu Trp Ser Gly Ser Leu
            245                 250

(2) INFORMATION FOR SEQ ID NO:18:

(i) SEQUENCE CHARACTERISTICS:
        (A) LENGTH: 2556 base pairs
```

(B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:18:

```
ATGGCAGAAG GATTTGCAGC CAATAGACAA TGGATAGGAC CAGAAGAAGC TGAAGAGTTA      60
TTAGATTTTG ATATAGCAAC ACAAATGAAT GAAGAAGGGC CACTAAATCC AGGGATGAAC     120
CCATTTAGGG TACCTGGAAT AACAGATAAA GAAAAGCAAG ACTATTGTAA CATATTACAA     180
CCTAAGTTAC AAGATTTACG GAATGAACTT CAAGAGGTAA ACTAGAAGA AGGAAATGCA      240
GGTAAGTTTA GAAGGGCAAG ATATTTAAGA TATTCTGATG AAAATGTGCT ATCTATAGTC     300
TATTTGCTAA TAGGATATCT AAGATATTTA ATAAATCGTA GGAGTTTAGG ATCTTTAAGA     360
CATGATATAG ACATAGAAAC ACCTCAAGAG GAATATTATA GTAATAGTGA AAGGGGTACC     420
ACATTAAATC AAAAATATGC GAGAAGATGT TGTGTTAGCA CACTTATTAT GTATTTAATT     480
CTTTTTGCAG TAGGCATCTG GTGGGGAGCT AGAGCACAAG TAGTGTGGAG ACTTCCCCCT     540
TTAGTAGTTC CAGTAGAAGA ATCAGAAATA ATTTTTTGGG ATTGTTGGGC ACCAGAAGAA     600
CCCGCCTGTC AAGACTTTCT TGGGGCAATG ATACATCTAA AAGCTAGTAC GAATATAAGT     660
ATACAAGAGG GACCTACCTT GGGGAATTGG GCTAGAGAAA TATGGGGAAC ATTATTCAAA     720
AAGGCTACCA GACAATGTAG AAGAGGTAGA ATATGGAAAA GATGGAATGA AACTATAACA     780
GGACCATTAG GATGTGCTAA TAACACATGT TATAATATTT CAGTAATAGT ACCTGATTAT     840
CAATGTTATC TAGACCGAGT AGATACTTGG TTACAAGGGA AAGTAAATAT ATCATTATGT     900
CTAACAGGAG GAAAAATGTT GTACAATAAA TATACAAAAC AATTAAGCTA TTGTACAGAC     960
CCATTACAAA TCCCACTGAT CAATTATACA TTTGGACCTA ATCAAACATG TATGTGGAAC    1020
ACTTCACAAA TTCAGGACCC TGAGATACCA AAATGTGGAT GGTGGAATCA AGAGCCTAT    1080
TATAAAAATT GTAAATGGGA AAAAACAGAT GTAAAGTTTC ATTGTCAAAG AACACAGAGT    1140
CAGCCTGGAA CATGGCTTAG AGCAATCTCG TCATGGAGAC AAAGGAATAG ATGGGAATGG    1200
AGACCAGATT TTGAAAGTGA AAAGGTGAAA ATATCTCTAA AGTGTAATAG CACAAAAAAC    1260
CTAACCTTTG CAATGAGAAG TTCAGGAGAT TATGGAGAAG TAACGGGAGC TTGGATAGAG    1320
TTTGGATGTC ATAGAAATAA ATCAAAACTT CATGATGAAG CAAGGTTTAG AATTAGATGT    1380
AGATGGAATA TAGGGGAGAA TACCTCACTC ATTGATACAT GTGGAAACAC TCAAAATGTT    1440
TCAGGGCAA ATCCTGTAGA TTGTACCATG TATGCAAATA AAATGTACAA TTGTTCTTTA    1500
CAAAACGGGT TTACTATGAA GGTAGATGAC CTTATTATGC ATTTCAATAT GACAAAAGCT    1560
GTAGAAATGT ATAATATTGC TGGAAATTGG TCTTGTACAT CTGACTTGCC ACCAACATGG    1620
GGGTATATGA ATTGTAACTG TACAAATAAT AGTAATGATA ATACTAGAAT GGCATGTCCT    1680
AACAATCAAG GCATCTTAAG GAATTGGTAT AACCCAGTAG CAGGATTACG ACAATCCTTG    1740
GAAAAGTATC AAGTTGTAAA ACAACCAGAT TACTTAGTGG TCCCAGGGGA AGTCATGGAA    1800
TATAAAACTA GAAGGAAAAG GGCAGCTATT CATGTTATGT TAGCTCTTGC AACAGTATTA    1860
TCTATGGCCG GAGCAGGGAC GGGGGCTACT GCTATAGGGA TGGTAACACA ATATCACCAA    1920
GTTCTAGCAA CCCATCAAGA AGCTATTGAA AAGGTGACTG AAGCCTTAAA GATAAACAAC    1980
TTGAGATTAG TTACATTAGA GCATCAAGTA CTAGTAATAG GATTAAAAGT AGAAGCTATG    2040
GAAAAATTTT TATATACAGC TTTCGCTATG CAAGAATTAG GATGTAATCA AAATCAATTC    2100
TTCTGCAAAG TCCCTCCTGA ATTGTGGATG AGGTATAATA TGTCTATAAA TCAAACAATA    2160
```

TGGAATCATG GAAATATAAC TTTGGGGGAA TGGTATAACC AAACAAAAGA TTTACAACAA    2220

AAGTTTTATG AAATAATAAT GGACATAGAA CAAAATAATG TACAAGGGAA AAAAGGGATA    2280

CAACAATTAC AAAAGTGGGA AGATTGGGTA GGATGGATAG GAAATATTCC ACAATACTTA    2340

AAGGGACTAT TGGGAGGTAT CTTGGGAATA GGATTAGGAG TGTTATTATT AATTTTATGT    2400

TTACCCACAT TGGTTGATTG TATAAGAAAT TGTATCCACA AGATACTAGG ATACACAGTA    2460

ATTGCAATGC CTGAAGTAGA AGGAGAAGAA ATACAACCAC AAATGGAATT GAGGAGAAAT    2520

GGTAGGCAAT GTGGCATATC TGAAAAAGAG GAGGAA                              2556

(2) INFORMATION FOR SEQ ID NO:19:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..36

(xi) SEQUENCE DESCRIPTION: SEQ ID NO:19:

CAA GAA TTA GGA TGT AAT CAA AAT CAA TTC TTC TGC                      36
Gln Glu Leu Gly Cys Asn Gln Asn Gln Phe Phe Cys
            255                 260

(2) INFORMATION FOR SEQ ID NO:20:

(i) SEQUENCE CHARACTERISTICS:
        (A) LENGTH: 12 amino acids
        (B) TYPE: amino acid
        (D) TOPOLOGY: linear (ii) MOLECULE TYPE: protein (xi) SEQUENCE DESCRIPTION: SEQ ID NO:20:

Gln Glu Leu Gly Cys Asn Gln Asn Gln Phe Phe Cys
 1               5                  10

(2) INFORMATION FOR SEQ ID NO:21:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

GGATGAGTAT TGGAACCCTG AA                                             22

(2) INFORMATION FOR SEQ ID NO:22:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

GATTCCGAGA CCTCACAGGT AA                                                22

(2) INFORMATION FOR SEQ ID NO:23:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

AATAGGGAAG CAGTAGCAGA C                                                 21

(2) INFORMATION FOR SEQ ID NO:24:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

GTAAATCGCA AATAACCAAC C                                                 21

(2) INFORMATION FOR SEQ ID NO:25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

TGACGGTGTC TACTGCTGCT                                                   20

(2) INFORMATION FOR SEQ ID NO:26:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

CACACTGGTC CTGATCCTTT T                                                 21

(2) INFORMATION FOR SEQ ID NO:27:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

CCACAATATG TAGCACTTGA CC                                                22

(2) INFORMATION FOR SEQ ID NO:28:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:28:

GGGTACTTTC TGGCTTAAGG TG                                              22

(2) INFORMATION FOR SEQ ID NO:29:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

GGGGGACCTA CCTTGGGGAA TTGGGCT                                         27

(2) INFORMATION FOR SEQ ID NO:30:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

GGTGATCATG ATCAGTGGGA TTTGTAATGG GTCTG                                 35

(2) INFORMATION FOR SEQ ID NO:31:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

GGTGATCATG ATCAGTGGGA TTTGTAATGG GTCTG                                 35

(2) INFORMATION FOR SEQ ID NO:32:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:32:

ATAAGGGAGA TACTGTGCTG A                                               21

(2) INFORMATION FOR SEQ ID NO:33:

(i) SEQUENCE CHARACTERISTICS:
        (A) LENGTH: 21 base pairs
        (B) TYPE: nucleic acid

```
        (C) STRANDEDNESS: single
        (D) TOPOLOGY: linear (ii) MOLECULE TYPE: DNA (genomic)

(xi) SEQUENCE DESCRIPTION: SEQ ID NO:33:

GCGATCTTCT AACTCTGTCA T                                              21
```